(12) United States Patent
Cioanta

(10) Patent No.: US 10,569,106 B2
(45) Date of Patent: Feb. 25, 2020

(54) TISSUE DISINFECTION WITH ACOUSTIC PRESSURE SHOCK WAVES

(71) Applicant: SANUWAVE, INC., Alpharetta, GA (US)

(72) Inventor: Iulian Cioanta, Milton, GA (US)

(73) Assignee: SANUWAVE, INC., Suwanee, GA (US)

( * ) Notice: Subject to any disclaimer, the term of this patent is extended or adjusted under 35 U.S.C. 154(b) by 889 days.

(21) Appl. No.: 15/135,716

(22) Filed: Apr. 22, 2016

(65) Prior Publication Data

US 2016/0310766 A1 Oct. 27, 2016

Related U.S. Application Data

(60) Provisional application No. 62/152,067, filed on Apr. 24, 2015.

(51) Int. Cl.
*A61N 7/00* (2006.01)

(52) U.S. Cl.
CPC ........ *A61N 7/00* (2013.01); *A61N 2007/0004* (2013.01); *A61N 2007/0017* (2013.01)

(58) Field of Classification Search
CPC .... A61N 2007/0004; A61N 2007/0017; A61N 7/00
See application file for complete search history.

(56) References Cited

U.S. PATENT DOCUMENTS

| | | |
|---|---|---|
| 2,968,592 A | 1/1961 | Hamilton |
| 3,917,818 A | 11/1975 | Botes |
| 4,011,312 A | 3/1977 | Reuter et al. |
| 5,198,214 A | 3/1993 | Stolle et al. |
| 5,797,872 A | 8/1998 | Ogata et al. |
| 5,846,543 A | 12/1998 | Hassler et al. |
| 6,080,119 A | 6/2000 | Schwarze et al. |
| 6,254,881 B1 | 7/2001 | McNally et al. |
| 6,562,820 B2 | 5/2003 | Watts et al. |
| 8,961,441 B2 | 2/2015 | Cioanta et al. |
| 9,198,825 B2 | 12/2015 | Katragadda et al. |
| 2007/0016112 A1 | 1/2007 | Schultheiss et al. |
| 2008/0009885 A1 | 1/2008 | Del Giglio |
| 2009/0171248 A1* | 7/2009 | Rybyanets ............ A61N 7/02 601/2 |

(Continued)

FOREIGN PATENT DOCUMENTS

| | | |
|---|---|---|
| CN | 101044990 B | 11/2011 |
| DE | 3709404 A1 | 11/1988 |
| EP | 2578209 | 10/2013 |

(Continued)

OTHER PUBLICATIONS

J.H. du Preez, Bovine Mastitis and Why it Fails, Journal of the South African Veterinary Association, vol. 71, No. 3, pp. 201-208, 2000.

(Continued)

*Primary Examiner* — Michael T Rozanski

(74) *Attorney, Agent, or Firm* — Eric J. Hanson; Polsinelli PC

(57) ABSTRACT

Human and animal infections are treated using extracorporeal acoustic pressure shock waves that destroy harmful pathogens as bacteria, viruses, funguses and other microorganisms to disinfect infected tissue.

19 Claims, 33 Drawing Sheets

(56) References Cited

U.S. PATENT DOCUMENTS

2014/0243715 A1   8/2014   Cioanta

FOREIGN PATENT DOCUMENTS

WO   93/14720 A1     8/1993
WO   2014/153257 A2  9/2014

OTHER PUBLICATIONS

A.C. Kudi, et al., "Mastitis Causing Pathogens within the Dairy Cattle Environment", International Journal of Biology, vol. 1, No. 1, pp. 3-13, 2009.

L. Gerdesmeyer, et al., "Antibacterial Effects of Extracorporeal Shock Waves", Ultrasound in Medicine and Biology, Elsevier, United Kingdom, vol. 31, No. 1 pp. 115-119, 2005.

C. Horn, et al., "The Effect of Antibacterial Acting Extracorporeal Shock Waves on Bacterial Cell Integrity", Medical Science Monitor, vol. 15, No. 12, pp. BR364-BR369, 2009.

J. Holfeld, et al., "Shockwave Therapy Differentially Stimulates Endothelial Cells: Implications on the Control of Inflammation via Toll-Like Receptor 3", Inflammation, vol. 37, No. 1, pp. 65-70, 2014.

E. Wallhausser, et al., "Acoustic Impedance Analysis for Determining Presence and Cleaning Success of Dairy Fouling", Fouling and Cleaning in Food Processing, Cambridge, UK 22024, Mar. 2010.

L. Krokowicz, et al., "Pulsed Acoustic Cellular Treatment Induces Expression of Proangiogenic Factors and Chemokines in Muscle Flaps", Journal of Trauma, vol. 69, No. 6, pp. 1448-1456, 2010.

J.M. Willis et al., Survival Limits of Bacteria During Shock Compression: Application to the Early Earth, 36th Lunar and Planetary Science Conference, Lunar and Planetary Institute, Houston, Texas, 2005.

I.R. Booth, et al., "Mechanosensitive Channels in Bacteria: Signs of Closure?", Nature Reviews, vol. 5, pp. 431-440, 2007.

L. Krokowicz, et al., "Pulsed Acoustic Cellular Expression As a Protective Therapy Against I/R Injury in a Cremaster Muscle FLap Model", Microvascular Research, Nov. 2011.

International Search Report and Written Opinion of PCT/US16/28775 dated Jul. 26, 2016.

Supplementary European Search Report dated Oct. 23, 2018, The Hague.

* cited by examiner

TISSUE DISINFECTION WITH ACOUSTIC PRESSURE SHOCK WAVES

CROSS-REFERENCE TO RELATED APPLICATIONS

This application claims the benefit of priority of U.S. provisional application No. 62/152,067, filed Apr. 24, 2015, which is incorporated herein by reference in its entirety.

BACKGROUND OF THE INVENTION

The present invention generally shows methods and device embodiments that use extracorporeal acoustic pressure shock waves for preventing and treating living tissue infections for mammals (humans and animals) in order to produce tissue disinfection.

From the treatment point of view, the preferred approach is the use of parental and local antibiotics. Numerous modern commercial antibacterial agents are available for treating infections as penicillin, oxytetracycline, chlortetracycline, cloxacillin, cephapirin, ampicilin, dihydrostreptomycin, ceftiofur, gentamicin, erythromycin, spiramycin, novobiocin, oxazolidinone, etc. The global concerns for developing antimicrobial drug resistance and the need to develop more prudent and judicious use of drugs have caused the necessity of finding new approaches to treat infections that do not display these disadvantages. Also, sometimes the infections are very difficult to treat due to the fact that they are located deep inside the body and in places where the reach of significant amounts of antibiotics is difficult, without significant side effects. One notorious example is the treatment of infections of human joints implants. In general micro-organisms that produce infection are easy to kill by antibiotics, if they are in a planktonic stage. However, in the case of implants (hip, knee, etc.) they multiply and group to form biofilms around the implant, which makes the drugs inefficient. The drugs cannot penetrate biofilms and after extensive antibiotic therapies that last up to one year, the ultimate solution is to take the implant out, which represents a significant distress to the patient and a major financial burden to modern society.

This invention also shows embodiments for preventing the onset of mastitis and treatment of mastitis in female mammals with shock waves. For humans, mastitis is most common during the first 6 months of breast-feeding and although mastitis can be discouraging and painful, it is usually easily cleared up with medicine/drugs. This is why this invention relates especially to the prevention and treatment of mastitis in milking mammals/animals, including, for example, bovine, ovine and caprine, and more specifically to either therapeutically or prophylactically treatment of cows, sheep ewes and goats against mastitis, as well as the product, which is used in the treatment.

For milking mammals/animals, mastitis is the inflammation of the mammary gland or udder tissue. It usually occurs as an immune response to bacterial invasion of the teat canal by variety of bacterial sources present on the farm (infectious mastitis), and can also occur as a result of non-infectious factors as chemical, mechanical, or thermal injury to the udder. Milk-secreting tissues and various ducts throughout the udder can be damaged by bacterial/micro-organisms toxins, and sometimes permanent damage to the udder occurs. Severe acute cases can be fatal, but even in animals that recover there may be consequences for the rest of the lactation and subsequent lactations.

Despite decades of research and steady progress, mastitis remains the most costly infectious disease affecting dairy herds. Due to mastitis contagious environmental micro-organisms can be spread through the herds and the produced milk is infected, which makes the milk unusable for consumption. The environmental micro-organisms can infect the animals not only during milking periods but also during the dry periods.

Maximizing/supplementing the animal's immunological defense and minimizing bacterial challenge from the environment represent two main principles used to prevent new mastitis infections. Mastitis treatment and control is one of the largest costs to the dairy industry and a significant factor in dairy cow welfare. Losses arise from: 1) milk thrown away due to contamination by medication/antibiotics or being unfit to drink; 2) reduction in yields due to illness and any permanent damage to udder tissue; 3) extra labor required to tend to mastitic cows; 4) costs of veterinary care, medicines; and reduced longevity due to premature culling.

When mastitis infection is present it can be broken down into following categories, dependent upon the signs and symptoms.

Subclinical mastitis represents the presence of an infection without apparent signs of local inflammation or systemic involvement. Although transient episodes of abnormal milk may appear, these infections are for the most part asymptomatic and, if the infection persists for at least 2 months, it is termed as chronic. Once established, many of these infections persist for entire lactations or the life of the cow.

Subacute mastitis shows small inflammation of the mammary gland/udder without showing any signs of fever or depression or any other systemic involvement.

Clinical mastitis (peracute and acute) is an inflammatory response to infection causing visibly abnormal milk (eg. color, fibrin clots). As the extent of the inflammation increases, changes in the udder (swelling, heat, pain, redness) may also be apparent. For clinical mastitis where the udder is swollen, hot, and red can be defined as peracute mastitis. The cow may flinch or kick when the bag/udder is touched because it is sensitive. Milk production is reduced. A general fever may be present, depression, shivering, rapid weight loss, and appetite loss occurs in many cases. For clinical mastitis where severe inflammation is present and includes systemic involvement (severe fever, anorexia, shock, mild depression, weakness, diarrhea and inactive animal), the case is termed severe or acute mastitis. In very severe/acute mastitis cases death may also occur.

Mastitis infections are produced by almost any microbe that can opportunistically invade udder tissue and cause infection. However, most infections are caused by various species of gram-positive cocci as streptococci, staphylococci, and gram-negative rods such as *Klebsiella* sp, *Serratia marcescens, Pseudomonas aeruginosa, Escherichia coli* or lactose-fermenting organisms of enteric origin, commonly termed coliforms. Mastitis can also be produced by other atypical pathogens such as mycotic and algal microbes.

Except for *Mycoplasma* spp, which may spread from cow to cow through aerosol transmission and invade the udder subsequent to bacteremia, contagious pathogens are spread during milking process. Species that use this mode of transmission include *Staphylococcus aureus, Streptococcus agalactiae,* and *Corynebacterium bovis*. Additionally, contagious transmission infrequently occurs for pathogens typically associated with environmental reservoirs, through the development of host-adapted virulence factors (*Escherichia*

*coli*) or by shedding of overwhelming numbers of bacteria from infected udders (*Trueperella pyogenes*).

From the treatment point of view the preferred approach is the use of parental and intra-mammary antibiotics. However, systemic therapy involves extra-label drug use, and milk/meat withholding periods must be determined judiciously. U.S. Pat. No. 2,968,592 teaches the use of penicillin. Numerous modern commercial antibacterial agents are available for treating mastitis besides penicillin and include oxytetracycline, chlortetracycline, cloxacillin, cephapirin, ampicilin, dihydrostreptomycin, ceftiofur, gentamicin, erythromycin, spiramycin, novobiocin, oxazolidinone (U.S. Pat. No. 6,562,820 teaches the use of oxazolidinone in the treatment of cow mastitis), etc. However, the majority of these drugs are not approved for use in dairy cows (off-label use). Also, the global concerns for developing antimicrobial drug resistance and the need to develop more prudent and judicious use of animal drugs have caused the farmers to reconsider the intervention methods of treating and controlling mastitis.

The delivery of the drugs used for mastitis is well covered. U.S. Pat. No. 4,011,312 teaches a prolonged release drug dosage form for the treatment of bovine mastitis, specifically suited for dry cow treatment, consists of an antimicrobial agent dispersed in a matrix of a low molecular weight polyester of glycolic and lactic acids, and shaped as a cylindrical bougie for facile insertion into the teat canal.

New methods for delivering the antibacterial agents in the area affected by mastitis are mentioned in other patents. For example the EP 2,578,209 patent teaches the delivery of the drugs via nano-particles, thus avoiding the inconvenience of the use of high doses of drugs used in conventional formulations, thus contributing to an improvement in milk quality.

Besides antibacterial agents, the U.S. Pat. No. 3,917,818 teaches the use of immune-globulin obtained from the pooled blood of cows suffering from mastitis.

As a novel method to treat mastitis, the U.S. Pat. No. 5,797,872 teaches the use of chemotherapy agents. Other methods used to treat mastitis without the use of antibiotics are clay therapy, homeopathy, phytotherapy, oxygen therapy, injection of egg whites into the teat, injections of copper sulphate, calcium oxide and neem oil into the udder, acupuncture, antibodies, etc. For example the U.S. Pat. No. 5,846,543 teaches the use of natural components (*Echinechea* Goldenseal Supreme; Wild *Ginseng* Supreme; *gelsemium*, pokeroot, and aconite; and aloe vera juice) for the phytotherapy treatment of cow mastitis.

Organic dairy farmers, having limited use of antibiotic treatments, often use alternative therapies such as homeopathy for the treatment of mastitis.

Other approach to treat mastitis is based on the increased/stimulated reaction of the animal immune system to the pathogen, via vaccination. Thus the U.S. Pat. No. 5,198,214 teaches the use of a polyvalent vaccine effective in the prevention and treatment of mastitis in bovine animals. For vaccine creation is done by periodically culturing the milk of animals exhibiting preclinical mastitis to cultivate any pathogens present therein, killing those pathogens and incorporating each strain of cultivated, killed pathogen in a pharmacological carrier together with all other strains previously identified.

For prevention of mastitis for dry/non-lactating animals the U.S. Pat. No. 6,254,881 teaches the creation of a mechanical seal for the teat (to prevent bacterial penetration for dry cows) using approximately 65% by weight of bismuth sub-nitrate in a gel based on aluminium stearate.

SUMMARY OF THE INVENTION

Disinfection is defined as the process of killing pathogenic organisms or rendering them inert. The act of disinfecting is given by using specialized cleansing techniques that destroy or prevent growth of organisms capable of infection. Taking into account this definition and the above mentioned effects on bacterial biofilms and planktonic bacteria given by acoustic pressure shock waves, application of extracorporeal acoustic pressure shock waves to the living tissue infections produces an efficient disinfection of the infected tissue.

The extracorporeal acoustic pressure shock waves produced by the proposed embodiments will have a compressive phase (produces high compressive pressures) and a tensile phase (produces cavitation bubbles that collapse with high speed jets) during one cycle of the acoustic pressure shock waves. This two synergetic effects work in tandem by acting at macro (compressive phase) and micro level (cavitation jets of the tensile phase), which is enhancing the effects of the acoustic pressure shock waves on the living tissue affected by infection in order to produce tissue disinfection.

For both human and animal mammals, the inflammation of the living tissue occurs after trauma and/or infection produced by bacteria, viruses, funguses and other harmful micro-organisms, which produce an immune response. The usual treatment approach is the use of local or systemic medication/drugs/antibiotics/homeopathic agents, which are targeting the specific invading organism. This medication approach to the treatment is hindered by the location in the tissue (fibrous or scar tissue) of bacteria, viruses, funguses and other harmful micro-organisms, which makes the drugs ineffective due to inflammation and poor oxygenation of the tissue that prevents drug to reach the infected tissue, resistance for the specific drug, etc. These issues can be overcome by the use of extracorporeal acoustic pressure shock waves, as presented in the embodiments of this invention. The acoustic pressure shock waves are known to have antibacterial effects demonstrated in vitro and in vivo against bacteria under both static and dynamic growth conditions. The acoustic pressure shock waves have similar action on viruses, funguses and other harmful micro-organisms, based on the same mechanisms of action produced by their compressive and tensile phases. The acoustic pressure shock waves are known to produce temporary increase of small blood vessel dimensions and in the long term can stimulate blood vessels growth, which can enhance the blood supply to the targeted area and thus allowing the modulation of inflammation and the inflow of necessary nutrients for tissue healing.

Furthermore, extracorporeal acoustic pressure shock waves can be used in conjunction with antibiotics or other medication employed for treating infections, or existing medical devices used for treating superficial, profound, local or systemic infections, without any interference. The fact that they can be applied extracorporeally and they can penetrate at any depth inside the human and animal body, without creating heat or other side effects, makes the acoustic pressure shock waves very easy to administer, as a standalone treatment or as an additional/additive treatment to other existing modalities used to treat infections.

The mechanical interaction at the tissue or cellular level inside a living organism produced by acoustic pressure shock waves can kill harmful pathogens, modulates inflammation, brings nutrients to the desired area through increased blood circulation, stimulates tissue growth and can deliver drugs locally for enhanced efficacy without side effects. Also, acoustic pressure shock waves can be transmitted and penetrate soft and hard tissue, fibrotic/scar tissue, blood vessels and body fluids, which makes them very versatile in treating any type of infections regardless of the location inside the body or type of tissue affected by infection.

In the specific case of mastitis, the existing methods used to treat mastitis have significant drawbacks due to the cost of the treatment, reduced efficacy/healing rate, collateral negative influence on the milk and/or eventually meat quality and due to the relatively complicated regimen needed to be followed, which rendered the methods to be not easy to implement in the daily routine of an animal farm. To address the drawbacks of the existing methods used to treat mastitis, the novel approach presented in the embodiments of this invention is to use the extracorporeal acoustic pressure shock waves for preventing the onset of mastitis and treatment of mastitis in female mammals, based on the acoustic pressure shock waves effects on bacterial infections that produce mastitis. The advantages of using extracorporeal acoustic pressure shock waves in the treatment of mastitis are presented in the following paragraphs.

The preferred existing method for treating mastitis is the use of different drugs to address the bacterial infection. The treatment of mastitis treatment using drugs can fail from different reasons. Thus the scientific literature shows that tissue-invading bacteria can become walled off in the udder parenchyma by thick, fibrous scar tissue so that the antibiotic cannot reach the pathogen. Also, all bacterial populations contain organisms that are not in the active growth phase that makes these non-multiplying bacteria (dormant bacteria) not sensitive to most antibiotics. Finally, the bacteriological failures may occur even when the organisms are sensitive to the antibiotics used. These issues can be overcome by the use of extracorporeal acoustic pressure shock waves that are known to have antibacterial effects demonstrated in vitro and in vivo, under both static and dynamic growth conditions. The killing of bacteria is produced by the strong mechanical forces generated by acoustic pressure shock waves combined with cavitation microjets (produced during collapse of cavitational bubbles generated by the tensile phase of acoustic pressure shock waves) that can disrupt biofilms or planktonic bacteria integrity and in the end can kill bacteria. Furthermore, localized/transient thermal effects created during collapse of the cavitation bubbles can also kill bacteria and viruses and acoustic pressure shock waves-generated free radicals can have a destructive effect on bacteria, viruses or biofilms. The penetration of the extracorporeal acoustic pressure shock waves inside the living tissue (including fibrotic tissue, parenchyma, blood vessels, etc.) allows the reach of the acoustic pressure shock waves for bacteria or viruses incorporated in the udder parenchyma by thick, fibrous scar tissue, for a more effective treatment of the mastitis.

Another reason for failure of mastitis treatments is given by the milk duct obstruction produced by edema and inflammatory products that obstruct diffusion of antibiotics to some extent by compression or blockage of the milk duct system, rendering antimicrobial contact with mastitis-causing bacteria difficult, especially with intra-mammary therapy. Extracorporeal acoustic pressure shock waves can modulate/reduce inflammation via different cellular receptors, which can help overall with the inflammation produced by mastitis and allows the bacterial killing by acoustic pressure shock waves to be highly efficient.

If the drugs are delivered systemically, there is a weak passage of the drug across the blood-milk barrier, which affects the efficacy of the drug. Furthermore, the effect of antibacterials (delivered systemically or via tit infusion) depends on interaction with the antibacterial host factors. All endogenous antibacterial factors are greatly diluted in milk and thus components in milk mask or inactivate the effect of antibacterial complement. Extracorporeal acoustic pressure shock waves propagation in different substances is given by their acoustic impedance, which is the measure of the opposition that a system presents to an acoustic flow when an acoustic pressure is applied to it. Basically, the acoustic impedance of a substance is given by the product of density of a substance/material and the speed of sound into that substance/material. In general, the acoustic pressure shock waves are traveling without any losses to deposit their energy in the targeted treatment zone, if the acoustic impedance remains relatively unchanged. In the case where acoustic impedance changes dramatically (for example from fluids to gases or to solids) the acoustic pressure shock waves are losing a part of their energy at the interface of substances that have different acoustic impedance, which makes acoustic pressure shock waves less efficient in the desired treatment zone. From this point of view, in general animal tissue has an acoustic impedance of 1.68 MRayl and the milk has an acoustic impedance of 1.56 MRayl, which suggests that acoustic pressure shock waves are traveling practically undisturbed from tissue to milk and vice versa and thus given a very successful treatment of bacteria that produce mastitis, regardless of milk presence.

Udder tissue necrosis leads to a poor blood supply to the affected areas that result in a decreased redox potential that favors anaerobic bacteria. Practically, there is no effective passage of drug into necrotic udder tissue. It is well known from scientific literature that acoustic pressure shock waves have proangiogenic action (forms new blood vessels from pre-existing vessels) via endothelial nitric oxide synthase [eNOS], vascular endothelial growth factor [VEGF], and different chemokines. This means that the acoustic pressure shock waves can produce new small blood vessels in the tissue affected by bacteria, which can enhance the blood supply and nutrients brought to the mastitis affected area and thus helping with the healing. Besides the antibacterial effects of the acoustic pressure shock waves for both aerobic and anaerobic bacteria, the proangiogenic action of the acoustic pressure shock waves can help with enhancing the passage of different antibiotics into the udder the tissue, in cases where antibiotics are administered concomitantly.

Biochemical resistance of bacteria to antimicrobial agents may occur by mutation, natural selection, transformation, transduction or conjugation, which produces antibiotic resistance. Bacteria initially sensitive to an antimicrobial agent may become resistant, and another antimicrobial agent must then be used. Acoustic pressure shock waves are destroying the integrity of the bacteria by affecting their membrane integrity or by interfering with bacterium mechanotransduction via localized pressure variations produced by acoustic pressure shock waves. Thus there is no developed resistance of bacteria to acoustic pressure shock waves, due to their mutation, natural selection, transformation, transduction or conjugation.

Tissues lining the teat duct are very delicate and any unnatural manipulation of this structure, such as cannula insertion, may jeopardize antibacterial function, and predispose the quarter to infection or reinfection. Furthermore, it is possible to introduce a second pathogen by insertion of a contaminated cannula into the teat or with intramammary drug infusion where the teat tips are not thoroughly cleaned and disinfected before treatment. Acoustic pressure shock waves being delivered extracorporeally (from outside the teat/udder) are avoiding the problems generated by invasive techniques.

The utilization of extracorporeal acoustic pressure shock waves to destroy pathogens that produce infection of the living tissue, and in particular for prevention the onset of mastitis or treatment of mastitis in female mammals, is described in the present invention, which provides in its embodiments different methods and designs, which can be used to eliminate harmful micro-organisms that affect living tissue and thus disinfecting the infected tissue.

In methods and designs presented in different embodiments of the invention, acoustic pressure shock waves can be produced using any principle including, but not limited to, electrohydraulic (high voltage or laser generated), piezoelectric, or electromagnetic principles. Each treatment may include a certain number of acoustic pressure shock waves, at a certain energy level and frequency indicative of the treatment settings. Also, the acoustic pressure shock waves can be focused, unfocused, planar, pseudo-planar or radial. The acoustic pressure shock waves prefereably have a high compressive phase followed by a strong tensile phase that produces significant cavitation. The high velocity cavitation microjets generated during collapse of the cavitation bubbles play an important role in permanently breaching the membrane of the bacteria, viruses and other micro-organisms, which produce tissue infection, and particularly mastitis. The possible membrane breaching combined with the disruption of normal mechanotransduction that affects the transport of substances across the membrane of the bacteria, viruses and other micro-organisms, has the potential to destroy them and thus to eliminate tissue infection and finally disinfect the infected tissue.

Although the examples from this patent refer specifically to human living tissue infections and mastitis treatment for milking mammals/animals, embodiments can also be used for other medical applications (besides living tissue infection) for humans or animals, where the specific construction of the applicators conforms very well to particular anatomic features of the body as toes, torso, legs, etc., for an optimal delivery of acoustic pressure shock waves to the targeted treatment area, as required by a specific medical condition that needs to be addressed.

DETAILED DESCRIPTION OF THE INVENTION

Embodiments of the invention will be described with reference to the accompanying figures, wherein like numbers represent like elements throughout. Further, it is to be understood that the phraseology and terminology used herein is for the purpose of description and should not be regarded as limiting. The use of "including", "comprising", or "having" and variations thereof herein is meant to encompass the items listed thereafter and equivalents thereof as well as additional items. The terms "connected", and "coupled" are used broadly and encompass both direct and indirect mounting, connecting and coupling. Further, "connected" and "coupled" are not restricted to physical or mechanical connections or couplings.

Embodiments to produce living tissue disinfection in general for both human and animals are further described in detail in the following paragraphs.

It is an objective of the present inventions to provide acoustic pressure shock waves generating devices that are modular, do not need high maintenance and can, if needed, be applied/used in conjunction with other devices, drugs, methods and existing treatments for disinfection of living tissue infections or prevention of infections (prophylactic use).

Figure 1A:
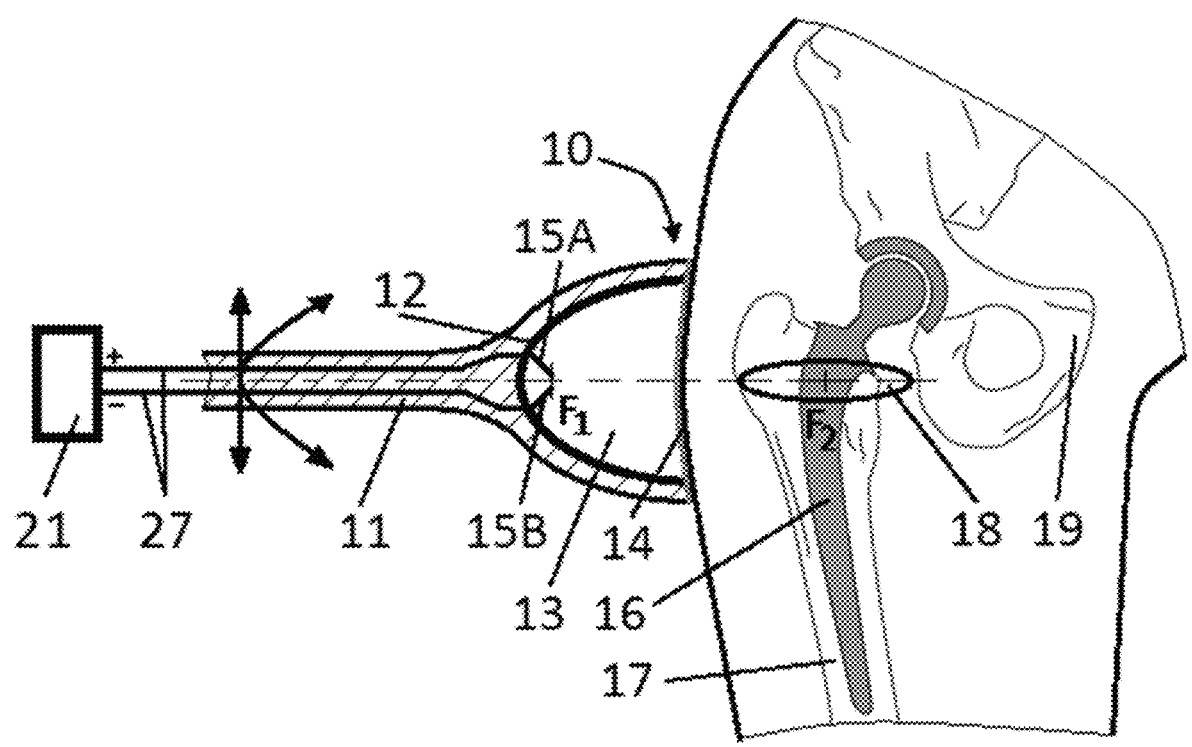
FIG. 1A is a schematic view of application of acoustic pressure shock waves to an infected hip prosthesis via electrohydraulic generators using spark gap high voltage discharges according to one embodiment of the present invention.
Figure 1B:
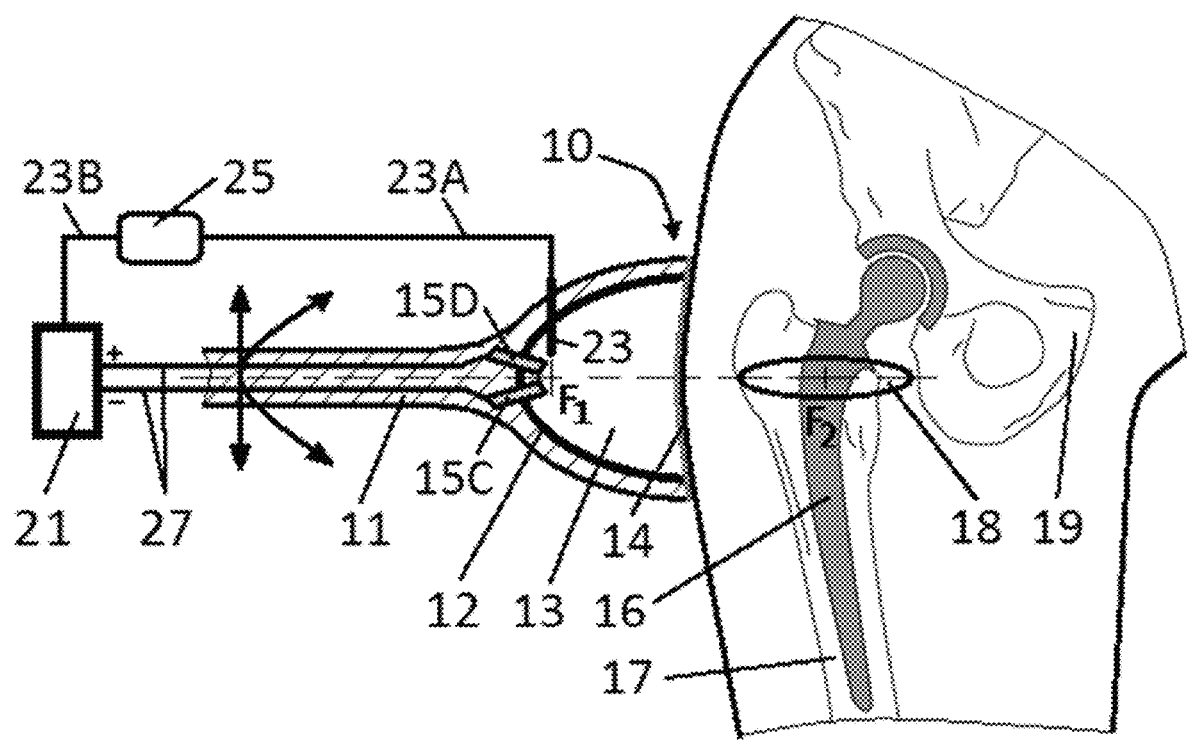
FIG. 1B is a schematic view of application of acoustic pressure shock waves to an infected hip prosthesis via electrohydraulic generators using one or multiple laser sources according to one embodiment of the present invention.
Figure 1C:
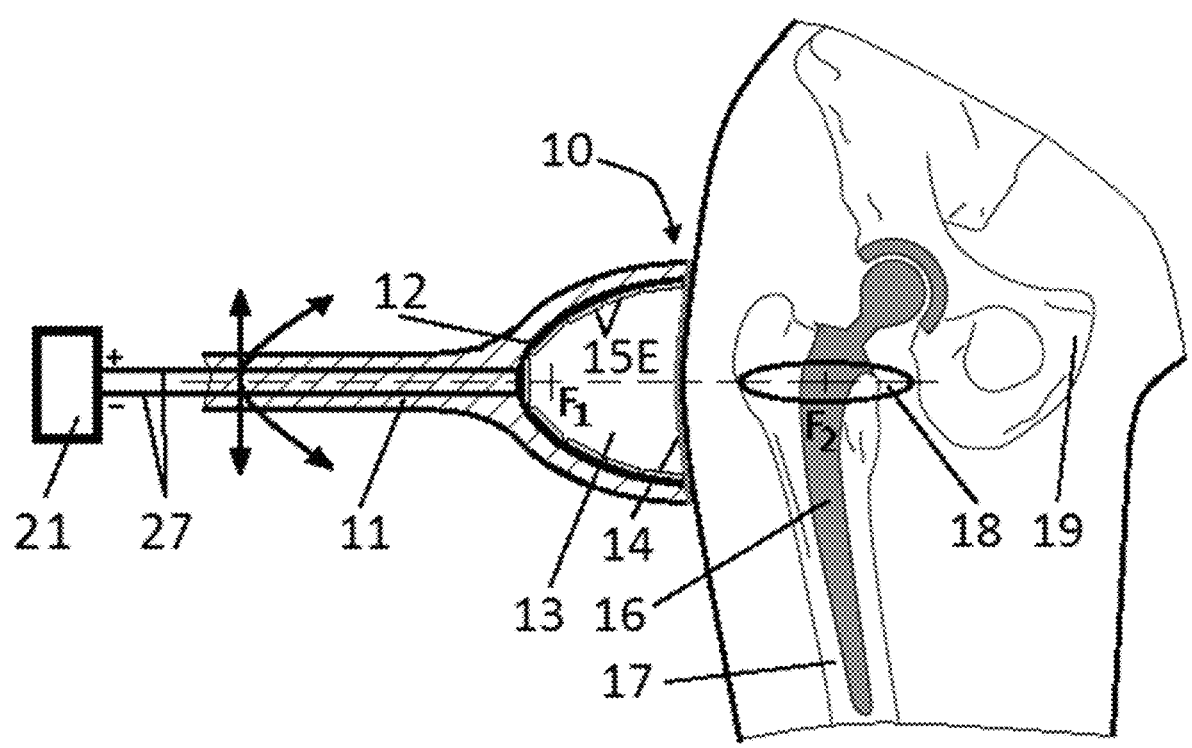
FIG. 1C is a schematic view of application of acoustic pressure shock waves to an infected hip prosthesis via piezoelectric generators using piezo crystals or piezo ceramics according to one embodiment of the present invention.
Figure 1D:
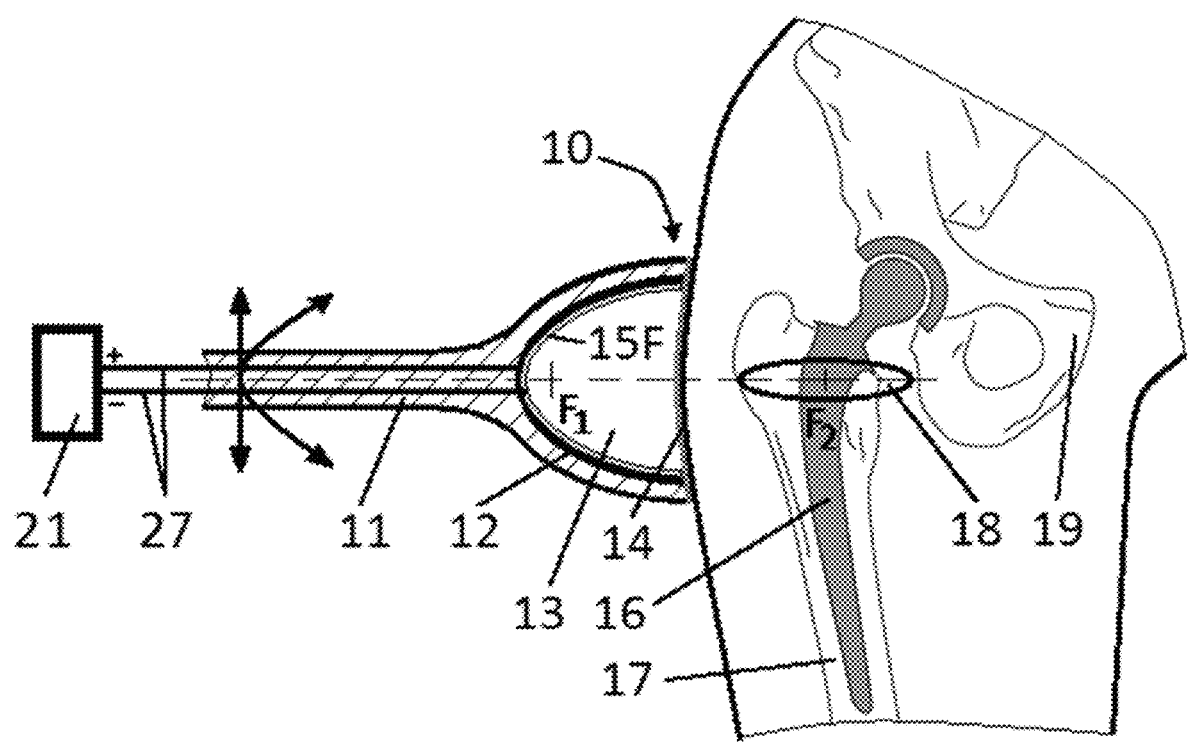
FIG. 1D is a schematic view of application of acoustic pressure shock waves to an infected hip prosthesis via electrohydraulic generators using piezo fibers according to one embodiment of the present invention.
Figure 1E:
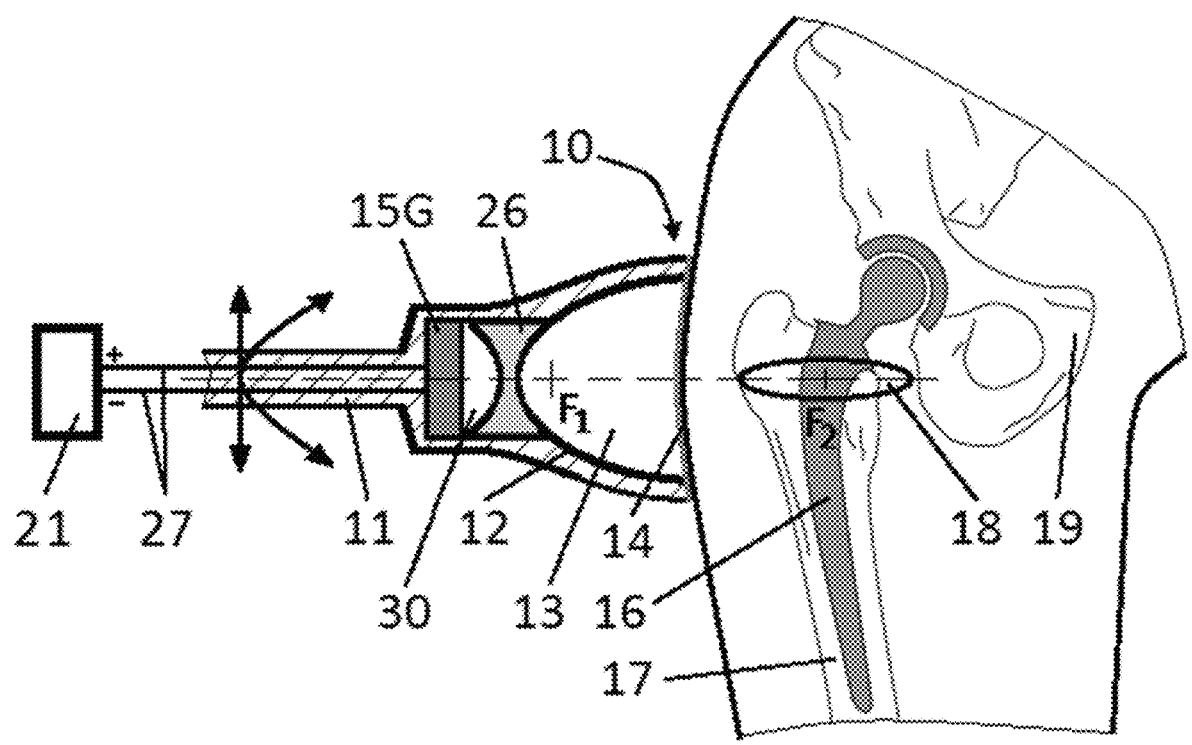
FIG. 1E is a schematic view of application of acoustic pressure shock waves to an infected hip prosthesis via electromagnetic generators using a flat coil and an acoustic lens according to one embodiment of the present invention.
Figure 1F:
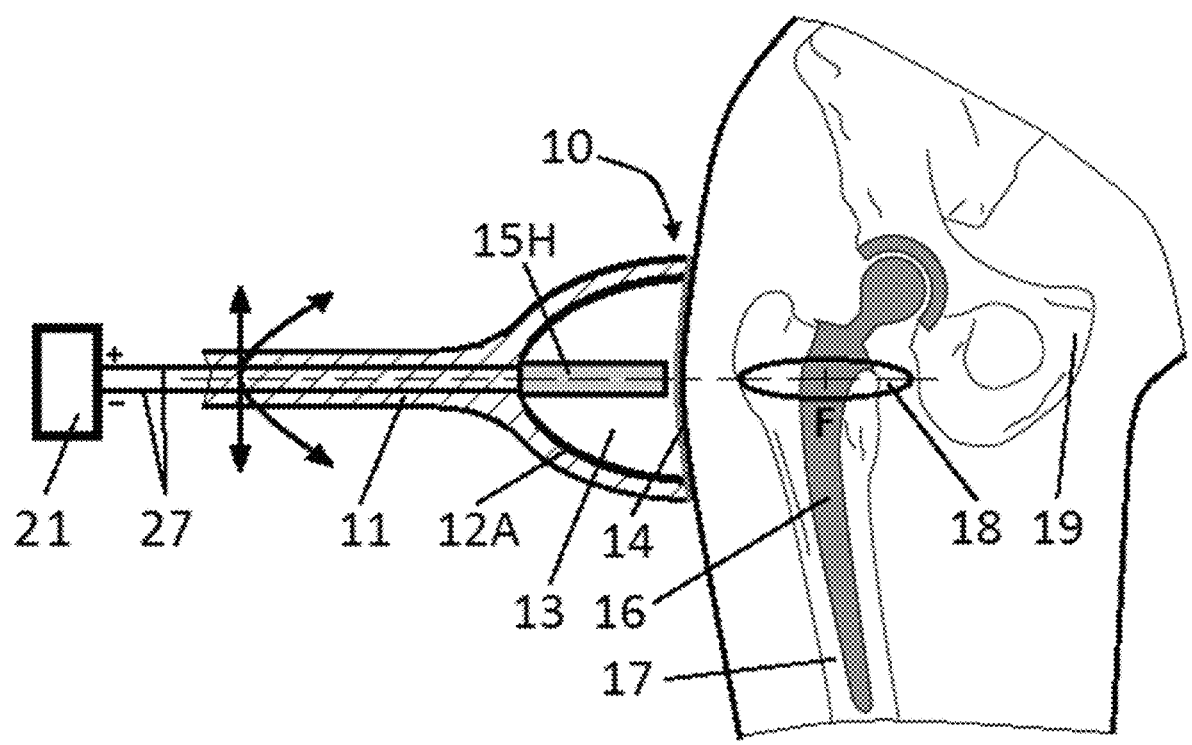
FIG. 1F is a schematic view of application of acoustic pressure shock waves to an infected hip prosthesis via electromagnetic generators using a cylindrical coil according to one embodiment of the present invention.

It is a further objective of the present inventions to provide different methods of generating focused, unfocused, planar, pseudo-planar or radial extracorporeal acoustic pressure shock waves for treating living tissue infections to produce tissue disinfection using specific devices that include an acoustic pressure shock wave generator or generators, such as for example:

electrohydraulic generators using spark gap high voltage discharges (as an example see FIG. 1A)
  electrohydraulic generators using one or multiple laser sources (as an example see FIG. 1B)
  piezoelectric generators using piezo crystals/piezo ceramics (as an example see FIG. 1C)
  piezoelectric generators using piezo fibers (as an example see FIG. 1D)
  electromagnetic generators using a flat coil and an acoustic lens (as an example see FIG. 1E)
  electromagnetic generators using a cylindrical coil (as an example see FIG. 1F)

It is a further objective of the present inventions to provide a means of controlling the energy and the penetrating depth of the extracorporeal acoustic pressure shock waves 29 (schematically shown in FIG. 2) used to treat living tissue infections to produce tissue disinfection via the amount of energy generated from the acoustic pressure shock wave generators, total number of the acoustic pressure shock waves/pulses, repetition frequency of the acoustic pressure shock waves 29 and special construction of the reflectors and membranes used in the acoustic pressure shock wave applicators.

It is a further objective of the present inventions to provide a variety of novel acoustic pressure shock wave applicator constructions for treating living tissue infections to produce tissue disinfection, determined by the number of reflectors housed in the applicator, the specific reflector shape, and their capability to guide or focus acoustic pressure shock waves 29 (schematically shown in FIG. 2) on a specific direction and for a predetermined penetration.

The acoustic pressure shock waves 29 (schematically shown in FIG. 2) are made up of frequencies ranging from 100 kHz to 20 MHz and will generally have a repetition rate of 1 to 20 Hz. The repetition rate is limited by cavitation, which represents the longest time segment (hundreds to thousands of microseconds) of the acoustic pressure shock waves. In order to not be negatively influenced by the new incoming acoustic pressure shock wave 29, the cavitation bubbles need sufficient time to grow to their maximum dimension and then collapse with high speed jets that have velocities of more than 100 m/s. Thus, the acoustic pressure shock waves 29 that have a high repetition rate can interfere with one another and negatively affect the cavitation period, hence reducing the desired effect of the acoustic pressure shock waves 29.

The inventions summarized below and defined by the enumerated claims are better understood by referring to the following detailed description, which is preferably read in conjunction with the accompanying drawing/figure. The detailed description of a particular embodiment, is set out to enable one to practice the invention, it is not intended to limit the enumerated claims, but to serve as a particular example thereof.

Also, the list of embodiments presented in this patent is not an exhaustive one and for those skilled in the art, new applications can be found within the scope of the invention.

Although not required, it is preferable in embodiments presented in this patent, for both animal and human treatments, to help ensure that the correct acoustic pressure shock wave applicator 10 and other necessary accessories (drapes, sleeves, pads, sterility barrier, coupling gel, drape, etc.) are used for a specific infection treatment, an authentication sequence process may be utilized by the control unit 28 (see FIG. 2) to confirm the use of correct acoustic pressure shock wave applicator 10, accessories, as presented in U.S. Pat. No. 8,961,441. The treatment parameters (input energy setting, frequency, total number of acoustic pressure shock waves 29 for the treatment session, etc.) can be introduced manually or via an ancillary data storage medium, as presented in the same U.S. Pat. No. 8,961,441.

Although significant advances were made for keeping operation rooms clean of pathogens, during surgeries for installation of implants or prosthesis inside the human and animal body, there is still a risk of pathogens to be trapped inside the body due to implant contamination and in time can produce the infection of the implant or prosthesis. If not treated properly, infections can cause sepsis and death. Some of small implants (heart and nerve stimulators, insulin pumps ports, cochlear implants, dental implants, etc.) can be easier to extract, treat infection and re-implant. However, there is still a risk of destroying the adjacent tissue, which can prevent re-implantation. Not to mention the physical and emotional toll that the patients need to go through. For larger implants (joint implants/prostheses for hip, knee, ankle, etc., artificial heart implants, orthopedic plates rods, screws, etc., breast implants, buttocks implants, intracorporeal drug delivery implants, etc.) they are very difficult to extract for replacement. Usually, the first line of defense is to treat with massive doses of antibiotics for at least 6 months to eradicate the infection. Even so, in many cases the infection cannot be eliminated and in the same time the implant/prosthesis 16 will not be able to proper integrate inside the tissue due to presence of macrophages, white cells and other immune system fighter cells at the interface between the implant/prosthesis 16 and tissue, producing the phenomenon called loosening of the implant/prosthesis 16 (lack of integration and adhesion with the surrounding tissue). To complicate the matter more, in time the pathogens as bacteria are able to develop complex structure called biofilms that offer excellent protection of individual bacterium integrated in them against immune system fighters or antibiotics.

The ability of acoustic pressure shock waves 29 (schematically shown in FIG. 2) to destroy planktonic bacteria or bacterial biofilms, viruses, funguses and other micro-organisms, gives a potential significant role in dealing with infections.

In the embodiments presented in FIG. 1A, FIG. 1B, FIG. 1C, FIG. 1D, FIG. 1E, and FIG. 1F an infected hip implant/prosthesis 16 is presented as an example on how acoustic pressure shock waves 29 (schematically shown in FIG. 2) are working in case of infections of such large implant or prosthesis, in general. The hip implant system contains the femoral part (implant/prosthesis 16) fixated into the femur 17 and acetabular part that is fixated inside the pelvic bone 19. In this embodiment the implant/prosthesis 16 from the femur 17 is infected at the interface/border with surrounding bone of the femur 17. The acoustic pressure shock wave applicator 10 has an ellipsoidal reflector 12 that resides inside the applicator body 11 and an applicator/coupling membrane 14. In this particular example, the acoustic pressure shock waves 29 (not shown in FIG. 1A, FIG. 1B, FIG. 1C, FIG. 1D, FIG. 1E, and FIG. 1F) are generated via different principles.

In FIG. 1A the acoustic pressure shock waves 29 (schematically shown in FIG. 2) are generated via high voltage discharge produced in between first electrode 15A and the second electrode 15B (electrohydraulic principle using spark gap high voltage discharges) in a fluid present inside the reflector cavity 13. The high voltage for the first electrode 15A and the second electrode 15B is provided by the power source 21 (included in control unit 28 from FIG. 2) via high voltage cable 27 (see also FIG. 2). The two electrodes 15A and 15B are positioned in the first focal point $F_1$ of the ellipsoidal reflector 12 and during their discharge they produce a plasma bubble that expands and collapse transforming the heat into kinetic energy in the form of acoustic pressure shock waves 29.

In FIG. 1B the acoustic pressure shock waves 29 (schematically shown in FIG. 2) are generated via one or multiple laser sources (electrohydraulic principle using one or multiple lasers sources). In this specific case the laser beams produced by first incased laser 15C and the second incased laser 15D in a fluid present inside the reflector cavity 13 generate the acoustic pressure shock waves 29. The high voltage for the first incased laser 15C and the second incased laser 15D is provided by the power source 21 (included in control unit 28 from FIG. 2) via high voltage cable 27 (see also FIG. 2). The two laser sources are positioned in such way to intersect their beams in the first focal point $F_1$ of the ellipsoidal reflector 12 in order to produce a plasma bubble that expands and collapse transforming the heat into kinetic energy in the form of acoustic pressure shock waves 29. FIG. 1B includes a means of monitoring the system performance by measuring the reaction temperature of the plasma bubble collapse using a method of optical fiber thermometry. An optical fiber tube assembly 23 extends into the $F_1$ region of the ellipsoidal reflector 12. The optical fiber tube assembly 23 transmits (via optical fiber 23A) specific spectral frequencies created from the sonoluminescence of the plasma reaction in the fluid present inside the reflector cavity 13 to the spectral analyzer 25. The loop is closed via feedback cable 23B that connects the spectral analyzer 25 with the power source 21. Basically, the spectral analysis provided by the spectral analyzer 25 is used to adjust accordingly the power generated by the power source 21, to ensure a proper laser discharge for the incased lasers 15C and 15D.

In FIG. 1C the acoustic pressure shock waves 29 (schematically shown in FIG. 2) are generated via piezo crystals/piezo ceramics 15E (piezoelectric principle using piezo crystals/piezo ceramics). In this case the internal generation of a mechanical strain resulting from an applied electrical field to the piezo crystals/piezo ceramics 15E that are uniformly placed on the ellipsoidal reflector 12 generate in a fluid present inside the reflector cavity 13 the acoustic pressure shock waves 29. The electrical field for the piezo crystals/piezo ceramics 15E is provided by the power source 21 (included in control unit 28 from FIG. 2) via high voltage cable 27 (see also FIG. 2).

Due to the parallelepiped geometry of the piezo crystals/piezo ceramics 15E, they are not confirming very well to the ellipsoidal reflector 12, which can create problems with focusing and to overcome this issue piezo fibers can be used as presented in FIG. 1D. The piezo fibers can be integrated in a composite material with their longitudinal axis perpendicular to a solid surface as the ellipsoidal reflector 12, thus forming a piezo fiber reflector 15F. The advantage of the piezo fibers when compared to the piezo crystals/piezo ceramics 15E is their smaller dimension and cylindrical geometry that allows them to confirm significantly better to the ellipsoidal geometry. Furthermore, the contacting of the piezo fibers may be realized by a common electrically conductive layer according to the interconnection requirements. Hence, the complex interconnection of a multitude of piezo crystals/piezo ceramics 15E (as presented in FIG. 1C) is no longer required. When an electrical field is provided by the power source 21 (included in control unit 28 from FIG. 2) via high voltage cable 27 (see also FIG. 2) to the piezo fiber reflector 15F the piezo electric fiber will stretch in unison mainly in their lengthwise direction, which will create acoustic pressure shock waves 29 (schematically shown in FIG. 2). This represents the piezoelectric principle using piezo fibers to produce acoustic pressure shock waves 29.

In FIG. 1E the acoustic pressure shock waves 29 (schematically shown in FIG. 2) are generated via electromagnetic flat coil and plate assembly 15G and an acoustic lens 26 (electromagnetic principle using a flat coil and an acoustic lens). In this case, an electromagnetic flat coil is placed in close proximity to a metal plate that acts as an acoustic source and thus the electromagnetic flat coil and plate assembly 15G presented in FIG. 1E is created. When the electromagnetic flat coil is excited by a short electrical pulse provided by the power source 21 (included in control unit 28 from FIG. 2) via high voltage cable 27 (see also FIG. 2), the plate experiences a repulsive force and this is used to generate an acoustic wave. Due to the fact that the metal plate is flat, the resulting acoustic wave is a planar wave (not shown in FIG. 1E) moving in the fluid-filled cavity 30 towards the acoustic lens 26 that is focusing the planar wave and thus creating acoustic pressure shock waves 29 that are focused towards the targeted area via the fluid-filled reflector cavity 13. The focusing effect of the acoustic lens 26 is given by its shape, which is a portion of an ellipsoidal surface.

In FIG. 1F the acoustic pressure shock waves 29 (schematically shown in FIG. 2) are generated via electromagnetic cylindrical coil and tube plate assembly 15H (electromagnetic principle using a cylindrical coil). In this case, an electromagnetic cylindrical coil is excited by a short electrical pulse provided by the power source 21 (included in control unit 28 from FIG. 2) via high voltage cable 27 (see also FIG. 2), and the plate is in the shape of a tube (thus creating an electromagnetic cylindrical coil and tube plate assembly 15H), which will results in a cylindrical wave (not shown in FIG. 1F) that can be focused by a parabolic reflector 12A towards its focus point F in the targeted area via the fluid-filled reflector cavity 13.

For FIG. 1A, FIG. 1B, FIG. 1C, and FIG. 1D the acoustic pressure shock waves 29 (schematically shown in FIG. 2) produced inside ellipsoidal reflector 12 are then reflected/focused by the ellipsoidal reflector 12 towards the second focal point $F_2$ of the ellipsoid. In fact the ellipsoidal reflector 12 in this case is only a half of an ellipsoid, in order to allow the transmission of the acoustic pressure shock waves 29 deep inside the body, where the second focal point $F_2$ is preferably found. In this way the other half of the ellipsoid is missing to allow the placement of the body in contact (via applicator/coupling membrane 14) with the acoustic pressure shock wave applicator 10. For FIG. 1E the acoustic pressure shock waves 29 are focused towards the targeted area by the acoustic lens 26 (it has the shape of a portion of an ellipsoidal surface) and for FIG. 1F the focusing is realized by the parabolic reflector 12A. Due to the fact that different pressures fronts (direct or reflected) reach the second focal point $F_2$ (for ellipsoidal geometries) or focus point F (for parabolic geometries) with certain small time differences, the acoustic pressure shock waves 29 are in reality concentrated or focused on a three-dimensional space around second focal point $F_2$/focus point F, which is called focal volume 18. Inside the focal volume 18 are found the highest pressure values for each acoustic pressure shock wave 29, which means that is preferable to position the targeted area for the treatment in such way to intersect the focal volume 18 and if possible centered on the second focal point $F_2$ (for ellipsoidal geometries) or on the focus point F (for parabolic geometries). In order to be effective against infection, the acoustic pressure shock wave applicator 10 and its components are designed in such way to ensure that the focal volume 18 (where acoustic pressure shock waves 29 are focused) is positioned deep enough to allow its overlap with the bone/prostheses interface, as presented in FIG. 1A, FIG. 1B, FIG. 1C, FIG. 1D, FIG. 1E, and FIG. 1F.

The penetration inside the human body and the geometry of the focal volume 18 are dictated by energy setting for acoustic pressure shock waves 29 (schematically shown in FIG. 2) or input energy, applicator/coupling membrane 14 geometry and dimensional characteristics of the ellipsoidal reflector 12 (dictated by the ratio of the large semi-axis and small semi-axis of the ellipsoid, and by its aperture defined as the dimension of the opening of the ellipsoidal reflector 12). Thus the ellipsoidal reflector 12 needs to be deep enough to allow a deep second focal point $F_2$ inside the body that can be positioned on the implant/prosthesis 16. The deep ellipsoidal reflector 12 is also advantageous due to the fact that the larger the focusing area of the ellipsoidal reflector 12, the larger the focal volume will be and the energy associated with it, which is deposited into the targeted area. In general to accomplish that, the ratio of the large semi-axis and small semi-axis of the ellipsoid (the small axis of the ellipsoid 44 and the large axis of the ellipsoid 46 are identified in FIG. 4A, their dimension is given by their intersection with the ellipsoid, and their semi-axis value being defined as half of their respective full dimensions) preferably have values larger than 1.6. For superficial treatments the same ratio is preferably in between 1.1 and 1.6.

For the parabolic reflector 12A (presented in FIG. 1F) its geometry should be chosen in such way that the focus point of the parabola F should be positioned deep enough to allow its overlap with the bone/prostheses interface. That means that the focal length (defined as distance between the bottom of the reflector where the parabola is most sharply curved and the focus point of the parabola F—see FIG. 1F) for the parabolic reflector 12A should be at least 10 cm (depending on the position of the infected prosthesis/implant inside the human/animal body).

The fluid present inside the reflector cavity 13 in between ellipsoidal reflector 12 and applicator/coupling membrane 14 (for embodiments presented in FIG. 1A and FIG. 1B), is preferably a mixture of water with proprietary substance/particles/catalysts that promote a better discharge and recombination of free radicals back to water form, as presented in U.S. Pat. Nos. 6,080,119 and 9,198,825. It will be appreciated that other fluids may also be employed which those of ordinary skill art appreciate to provide suitable acoustic properties for conducting generated shock wave. It will be appreciated that other embodiments presented in FIG. 1C, FIG. 1D, FIG. 1E and FIG. 1F only a degassed fluid is preferably necessary to be placed in cavity 13 in between ellipsoidal reflector 12 and applicator/coupling membrane 14. Furthermore, for all embodiments presented in FIG. 1A, FIG. 1B, FIG. 1C, FIG. 1D, FIG. 1E, and FIG. 1F, the acoustic properties of the fluid present in between ellipsoidal reflector 12 and applicator/coupling membrane 14 are preferably similar to the acoustic properties of human and animal bodies, which allow transmission of the acoustic pressure shock waves 29 (schematically shown in FIG. 2) seamlessly in between the acoustic pressure shock wave applicator 10 and human or animal bodies.

It is interesting to note that fragments of bacteria, viruses, micro-organisms that were destroyed by the acoustic pressure shock waves 29 (schematically showed in FIG. 2), may be able to trigger the body's immune system to eradicate the pathogens still left in the body after an acoustic pressure shock wave treatment, which can enhance the effects provided by the acoustic pressure shock waves 29. This potential enhancement is applicable to all embodiments presented herein.

The quantity of energy deposited inside the tissue during one treatment session by the acoustic pressure shock waves 29 (schematically shown in FIG. 2) is dependent on the dosage, which includes the following elements:

Input energy delivered by the control unit 28 (showed in FIG. 2) provided by the power source 21 via cable 27 (see FIG. 1A, FIG. 1B, FIG. 1C, FIG. 1D, FIG. 1E, and FIG. 1F)

Output energy inside the tissue of each acoustic pressure shock wave 29, known as energy flux density or instantaneous intensity at a particular point inside the focal volume 18

Frequency of repetition for acoustic pressure shock waves 29, defined as number of acoustic pressure shock waves 29 per each second Total amount of pressure shock waves 29 delivered in one treatment The amount of energy deposited into the treatment area needs to be sufficient to allow the disruption of the biofilms and killing of pathogens. For that the voltage provided by the power source 21 via cable 27 should be in the range of 1 to 30 kV for the embodiment presented in FIG. 1A, FIG. 1B, FIG. 1C, FIG. 1D, FIG. 1E, and FIG. 1F based on the reflective surface of the ellipsoidal reflector 12 incorporated into construction of the acoustic pressure shock wave applicator 10. Basically, the smaller the reflective surface of the ellipsoidal reflector 12/parabolic reflector 12A (for example small hand-held acoustic pressure shock wave applicators 10 that have small apertures of approximately 30 to 120 mm for the ellipsoidal reflector 12/ parabolic reflector 12A) the larger the voltage discharge (about 10 to 30 kV) that is preferably used. For large ellipsoidal reflectors 12/parabolic reflectors 12A that are used in acoustic pressure shock wave applicators 10, which are not hand-held (they require dedicated positioning arms integrated with the acoustic pressure shock wave system and are more in the realm of lithotripsy type of applicators with apertures for the ellipsoidal reflector 12 larger than 120 mm) the voltage in the range of about 1 to 20 kV will be used.

In the embodiment from FIG. 1A, FIG. 1B, FIG. 1C, FIG. 1D, FIG. 1E, and FIG. 1F, due to the fact that hard materials have the tendency to reflect acoustic pressure shock waves 29 (schematically shown in FIG. 2) compared with the surrounding soft tissue, on the pathway from acoustic pressure shock wave applicator 10 to the targeted area there will be reflections of the acoustic pressure shock waves 29 at the bone/soft tissue interface and also at the bone/implant interface. This occurs due to different acoustic properties of soft tissue, bone and metals that are used in the construction of the implant/prosthesis 16. In order to overcome these loses, the acoustic pressure shock waves 29 will need to be strong enough to allow the transmitted component of the acoustic pressure shock waves 29 at these interfaces to have sufficient energy at the targeted area (output energy) to destroy the biofilm and pathogens that produce infection and loosening of the implant/prosthesis 16. For that treatment, energy flux density of each acoustic pressure shock wave 29 around second focal point $F_2$ (FIG. 1A, FIG. 1B, FIG. 1C, FIG. 1D, and FIG. 1E) or focus point F (FIG. 1F) inside the focal volume 18 is preferably in the range of 0.10 to 1.00 mJ/mm². However, depending on the characteristics of each device, the energy flux density is carefully chosen for each specific application in such way to not produce any damage to the targeted tissue.

For killing pathogens from an infected area, cavitation plays a primary role in destroying the outer membrane of the pathogens. In order to have maximum potential for the cavitation phase of the acoustic pressure shock waves 29 (schematically shown in FIG. 2), the repetition rate or frequency of acoustic pressure shock waves 29 is recommended to be in the range of 1 to 8 Hz. To not be negatively influenced by the new coming acoustic pressure wave 29, the cavitation bubbles need sufficient time to grow to their maximum dimension and then collapse with high speed jets that have velocities of more than 100 m/s.

The total amount of acoustic pressure shock waves 29 (schematically shown in FIG. 2) is dependent on the situation from the infected area. In order to kill planktonic bacteria and other pathogens is easier when compared to biofilms, which preferably will use a total number of acoustic pressure shock waves 29 of between about 1,000 and about 10,000, depending on the type of pathogen. For destroying biofilms and then kill the pathogens, the total amount of acoustic pressure shock waves 29 is preferably in between about 4,000 to about 20,000. If the large amount of acoustic pressure shock waves 29 is not feasible to be accomplished in a single session/treatment, then multiple sessions may be applied and spread over a certain period of time, such as twice a day or every day or every other day. In general, a maximum of seven (7) to ten (10) sessions are preferable for application, followed by a resting period of few days to few weeks. During the acoustic pressure shock wave treatment the antibiotics preferably continue to be administered, to enhance the effects of the acoustic pressure shock wave treatment. If infection is not completely eradicated with the first round of sessions, after recommended resting period, the acoustic pressure shock waves 29 can be administered again, without producing any side effects.

Moving up and down and around the leg (see arrows from FIG. 1A, FIG. 1B, FIG. 1C, FIG. 1D, FIG. 1E, and FIG. 1F) under visualization systems guidance will allow the proper coverage of all infected interface between the femur 17 and implant/prosthesis 16. The correct positioning of the focal volume 18 in the targeted area can be accomplished with different visualization systems available in hospitals or ambulatory centers as ultrasound, fluoroscopic devices, etc., devices that are not subject of this invention.

In order to transmit acoustic pressure shock waves 29 (schematically shown in FIG. 2) inside the body, in between the applicator/coupling membrane 14 of the acoustic pressure shock wave applicator 10 and the skin of the patient, an acoustic coupling gel (ultrasound gel) must be used (not shown in FIG. 1A, FIG. 1B, FIG. 1C, FIG. 1D, FIG. 1E, and FIG. 1F). The gel has the same acoustic properties as animal/human soft tissue or skin and matches the acoustic impedance of the fluid enclosed inside the reflector cavity 13 of the acoustic pressure shock wave applicator 10. In this way the transmission of the acoustic pressure shock waves 29 is done without any losses. Caution must be taken, to not have air bubbles trapped inside the acoustic coupling gel, based on the fact that air can significant interfere with the propagation and potency/energy of the acoustic pressure shock waves 29, due to significant acoustic mismatch.

Figure 4A:
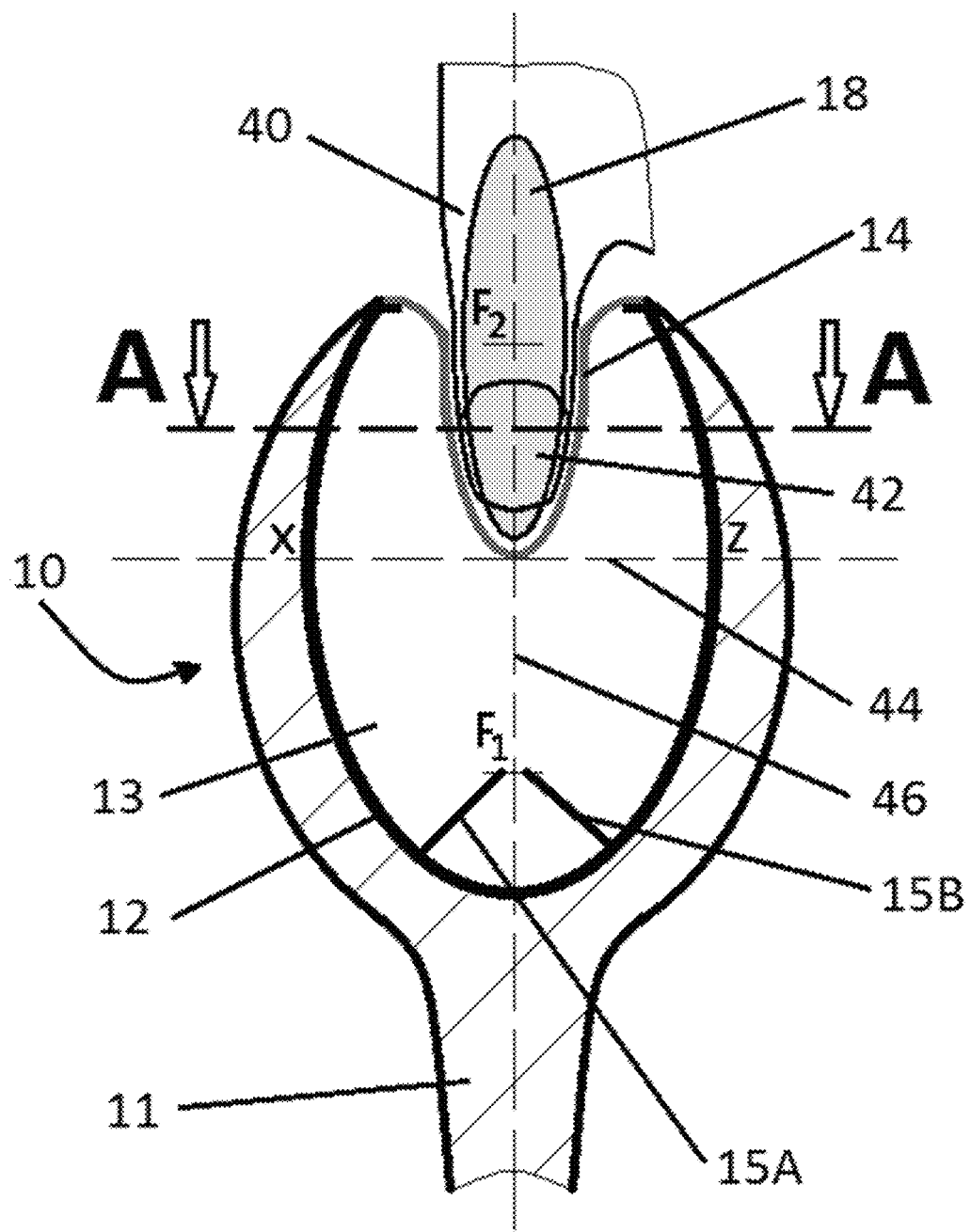
FIG. 4A is a cross-sectional side schematic view of an applicator receiving an infected toe inside a reflector for treatment with acoustic pressure shock waves according to one embodiment of the present invention.

Although the examples from FIG. 1A, FIG. 1B, FIG. 1C, FIG. 1D, FIG. 1E, and FIG. 1F refer to the hip prosthesis, the same parameters, setting and approach can be done for other implants as knee, ankle, shoulder, phalangeal, foot prostheses or for artificial heart implants, orthopedic plates rods, screws, nerve stimulators, insulin pumps ports, cochlear implants, dental implants, intracorporeal drug delivery implants, etc Similar to what was presented for the embodiment from FIG. 1A, FIG. 1B, FIG. 1C, FIG. 1D, FIG. 1E, and FIG. 1F (hard tissue infections), for soft tissue disinfection (for example breast implants, facial implants, buttocks implants, skin infections, subcutaneous infections etc. for humans or mastitis, skin infections, subcutaneous infections, etc. for animals) using acoustic pressure shock waves 29 (schematically shown in FIG. 2) the penetration and amount of energy deposited inside the soft tissue is also dependent on ellipsoidal reflector 12 construction (ratio between the large semi-axis 46 and small semi-axis 44, identified in FIG. 4A, and ellipsoidal reflector 12 aperture), focus length for parabolic reflector 12A, energy setting for control unit 28 (energy input), energy flux density inside the focal volume 18 (energy output), total amount of acoustic pressure shock waves 29 and the geometry of the applicator/coupling membrane 14. The focal volume 18 is preferably also positioned inside the body and relatively to the patient's skin in such way that the treatment targeted area to be able to intersect the focal volume 18 in close vicinity of the second focal point $F_2$ (for embodiments presented in FIG. 1A, FIG. 1B, FIG. 1C, FIG. 1D, and FIG. 1E) or the focus point F (for embodiment presented in FIG. 1F).

Thus for treatment of soft tissue infection, it is preferable to use discharge voltages between about 18 and about 30 kV provided by power source 21 via cable 27 as presented in FIG. 1A, FIG. 1B, FIG. 1C, FIG. 1D, FIG. 1E, and FIG. 1F. In general for the flexibility of the treatment and ease-of-use for the operator/user, hand-held acoustic pressure shock wave applicators 10 may preferably be employed with apertures of about 30 to about 120 mm for the ellipsoidal reflector 12.

For treating soft tissue infections, the energy flux density inside the focal volume 18 for each acoustic pressure shock wave 29 (schematically shown in FIG. 2) is preferably in the range of about 0.10 to about 0.60 $mJ/mm^2$, to not affect negatively the functionality of the respective soft tissue. A preferable frequency range for treating soft tissue is about 1 to about 8 Hz and the total amount of acoustic pressure shock waves 29 delivered to the targeted area and possible number of sessions/resting periods preferably follow the same recommended numbers and as for the hard tissue infections, as presented above for the embodiment from FIG. 1A, FIG. 1B, FIG. 1C, FIG. 1D, FIG. 1E, and FIG. 1F. For soft tissue infections, based on the size and position of the infected area, the acoustic pressure shock wave applicator 10 can be moved in any direction to completely cover the whole affected area, as depicted by the arrows from FIG. 1A, FIG. 1B, FIG. 1C, FIG. 1D, FIG. 1E, and FIG. 1F.

Figure 2:
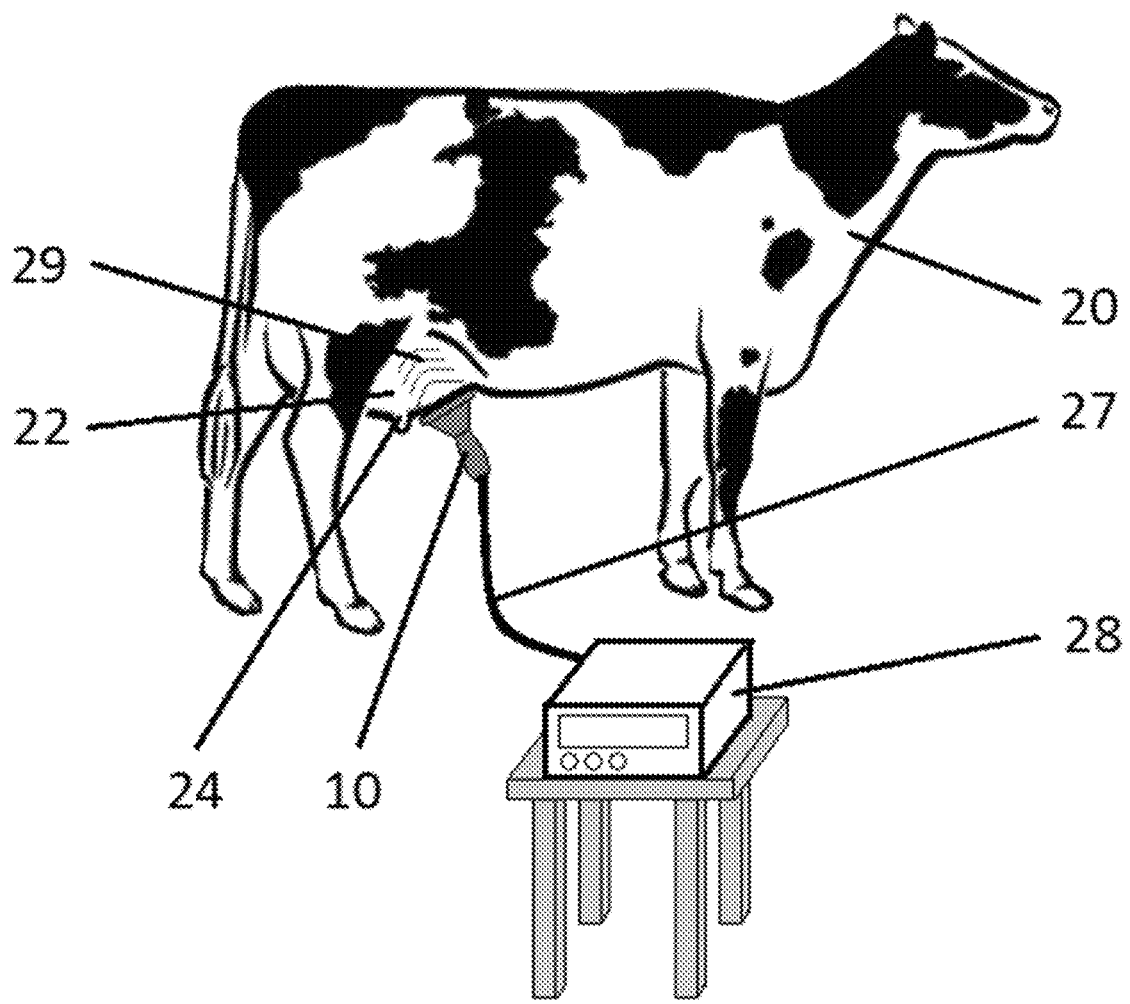
FIG. 2 is a schematic view of application of acoustic pressure shock waves to the mastitis affected tissue according to one embodiment of the present invention.
Figure 3:
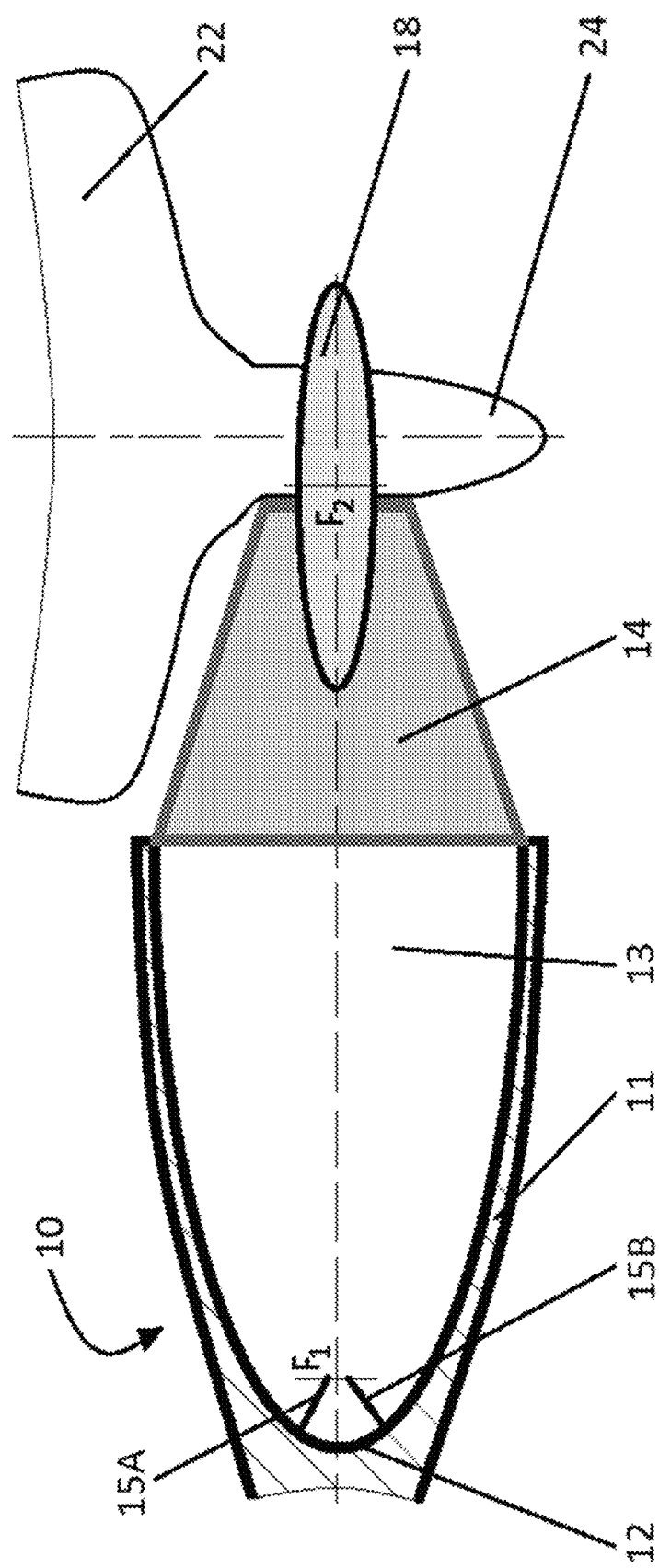
FIG. 3 is a schematic view of an applicator used to deliver acoustic pressure shock waves to a teat affected by mastitis according to one embodiment of the present invention.

As a practical example for the treatment of soft tissue infection, the embodiment from FIG. 2 presents the action of acoustic pressure shock waves 29 on the udder 22 for a cow 20 affected by mastitis and the embodiment from FIG. 3 shows the treatment of a teat 24 infected with mastitis.

In FIG. 2, the cow 20 has a mastitic infection of the udder 22. The treatment with acoustic pressure shock waves 29 is performed on the udder 22, using an acoustic pressure shock wave applicator 10. Due to the fact that the acoustic pressure shock waves 29 can penetrate any type of tissue (soft tissue with inflammation, normal tissue, scar tissue, milk glands) and any milk accumulated into the udder, the propagation of the acoustic pressure shock waves 29 can be accomplished without any restriction in the whole udder 22. To cover all the infection, the acoustic pressure shock wave applicator 10, can be moved in any direction around the udder 22 in order to focus the acoustic pressure shock waves 29 in the targeted area for treatment. It is important that the movement of the acoustic pressure shock wave applicator 10 to be done in such way "to paint" all the targeted area. The treatment can be done for superficial penetrations (see FIG. 8), medium penetrations (see FIG. 9) and deep penetrations (see FIG. 10).

For proper transmission of acoustic pressure shock waves 29 (schematically shown in FIG. 2) sufficient acoustic transmission couplings gel (not shown in FIG. 2) must be used in between the udder 22 that needs to be treated and the applicator/coupling membrane 14 (depicted in FIG. 1A, FIG. 1B, FIG. 1C, FIG. 1D, FIG. 1E, and FIG. 1F and not specifically shown in FIG. 2), which will acoustically couple the udder 22 with applicator/coupling membrane 14. For that the udder 22 is first covered with acoustic transmission coupling gel (not shown in FIG. 2). Then the acoustic pressure shock wave applicator 10 is positioned in the required location against the udder 22 and with the acoustic transmission coupling gel in between. The acoustic pressure shook wave applicator 10 has a cable 27 to connect with the control unit 28 and the power source 21 (not specifically shown in FIG. 2, but illustrated in FIG. 1A, FIG. 1B, FIG. 1C, FIG. 1D, FIG. 1E, and FIG. 1F) integrated inside the control unit 28. The control unit 28 is an electromechanical device with integrated software, which is activating and controls the functionality of the acoustic pressure shock wave applicator 10.

The embodiment presented in FIG. 3 shows the specific treatment of a teat 24 from a cow 20 (see FIG. 2) infected with mastitis. In this case the acoustic pressure shock wave applicator 10 is dimensionally designed to allow the proper treatment of the teat 24. To accomplish that the applicator/coupling membrane 14 needs to have sufficient height to allow the reach of the teat 24, without being impeded by the presence of the udder 22. For proper transmission of acoustic pressure shock waves 29 (schematically shown in FIG. 2) sufficient acoustic transmission coupling gel (not shown in FIG. 3) must be used in between the teat 24 that needs to be treated and the applicator/coupling membrane 14, which will acoustically couple the teat 24 with applicator/coupling membrane 14. The focal volume 18 can be oriented relatively to the teat 24 in such way that the second focal point $F_2$ is positioned on the superficial region of the teat 24, as presented in FIG. 3. In this way the affected wall of the teat 24, where the mastitic pathogen is expected to be lodged in, will have the largest energy output focused on it. However, due to small diametric dimension of the teat 24, the hand-held acoustic pressure shock wave applicators 10 can be designed to have the geometry of the ellipsoidal reflector 12 in such way that the focal volume 18 can cover entirely the teat 24 (as presented in FIG. 3), which will expose the teat 24 to large output energy in each position of the acoustic pressure shock wave applicator 10. The acoustic pressure shock wave applicator 10 can be moved up/down and around the teat 24 to cover completely the infected area.

The treatment regimen applied for cow mastitis is preferably dependent on the stage of the disease. Usually, the mastitis is detected and graded by counting the somatic cells from the milk. The somatic cell count (SCC) is given in its majority by the leukocytes (white blood cells), which increase in number due to an immune response to a mastitis-causing-pathogen. A small percentage of SCC is given by epithelial cells shed from inside the udder 22 when an infection occurs. Practically, an SCC of 100,000 or less indicates the presence of subclinical mastitis, where there are no significant production losses. A threshold SCC of 200,000 would determine whether a cow 20 is infected with mastitis. Cows 20 with a result of greater than 200,000 are highly likely to be infected on at least one quarter/teat 24 and cows 20 infected with significant pathogens have an SCC of 300,000 or greater.

Based on these generally industry accepted thresholds for somatic cell count (SCC), for cows 20 that have SCC of 500,000 or higher (practically SCC is unreadable due to actual coagulation of the milk) the regimen for treating one or more quarters/teats 24 (as presented for the embodiment from FIG. 3) is preferably to have the control unit 28 (shown in FIG. 2) delivering high input energy (high energy setting), which can provide energy flux densities in the targeted tissue of 0.20 to 0.60 mJ/mm$^2$. The total number of acoustic pressure shock waves 29 (schematically shown in FIG. 2) delivered in one session is preferably in between about 1,000 to about 3,000 per teat 24 treated. Frequency for acoustic pressure shock waves 29 is preferably about 1 to about 8 Hz. The treatment regimen for an infected teat 24 preferably includes multiple sessions with at least four sessions in the first two days (one in the morning and one in the evening of each day), followed by one or two sessions per day for at least four more days, to be able to sustain the total clearing of the infection. If more sessions are needed, based on severity of the individual case of mastitis, the treatment is preferably continued for sufficient number of days until the infection is cleared.

For the same somatic cell count (SCC) of 500,000, if the infection goes into the udder 22 (as presented for the embodiment from FIG. 2), the energy flux density in the targeted tissue for the treatment is preferably about 0.20 to about 0.60 mJ/mm$^2$, with a total number of acoustic pressure shock waves 29 (schematically shown in FIG. 2) delivered in one session in between about 1,500 to about 10,000 per udder 22 treated, depending on the size of the affected area. The total number of acoustic pressure shock waves 29 delivered in one session to treat the udder 22 can be also calculated function of the udder area that needs to be treated. At least 32 acoustic pressure shock waves 29 per centimeter square area of the udder 22 is preferably delivered to treat cows 20 affected by mastitis. Frequency for acoustic pressure shock waves 29 is preferably about 1 to about 8 Hz. The treatment regimen for an infected udder 22 preferably includes multiple sessions with at least four sessions in the first two days (one in the morning and one in the evening of each day), followed by one or two sessions per day for at least seven more days, to be able to sustain the total clearing of the infection. If more sessions are needed, based on severity of the individual case of mastitis, the treatment is preferably continued for sufficient number of days until the infection is cleared.

For a somatic cell count (SCC) in between 50,000 to 500,000, if the infection is affecting one or more quarters/teats 24 (as presented for the embodiment from FIG. 3), the energy flux density in the targeted tissue for the treatment is preferably about 0.10 to about 0.50 mJ/mm$^2$, with a total number of acoustic pressure shock waves 29 (schematically shown in FIG. 2) delivered in one session in between about 1,000 to about 3,000 per teat 24 treated. Frequency for acoustic pressure shock waves 29 is preferably about 1 to about 8 Hz. The treatment regimen for an infected teat 24 preferably includes multiple sessions with at least four sessions in the first two days (one in the morning and one in the evening of each day), followed by one or two sessions per day for at least three more days, to be able to sustain the total clearing of the infection. If more sessions are needed, based on severity of the individual case of mastitis, the treatment is preferably continued for sufficient number of days until the infection is cleared.

For a somatic cell count (SCC) in between 50,000 to 500,000, if the infection is affecting the udder 22 (as presented for the embodiment from FIG. 2), the energy flux density in the targeted tissue for the treatment is preferably 0.10 to 0.50 mJ/mm$^2$, with a total number of acoustic pressure shock waves 29 (schematically shown in FIG. 2) delivered in one session in between 1,500 to 10,000 per udder 22 treated, depending on the size of the affected area. The total number of acoustic pressure shock waves 29 delivered in one session to treat the udder 22 can be also calculated function of the udder area that needs to be treated. For that a number of at least 32 acoustic pressure shock waves 29 per centimeter square area of the udder 22 is preferably delivered to these cows 20 affected by mastitis. Frequency for acoustic pressure shock waves 29 is preferably 1 to 8 Hz. The treatment regimen for an infected udder 22 preferably includes multiple sessions with at least four sessions in the first two days (one in the morning and one in the evening of each day), followed by one or two sessions per day for at least four more days, to be able to sustain the total clearing of the infection. If more sessions are needed, based on severity of the individual case of mastitis, the treatment is preferably continued for sufficient number of days until the infection is cleared.

As a prophylactic treatment for a teat 24 (as presented for the embodiment from FIG. 3), for cows 20 with somatic cell count (SCC) lower than 50,000, the energy flux density in the targeted tissue for the treatment is preferably about 0.10 to about 0.40 mJ/mm$^2$, with a total number of acoustic pressure shock waves 29 (schematically shown in FIG. 2) delivered in one session in between about 1,000 to about 3,000 per teat 24 treated for these cows 20 that were affected by mastitis in the past and prevention of reoccurrence is necessary. Frequency for acoustic pressure shock waves 29 is preferably about 1 to about 8 Hz. The treatment regimen for a teat 24 preferably includes multiple sessions with at least four sessions (one in the morning and one in the evening for two consecutive days) for week one, followed by similar four sessions in two consecutive days per week for at least two more weeks, with at least one week interval in between treatment days.

For a somatic cell count (SCC) less than 50,000, for prophylactic treatment of the udder 22 (as presented for the embodiment from FIG. 2), the energy flux density in the targeted tissue for the treatment is preferably about 0.10 to about 0.40 mJ/mm$^2$, with a total number of acoustic pressure shock waves 29 (schematically shown in FIG. 2) delivered in one session in between 1,500 to 5,000 per udder 22 treated, depending on the size of the targeted area of the udder 22 that was affected by mastitis in the past and prevention of reoccurrence is necessary. The total number of acoustic pressure shock waves 29 delivered in one session to treat prophylactic the udder 22 can be also calculated function of the udder area that needs to be treated. For that a number of at least 16 acoustic pressure shock waves 29 per centimeter square area of the udder 22 is preferably delivered to these cows 20 that were affected by mastitis in the past and prevention of reoccurrence is necessary. Frequency for acoustic pressure shock waves 29 is preferably about 1 to about 8 Hz. The treatment regimen for an udder 22 preferably includes multiple sessions with at least four sessions (one in the morning and one in the evening for two consecutive days) for week one, followed by similar four sessions in two consecutive days per week for at least three more weeks, with at least one week interval in between treatment days.

Figure 4B:
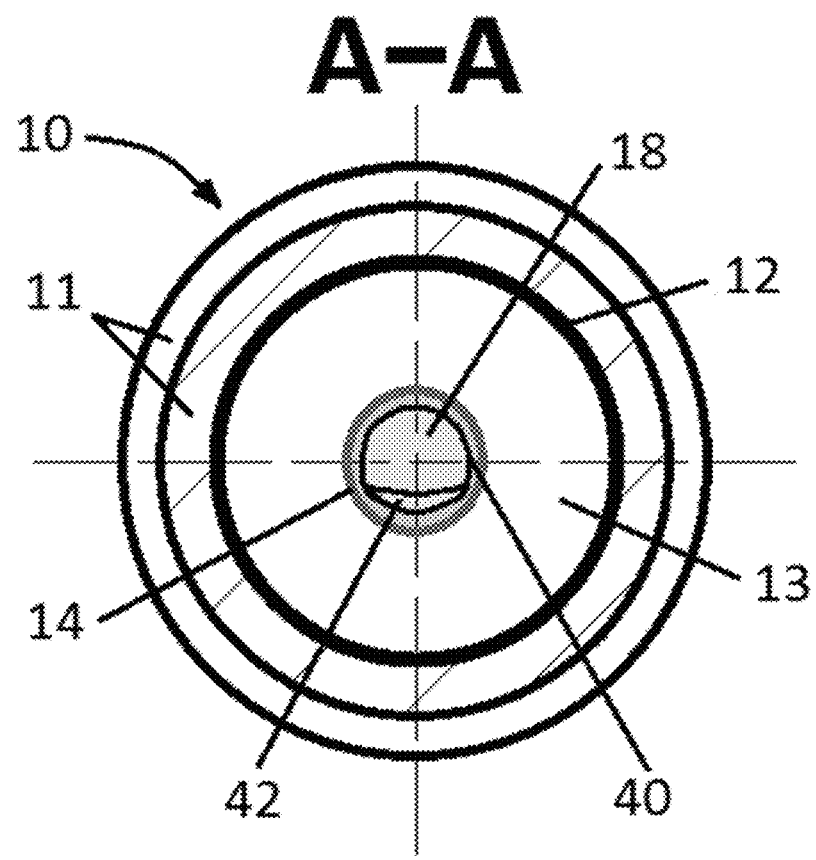
FIG. 4B is a top cross-sectional schematic view along the section plane A-A of the applicator shown in FIG. 4A according to one embodiment of the present invention.

The embodiment presented in FIG. 4A and FIG. 4B is a representation of a special design for the ellipsoidal reflector 12 and applicator/coupling membrane 14 incorporated in the construction of the acoustic pressure shock wave applicator 10, used to treat fungal infections of nail 42 from the toe 40. In general the amount of energy deposited in the targeted area is dependent on the energy setting at the control unit 28 (see FIG. 2), the shape of the ellipsoidal reflector 12 and its total reflective area. In this embodiment in order to maximize the output energy in the treated area, the ellipsoidal reflector 12 has a larger reflective area when compared with the embodiments from FIG. 1A, FIG. 1B, FIG. 1C, FIG. 1D, FIG. 2 or FIG. 3, where the ellipsoidal reflector 12 is half of an ellipsoid. Thus as can be seen from FIG. 4A the ellipsoidal reflector 12 goes beyond the small axis of the ellipsoid 44 and its aperture (where the applicator/coupling membrane 14 is attached) is smaller in diameter, when compared with the dimension XZ of the small axis of the ellipsoid 44. This construction provides a larger reflective surface for the ellipsoidal reflector 12, which translates in higher output energy in the targeted area. The dimension of the aperture of the ellipsoidal reflector 12 is designed to be able to receive a normal human toe 40. The applicator/coupling membrane 14 is specially formed in a concave inward shape to also be able to accommodate a normal human toe 40. For proper transmission of acoustic pressure shock waves 29 (schematically shown in FIG. 2) sufficient acoustic transmission couplings gel (not shown in FIG. 4A and FIG. 4B) must be used in between the toe 40 that needs to be treated and the applicator/coupling membrane 14, which will acoustically couple the toe 40 with applicator/coupling membrane 14.

This special construction of the acoustic pressure shock wave applicator 10 and its associated ellipsoidal reflector 12 and applicator/coupling membrane 14 provides a high energy efficiency solution to treat fungal infections of nail 42 from the toe 40, with the acoustic pressure shock wave applicator 10 being placed only in a single position, without the need to move the acoustic pressure shock wave applicator 10 up and down and around the infected area, as was presented for the embodiments from FIG. 1A, FIG. 1B, FIG. 1C, FIG. 1D, FIG. 1E, FIG. 1F, FIG. 2 and FIG. 3. As seen from FIG. 4A and FIG. 4B, in this embodiment the focal volume 18 (created by the focused acoustic pressure shock waves 29 (schematically shown in FIG. 2)) has an overall dimension that is matching practically the dimension of the toe 40 (longitudinally as seen in FIG. 4A and also radially as seen in FIG. 4B) with the focal volume 18 placed along the large axis of the ellipsoid 46/along the $F_1F_2$ direction, which provides an all around treatment with acoustic pressure shock waves 29 of the toe 40, to completely eradicate the fungus, regardless of its spread around and behind the nail 42 or inside the toe 40.

The acoustic pressure shock wave treatment for fungus of nail 42 from the toe 40 can be done as an independent option or in conjunction with other treatment modalities that employ local ointments or systemic drugs. The acoustic pressure shock waves 29 (schematically shown in FIG. 2) can create acoustic streaming (due to high compressive pressures or the high speed jets generated by the collapsing cavitational bubbles) that can push drugs from a patch/pad or from ointments deposited on the skin inside the targeted area affected by infection, as in toe nails infections, chronic wounds, subcutaneous infections, etc.

For tissue infection treatment of soft and semi-hard tissues (as can be seen for the treatment of nails 42 affected by fungus presented in FIG. 4A and FIG. 4B), it is recommended to use discharge voltages between about 18 and about 30 kV in between electrodes 15A and 15B and in general for the flexibility of the treatment and ease-of-use for the operator/user in this case only hand-held acoustic pressure shock wave applicators 10 is preferably employed. The energy flux density inside the focal volume 18 for each acoustic pressure shock wave 29 (schematically shown in FIG. 2) is preferably in the range of about 0.10 to about 0.80 mJ/mm$^2$. The recommended frequency range for treating soft tissue is about 1 to about 8 Hz and the total amount of acoustic pressure shock waves 29 is preferably in between about 2,000 to about 8,000. If the large amount of acoustic pressure shock waves 29 is not feasible to be accomplished in a single session/treatment, then multiple sessions is preferably applied spread on a certain period of time, every day or every other day. In general, a maximum of four to eight sessions is preferably applied, followed by a resting period of few days to few weeks. If infection is not completely eradicated with the first round of sessions (four to eight sessions, as mentioned before), after recommended resting period, the acoustic pressure shock waves 29 can be administered again, without producing any side effects.

Figure 5A:
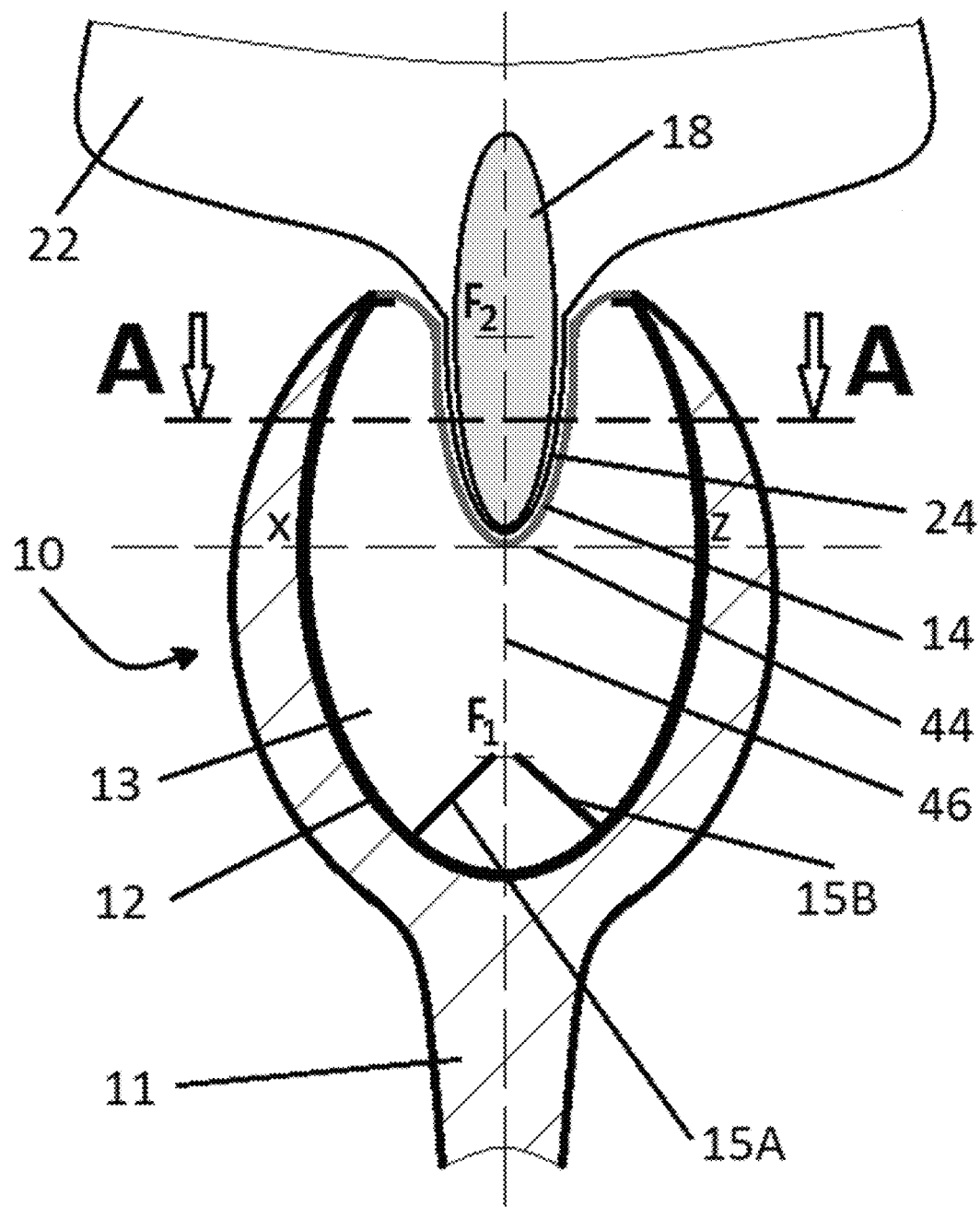
FIG. 5A is a cross-sectional schematic diagram of an applicator receiving a teat affected by mastitis inside a reflector for treatment with acoustic pressure shock waves according to one embodiment of the present invention.
Figure 5B:
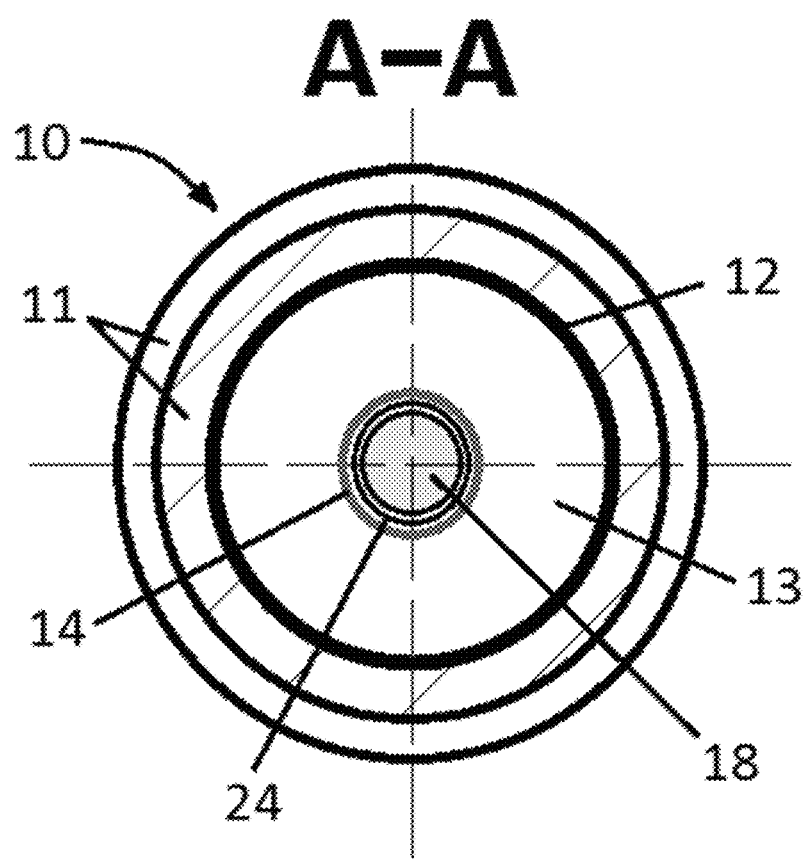
FIG. 5B is a top cross-sectional schematic view along the section plane A-A of the applicator shown in FIG. 5A according to one embodiment of the present invention.

The embodiment presented in FIG. 5A and FIG. 5B is a representation of a special design for the ellipsoidal reflector 12 and applicator/coupling membrane 14 incorporated in the construction of the acoustic pressure shock wave applicator 10, used to treat mastitis infections or prophylactic treatment of a teat 24 from a cow 20 (see FIG. 2). In this case the acoustic pressure shock wave treatment is applied to soft tissue and possible scar tissue that are part of the infected teat 24. As presented before for FIG. 4A and FIG. 4B, in this embodiment from FIG. 5A and FIG. 5B in order to maximize the output energy in the treated area, the ellipsoidal reflector 12 has too a larger reflective area when compared with the embodiments from FIG. 1A, FIG. 1B, FIG. 1C, FIG. 1D, FIG. 2 or FIG. 3, where the ellipsoidal reflector 12 is half of an ellipsoid. Thus as can be seen from FIG. 5A the ellipsoidal reflector 12 goes beyond the small axis of the ellipsoid 44 and its aperture (where the applicator/coupling membrane 14 is attached) is smaller in diameter, when compared with the dimension XZ of the small axis of the ellipsoid 44, which provides a larger reflective surface for the ellipsoidal reflector 12 that translates in higher output energy in the targeted area. The dimension of the aperture of the ellipsoidal reflector 12 is designed to be able to receive an infected cow teat 24 and the applicator/coupling membrane 14 is specially formed in a concave inward shape to also be able to accommodate an infected cow teat 24. For proper transmission of acoustic pressure shock waves 29 (schematically shown in FIG. 2) sufficient acoustic transmission couplings gel (not shown in FIG. 5A and FIG. 5B) must be used in between the teat 24 that needs to be treated and the applicator/coupling membrane 14, which will acoustically couple the teat 24 with applicator/coupling membrane 14.

This special construction of the acoustic pressure shock wave applicator 10 and its associated ellipsoidal reflector 12 and applicator/coupling membrane 14 provides a high energy efficiency solution to treat mastitis infections of the teat 24 from cow 20 (see FIG. 2), with the acoustic pressure shock wave applicator 10 being placed only in a single position, without the need to move the acoustic pressure shock wave applicator 10 up and down and around the infected area, as was presented for the embodiments from FIG. 1A, FIG. 1B, FIG. 1C, FIG. 1D, FIG. 1E, FIG. 1F, FIG. 2 and FIG. 3. In this embodiment from FIG. 5A and FIG. 5B the focal volume 18 (created by the focused acoustic pressure shock waves 29 (schematically shown in FIG. 2)) has an overall dimension that is matching practically the dimension of the cow teat 24 (longitudinally as seen in FIG. 5A and also radially as seen in FIG. 5B) with the focal volume 18 placed along the large axis of the ellipsoid 46/along the $F_1F_2$ direction, which provides an all around treatment with acoustic pressure shock waves 29 of the cow teat 24, to completely eradicate the infection.

For the embodiment presented in FIG. 5A and FIG. 5B, the mastitis treatment or prophylactic treatment to prevent mastitis with acoustic pressure shock waves 29 (schematically shown in FIG. 2) of a teat 24 from a cow 20 (see FIG. 2), similar discharge voltages, same energy flux density inside the focal volume 18 for each acoustic pressure shock wave 29, equivalent frequency range, similar total number of acoustic pressure shock waves 29 delivered in one session and identical sessions sequence (function of somatic cell count (SCC)) are used, as presented for embodiment from FIG. 3.

Due to special shape of the ellipsoidal reflector 12 and applicator/coupling membrane 14, the acoustic pressure shock wave applicator 10 presented in the embodiments from FIG. 4A, FIG. 4B, FIG. 5A and FIG. 5B can be used to treat other appendages of the body, such as soft tissue infections of toes (chronic wounds) or bone infections of the toes, tip of the tail infections for animals, nose infections for both animals and humans, and the like.

Figure 6A:
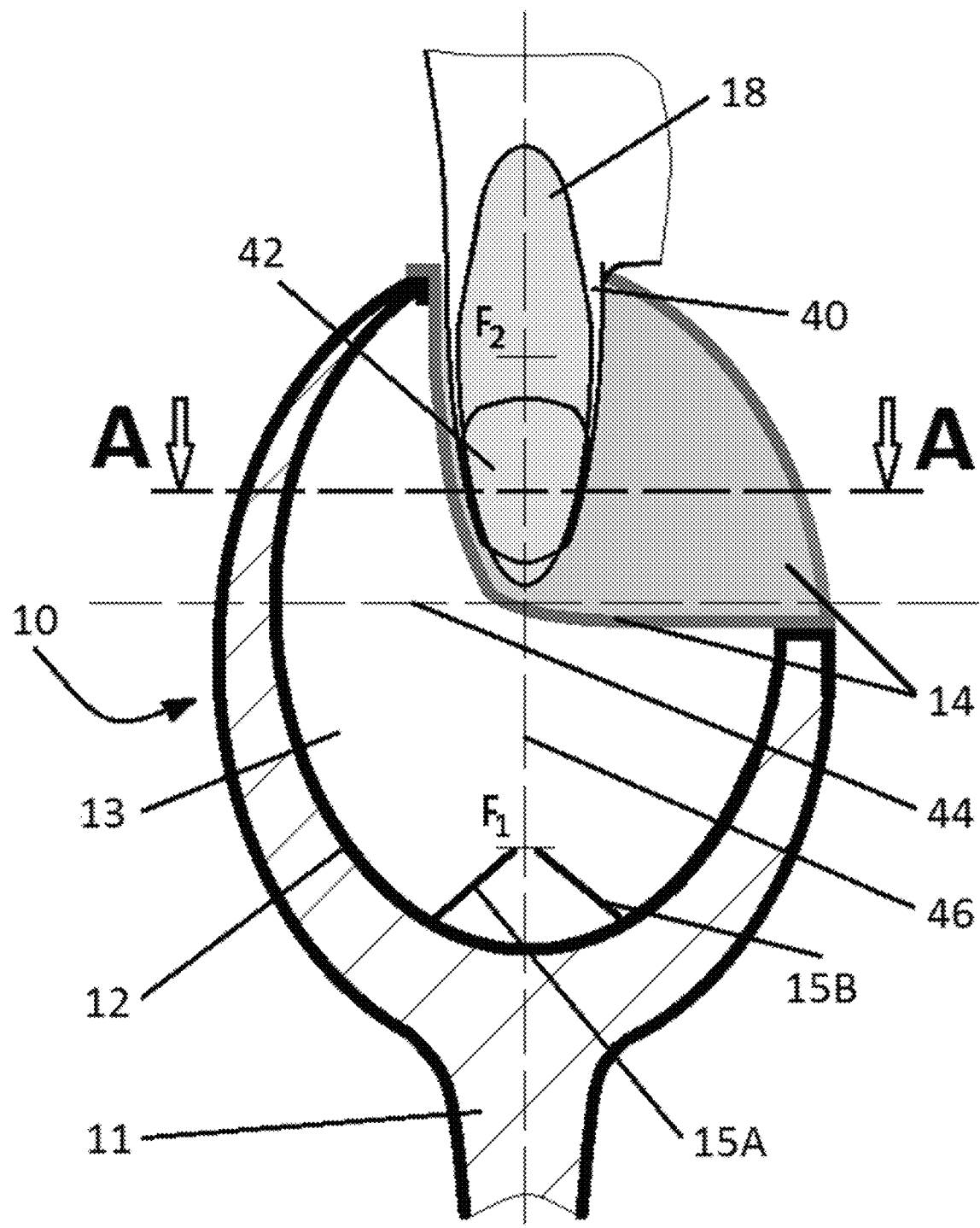
FIG. 6A is a cross-sectional side schematic view of an applicator receiving an infected toe from a side opening slot for treatment with acoustic pressure shock waves according to one embodiment of the present invention.
Figure 6B:
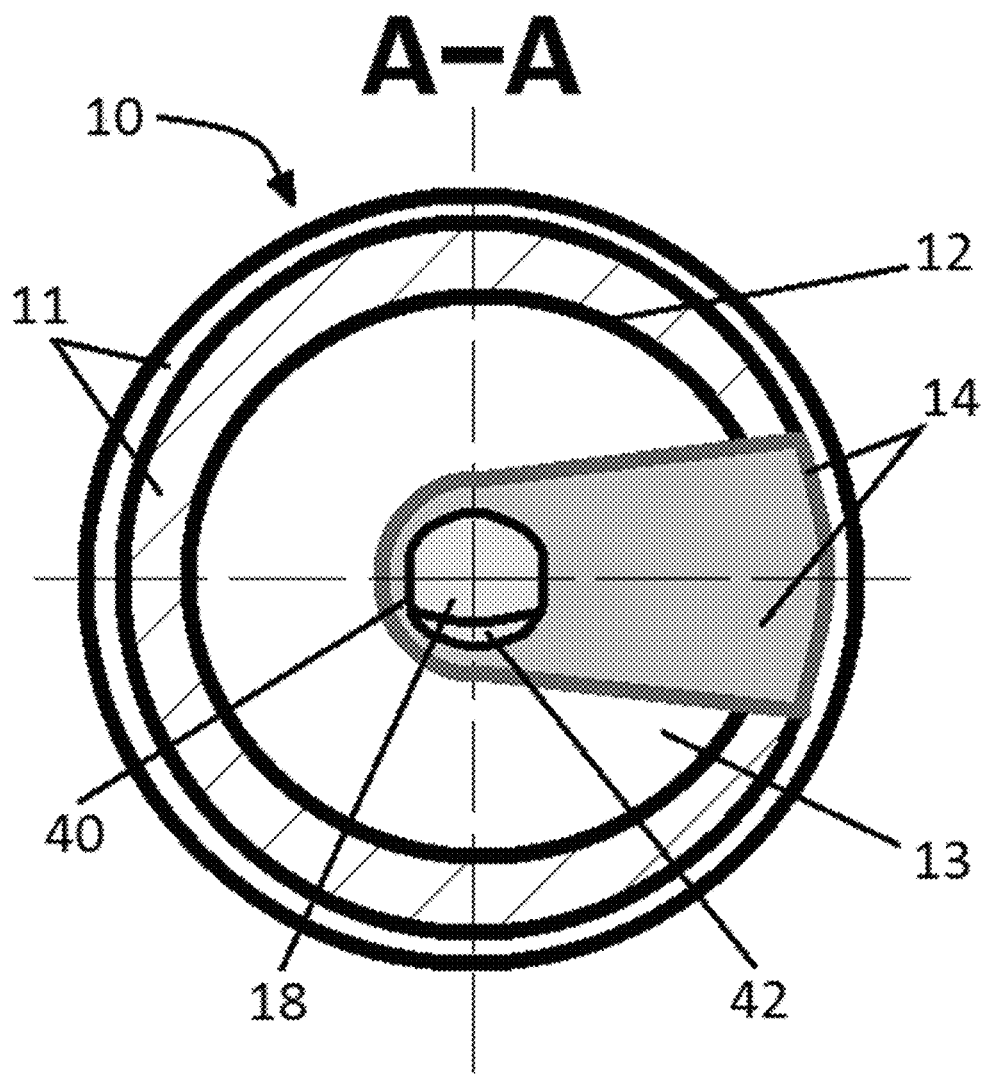
FIG. 6B is a top cross-sectional schematic view along the section plane A-A of the applicator shown in FIG. 6A according to one embodiment of the present invention.
Figure 6C:
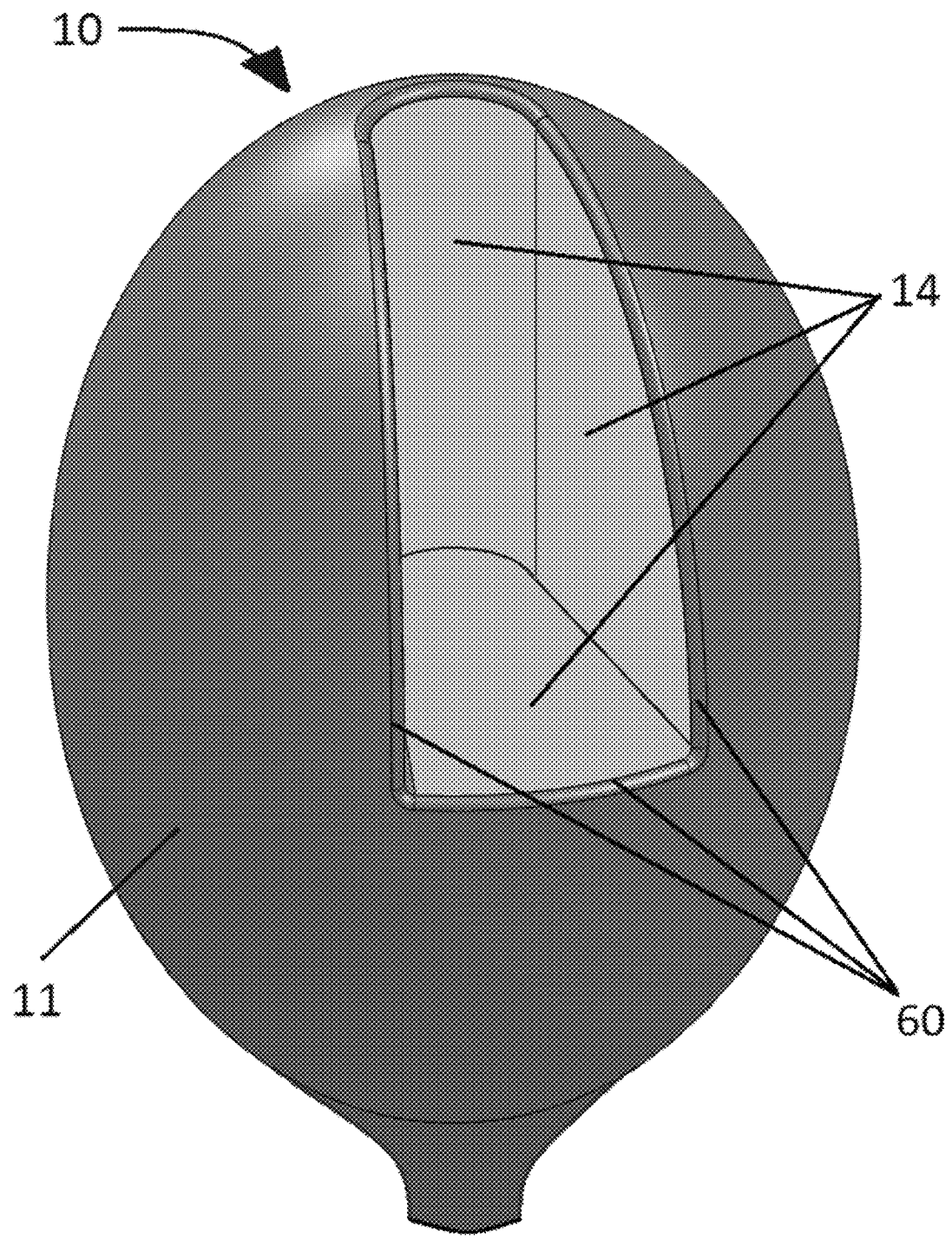
FIG. 6C is a front perspective view of the applicator shown in FIGS. 6A and 6B according to one embodiment of the present invention.

The embodiment presented in FIG. 6A, FIG. 6B and FIG. 6C is a representation of another special design for the ellipsoidal reflector 12 and applicator/coupling membrane 14 incorporated in the construction of the acoustic pressure shock wave applicator 10, used to treat fungal infections of nail 42 from the toe 40. In order to maximize the output energy in the treated area the ellipsoidal reflector 12 has a larger reflective area when compared with the embodiments from FIG. 1A, FIG. 1B, FIG. 1C, FIG. 1D, FIG. 2 or FIG. 3, where the ellipsoidal reflector 12 is half of an ellipsoid. Thus for this embodiment, as can be seen from FIG. 6A, the ellipsoidal reflector 12 goes beyond the small axis of the ellipsoid 44 further up than the embodiment presented in FIG. 4A and FIG. 4B. In this design the ellipsoidal reflector 12 has a side opening/slot 60 (see FIG. 6C) that permits the lateral approach to the toe 40 (perpendicular to the axis of the toe 40) to position the acoustic pressure shock wave applicator 10 for treatment, instead the longitudinal approach (along the axis of the toe 40), as was presented for the embodiment from FIG. 4A and FIG. 4B. This construction provides a larger reflective surface for the ellipsoidal reflector 12, which translates in higher output energy in the targeted area. The dimension of the aperture of the ellipsoidal reflector 12 is designed to be able to receive a normal human toe 40 and also larger ones that are affected by deformities, inflammation, etc., which allows more flexibility when compared with the embodiment from FIG. 4A and FIG. 4B. As can be seen from FIG. 6C the applicator/coupling membrane 14 is also specially formed in a concave inward "U"-shape to match the side opening/slot 60 of the ellipsoidal reflector 12 and also to be able to accommodate a large variety of human toes 40, from normal to deformed ones. For proper transmission of acoustic pressure shock waves 29 (schematically shown in FIG. 2) sufficient acoustic transmission couplings gel (not shown in FIG. 6A, FIG. 6B and FIG. 6C) must be used in between the toe 40 that needs to be treated and the applicator/coupling membrane 14, which will acoustically couple the toe 40 with applicator/coupling membrane 14.

This special construction of the acoustic pressure shock wave applicator 10 and its associated ellipsoidal reflector 12 and applicator/coupling membrane 14 provides a high energy efficiency solution to treat fungal infections of nail 42 from the toe 40, with the acoustic pressure shock wave applicator 10 being placed only in a single position, without the need to move the acoustic pressure shock wave applicator 10 up and down and around the infected area, as was presented for the embodiments from FIG. 1A, FIG. 1B, FIG. 1C, FIG. 1D, FIG. 1E, FIG. 1F, FIG. 2 and FIG. 3. As seen from FIG. 6A and FIG. 6B, in this embodiment the focal volume 18 (created by the focused acoustic pressure shock waves 29 (schematically shown in FIG. 2)) has an overall dimension that is matching practically the dimension of the toe 40 (longitudinally as seen in FIG. 6A and also radially as seen in FIG. 6B), with the focal volume 18 extending along the large axis of the ellipsoid 46 (along the $F_1$-$F_2$ direction), which provides a broader treatment with acoustic pressure shock waves 29 of the tissue of the toe 40, to better eradicate the fungus, regardless of its spread around and behind the nail 42 or inside the toe 40.

As presented in the described embodiment for FIG. 4A and FIG. 4B and for the embodiment of FIG. 6A, FIG. 6B and FIG. 6C the acoustic pressure shock wave treatment for fungus of nail 42 from the toe 40 can be done as an independent option or in conjunction with other treatment modalities that employ local ointments or systemic drugs. The acoustic pressure shock waves 29 (schematically shown in FIG. 2) can create acoustic streaming (due to high compressive pressures or the high speed jets generated by the collapsing cavitational bubbles) that can push drugs from a patch/pad or from ointments deposited on the skin inside the targeted area affected by infection, as in toe nail fungus, chronic wounds, subcutaneous infections, etc.

For the embodiment presented in FIG. 6A, FIG. 6B and FIG. 6C, the treatment for fungus of nail 42 from the toe 40 with acoustic pressure shock waves 29 (schematically shown in FIG. 2), similar discharge voltages, same energy flux density inside the focal volume 18 for each acoustic pressure shock wave 29, equivalent frequency range, similar total number of acoustic pressure shock waves 29 delivered in one session and identical sessions sequence to those presented for embodiment from FIG. 4A and FIG. 4B are preferably used.

Figure 7A:
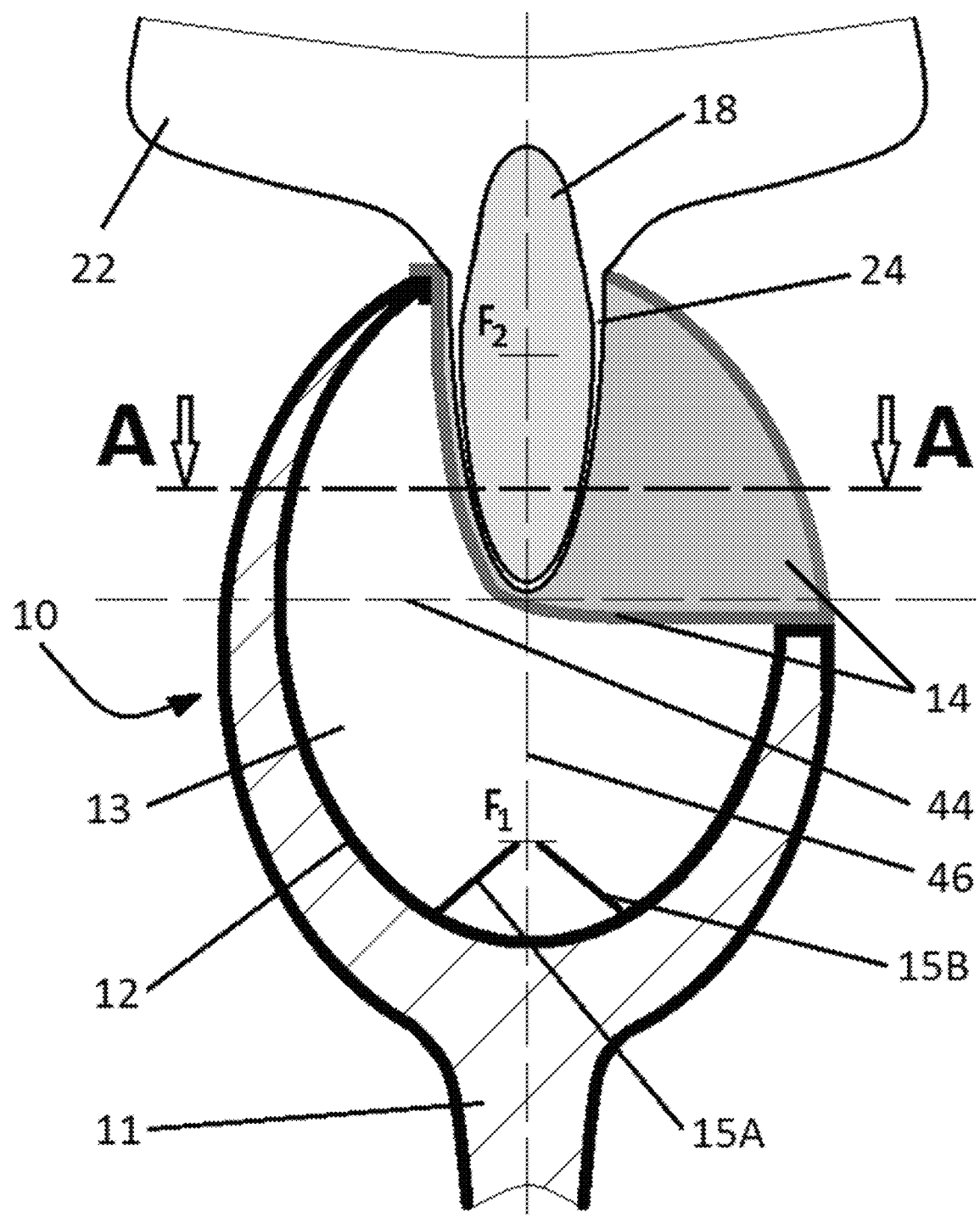
FIG. 7A is a cross-sectional schematic view of an applicator designed to receiving a teat affected by mastitis from a side opening slot for treatment with acoustic pressure shock waves according to one embodiment of the present invention.
Figure 7B:
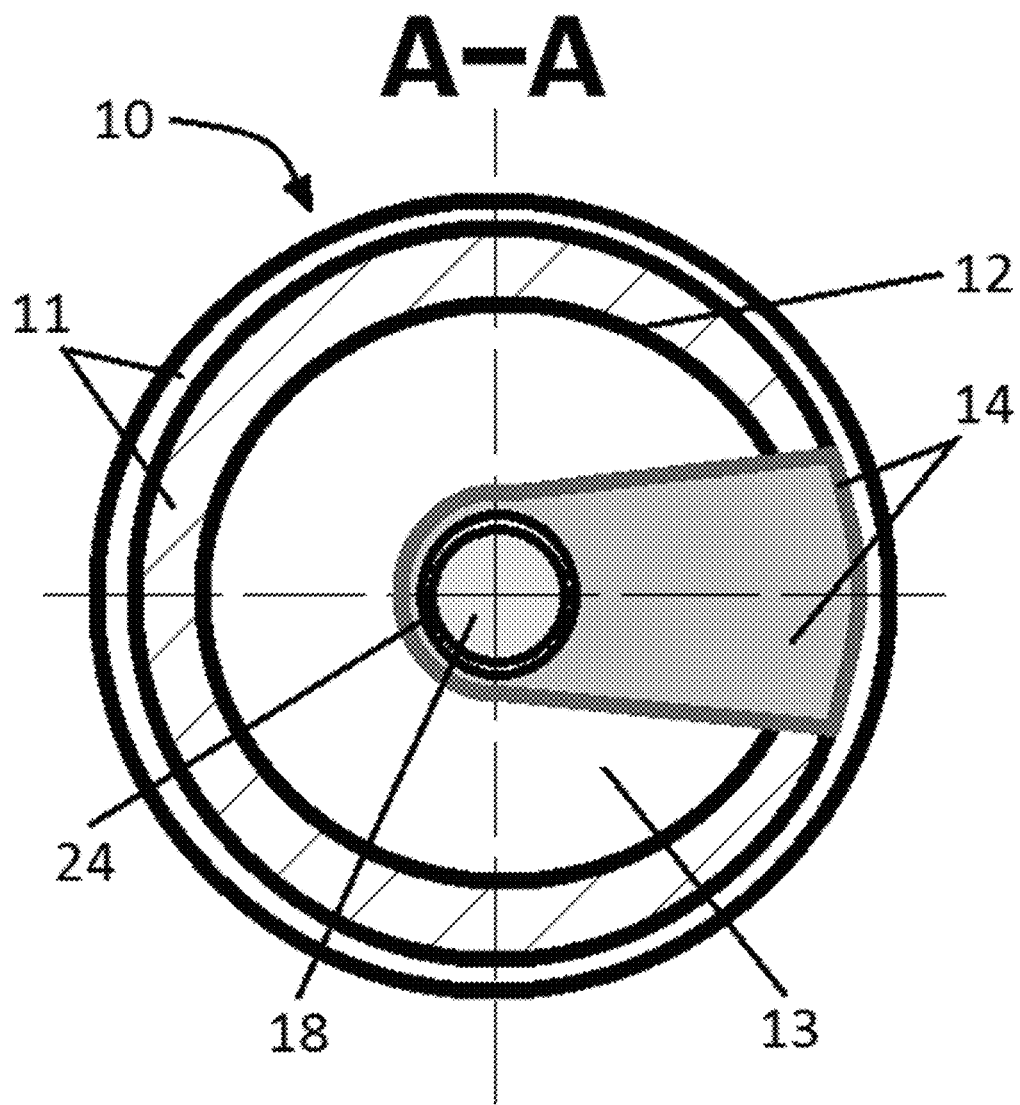
FIG. 7B is a top cross-sectional schematic view along the section plane A-A of the applicator shown in FIG. 7A according to one embodiment of the present invention.
Figure 7C:
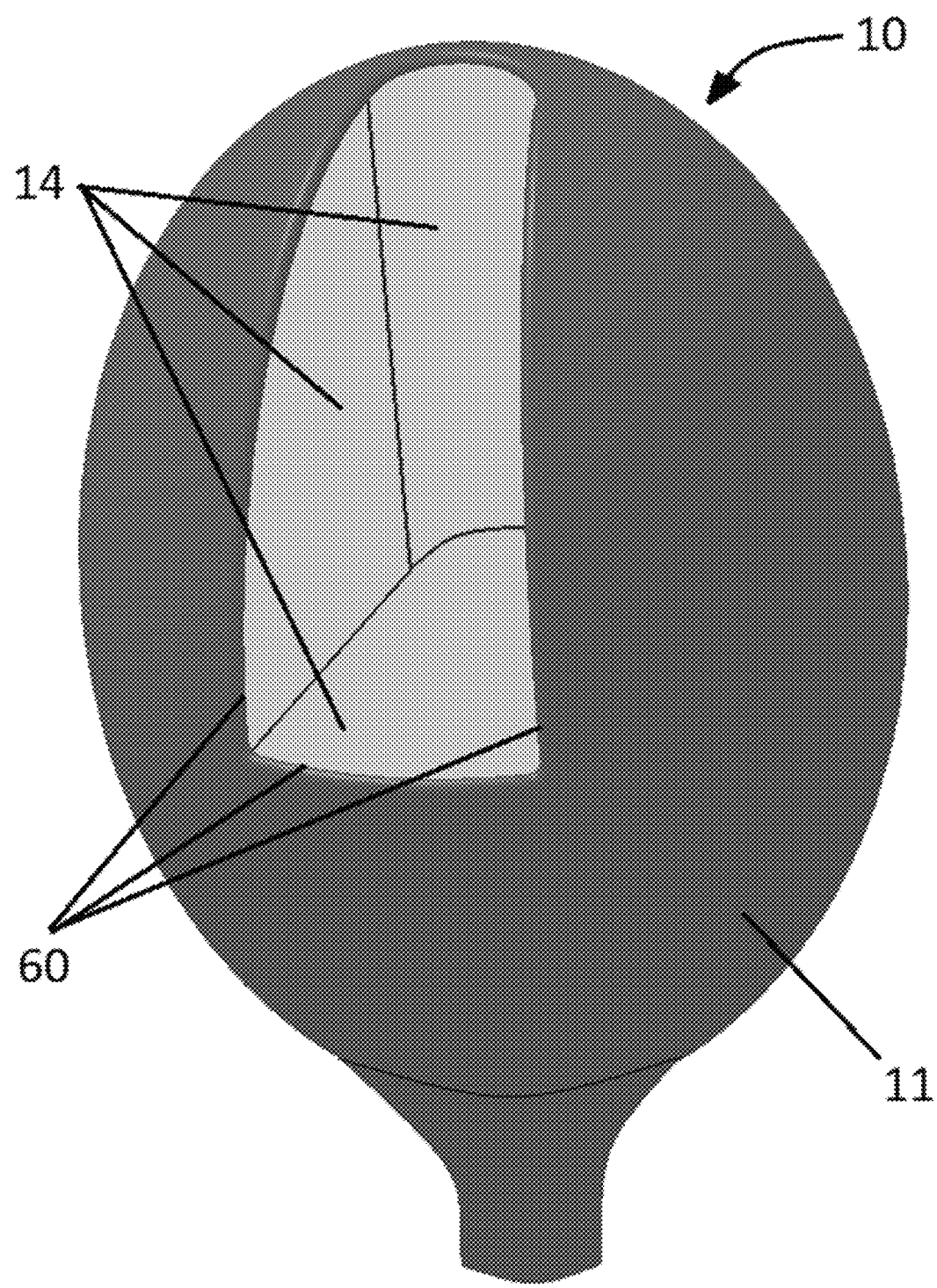
FIG. 7C is a perspective view of the applicator shown in FIGS. 7A and 7B according to one embodiment of the present invention.

The embodiment presented in FIG. 7A, FIG. 7B and FIG. 7C includes an ellipsoidal reflector 12 and applicator/coupling membrane 14 incorporated in the construction of the acoustic pressure shock wave applicator 10, used to treat mastitis infections or prophylactic treatment of a teat 24 from a cow 20 (see FIG. 2). In this case the acoustic pressure shock wave treatment is preferably applied to soft tissue and possible scar tissue that are part of the infected teat 24. Similar to as described with reference to FIG. 6A, FIG. 6B and FIG. 6C, in this embodiment of FIG. 7A, FIG. 7B and FIG. 7C, in order to maximize the output energy in the treated area, the ellipsoidal reflector 12 also has a larger reflective area when compared with the embodiments from FIG. 1A, FIG. 1B, FIG. 1C, FIG. 1D, FIG. 2 or FIG. 3, where the ellipsoidal reflector 12 is half of an ellipsoid. Thus as can be seen from FIG. 7A, the ellipsoidal reflector 12 extends beyond the small axis of the ellipsoid 44 (extending more than the embodiment presented in FIG. 5A and FIG. 5B) and it has a side opening/slot 60 (see FIG. 7C) that permits lateral approach to the teat 24 (perpendicular to the axis of the teat 24) to position the acoustic pressure shock wave applicator 10 for treatment, instead of a longitudinal approach (along the axis of the teat 24), as was presented for the embodiment from FIG. 5A and FIG. 5B. The dimensions of the aperture of the ellipsoidal reflector 12 are preferably chosen so as to be able to receive an infected cow teat 24 and the applicator/coupling membrane 14 is also specially formed in a concave inward "U" shape (see FIG. 17C) to match the slot 60 of the ellipsoidal reflector 12 and also to be able to accommodate a large variety of teats 24, from normal ones to the ones that have significant inflammation due to mastitis. For optimal transmission of acoustic pressure shock waves 29 (schematically shown in FIG. 2) sufficient acoustic transmission coupling gel (not shown in FIG. 7A, FIG. 7B and FIG. 7C) is preferably used in between the teat 24 that needs to be treated and the applicator/coupling membrane 14, which will acoustically couple the teat 24 with applicator/coupling membrane 14.

This embodiment of an acoustic pressure shock wave applicator 10 and its associated ellipsoidal reflector 12 and applicator/coupling membrane 14 provides a high energy efficiency solution to treat mastitis infections or prophylactic treatment of the teat 24 from cow 20 (see FIG. 2), with the acoustic pressure shock wave applicator 10 being placed only in a single position, without the need to move the acoustic pressure shock wave applicator 10 up and down and around the infected area, as was presented for the embodiments from FIG. 1A, FIG. 1B, FIG. 1C, FIG. 1D, FIG. 1E, FIG. 1F, FIG. 2 and FIG. 3. In this embodiment from FIG. 7A, FIG. 7B and FIG. 7C the focal volume 18 (created by the focused acoustic pressure shock waves 29 (schematically shown in FIG. 2)) has an overall dimension that generally matches the dimension of the cow teat 24 (longitudinally as seen in FIG. 7A and also radially as seen in FIG. 7B) that was placed along the large axis of the ellipsoid 46 (along the $F_1$-$F_2$ direction), which provides broader treatment with acoustic pressure shock waves 29 of the cow teat 24, to better eradicate or prevent the infection.

For the embodiment presented in FIG. 7A, FIG. 7B and FIG. 7C, for mastitis treatment or prophylactic treatment to prevent mastitis with acoustic pressure shock waves 29 (schematically shown in FIG. 2) of a teat 24 from a cow 20, similar discharge voltages, same energy flux density inside the focal volume 18 for each acoustic pressure shock wave 29, equivalent frequency range, similar total number of acoustic pressure shock waves 29 delivered in one session and identical session sequence function of somatic cell count (SCC) as described for the embodiment of FIG. 3 are used.

Due to special shape of the ellipsoidal reflector 12 and applicator/coupling membrane 14, the acoustic pressure shock wave applicator 10 presented in the embodiments from FIG. 6A, FIG. 6B, FIG. 6C, FIG. 7A, FIG. 7B and FIG. 7C can be used to treat other appendages of the body, such as soft tissue infections of toes (chronic wounds) or bone infections of the toes, tip of the tail infections for animals, nose infections for both animals and humans, and the like.

Figure 8:
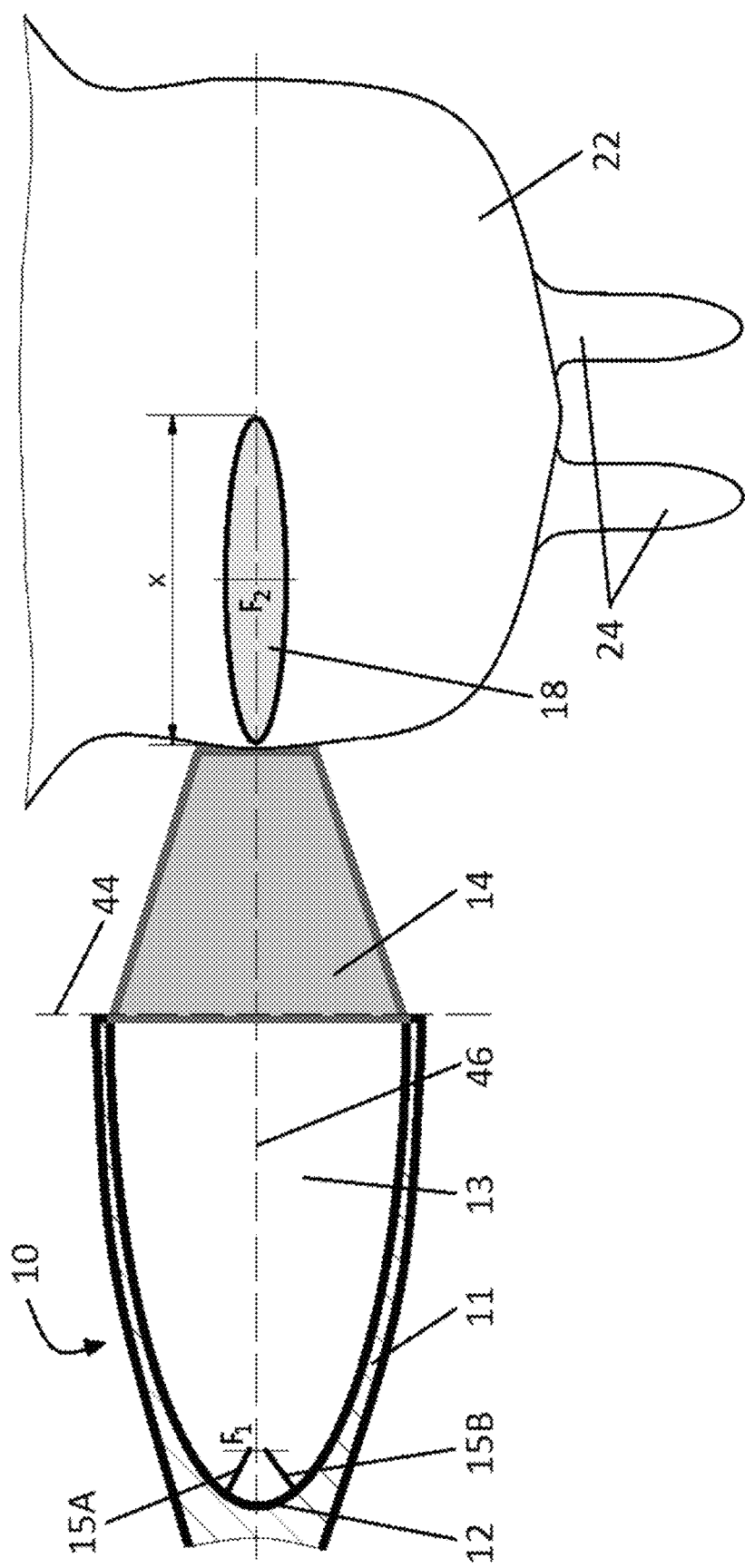
FIG. 8 is a schematic view of an applicator used to deliver acoustic pressure shock waves superficially to an udder affected by mastitis according to one embodiment of the present invention.
Figure 9:
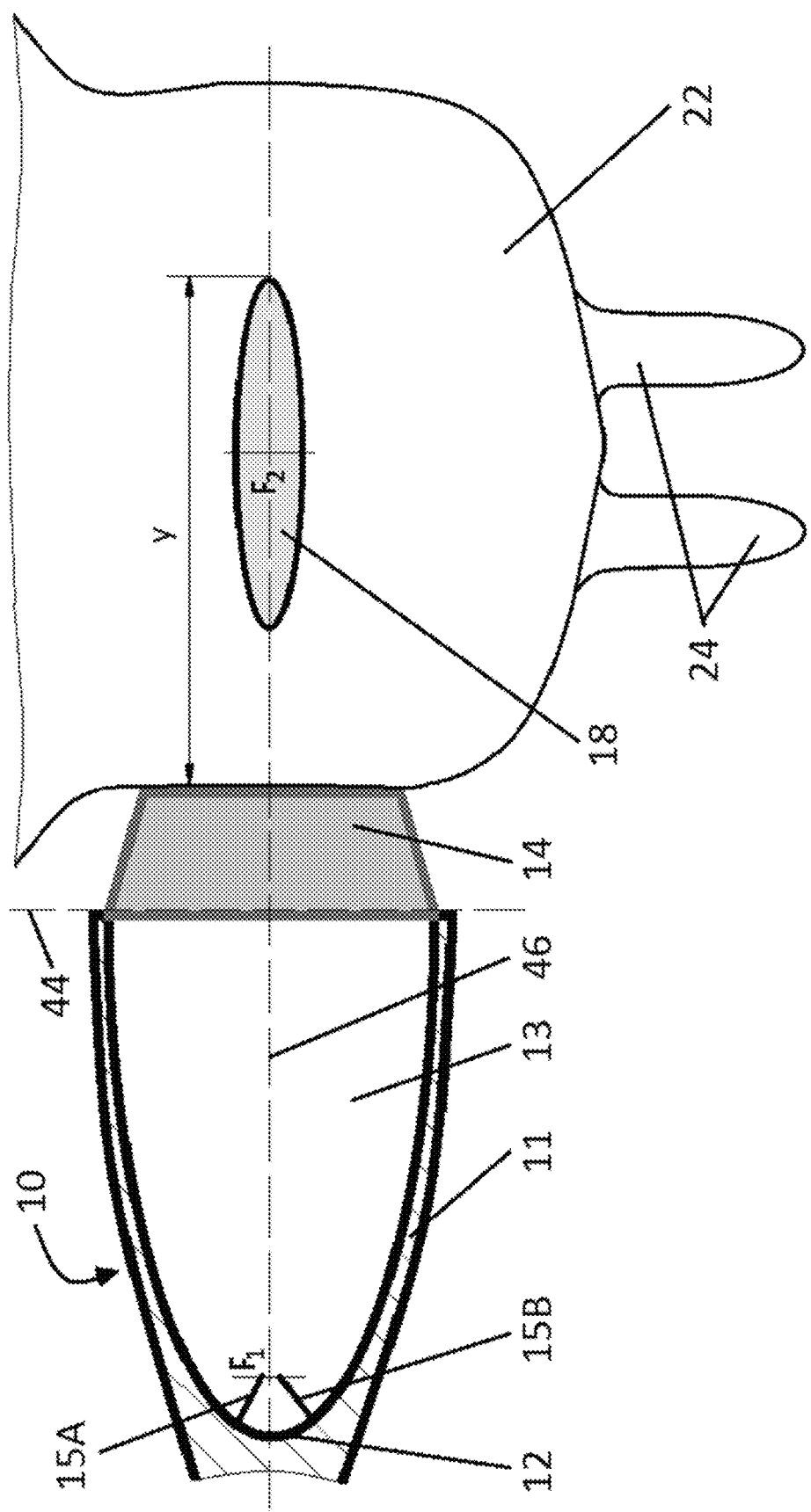
FIG. 9 is a schematic view of an applicator used to deliver acoustic pressure shock waves to the medial portion of an udder affected by mastitis according to one embodiment of the present invention.
Figure 10:
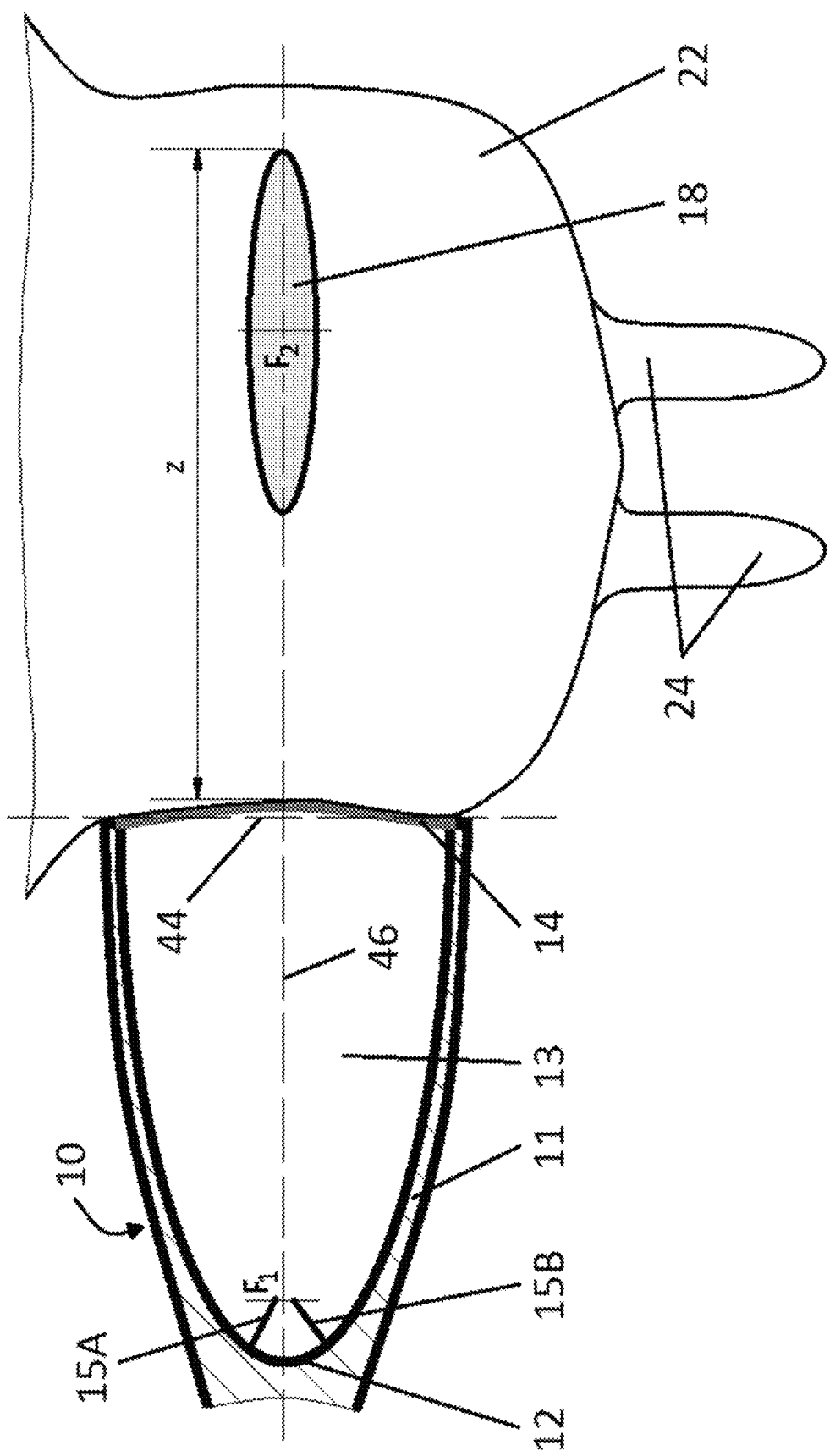
FIG. 10 is a schematic view of an applicator used to deliver acoustic pressure shock waves with deep penetration inside an udder affected by mastitis according to one embodiment of the present invention.

The embodiments from FIG. 8, FIG. 9 and FIG. 10 show the action of acoustic pressure shock waves 29 (schematically shown in FIG. 2) on the udder 22 for a cow 20 (see FIG. 2) affected by mastitis or for prophylactic treatment against recurring mastitis, where the acoustic pressure shock wave applicator 10 has its ellipsoidal reflector 12 and applicator/coupling membrane 14 provided in such way to allow superficial penetration (see FIG. 8), medium penetration (see FIG. 9) or deep penetration (see FIG. 10) of the acoustic pressure shock waves 29 inside the udder 22 that needs treatment for mastitis or prophylactic treatment to prevent mastitis. Due to the fact that the acoustic pressure shock waves 29 can penetrate any type of tissue (soft tissue with inflammation, normal tissue, scar tissue, milk glands) and any milk accumulated into the udder, the propagation of the acoustic pressure shock waves 29 can be accomplished without any restriction in the whole udder 22.

To more broadly cover the infection, the embodiments for the acoustic pressure shock wave applicator 10 presented in FIG. 8, FIG. 9 and FIG. 10 is preferably movable in any direction around the udder 22. It is preferable that the movement of the acoustic pressure shock wave applicator 10 to be done in such way "to paint" all the targeted area affected by infection and the focal volume 18 to completely cover volumetrically the volume of the udder 22 affected by infection.

For proper transmission of acoustic pressure shock waves 29 (schematically shown in FIG. 2) sufficient acoustic transmission couplings gel (not shown in FIG. 8, FIG. 9 and FIG. 10) must be used in between the udder 22 that needs to be treated and the applicator/coupling membrane 14, which will acoustically couple the udder 22 with applicator/coupling membrane 14.

In FIG. 8, the acoustic pressure shock wave applicator 10 is designed to produce the focal volume 18 (created by the focused acoustic pressure shock waves 29 (schematically shown in FIG. 2)) just outside and immediately after/tangential to the applicator/coupling membrane 14, which places the focal volume 18 inside the udder 22 to a maximum penetration distance "x". This will allow the treatment of the superficial wall of the udder and the milk producing sacks from the udder 22 at a penetration not larger than distance "x". Note that the applicator/coupling membrane 14 is tall enough to allow the formation of the focal volume 18 just outside the applicator/coupling membrane 14. Practically, at the same energy setting (energy input) of the control unit 28 (see FIG. 2) if we use one type of ellipsoidal reflector 12, through the applicator/coupling membrane 14 longitudinal dimension (how tall it is) the penetration inside the udder 22 can be controlled. However, the ellipsoidal reflector 12 is preferably a relatively deep reflector wherein the ratio of the large semi-axis and small semi-axis of the ellipsoid is between about 1.4 and 1.6.

When the infection is found deep inside the udder 22 and not into its superficial layers (next to the skin), then an embodiment as presented in FIG. 9 must be used to allow medium penetrations, deeper into the udder 22 to a maximum penetration distance "y". This will allow the treatment of the milk producing sacks from the central region of the udder 22 at a penetration not larger than distance "y". In this case the applicator/coupling membrane 14 is not as thick (i.e. extending a shorter distance outward from applicator) when compared with the embodiment described as to FIG. 8 to allow the formation of the focal volume 18 (created by the focused acoustic pressure shock waves 29 (schematically shown in FIG. 2)) at a certain distance away from the applicator/coupling membrane 14. At the same energy setting (energy input) of the control unit 28 (see FIG. 2), by controlling the longitudinal dimension (height) of the applicator/coupling membrane 14, the position of the focal volume 18 can be adjusted as needed.

In FIG. 10 the penetrations is even deeper when compared with embodiment from FIG. 9 and that is accomplished by using almost a complete flat applicator/coupling membrane 14, which allows a deep penetration into the udder 22 to a maximum penetration distance "z".

For the embodiments presented in FIG. 8, FIG. 9 and FIG. 10 the acoustic pressure shock wave applicators 10 preferably have a fixed volume enclosed in between the ellipsoidal reflector 12 and applicator/coupling membrane 14. However, there are other embodiments in which the control unit 28 (see FIG. 2) has the capability to introduce and retrieve fluid inside the reflector cavity 13, which coupled with a very flexible applicator/coupling membrane 14 allows the acoustic pressure shock wave applicators 10 to be able to adjust the height of the applicator/coupling membrane 14 and thus the penetration of the focal volume 18 inside the targeted area. The variable penetration for an acoustic pressure shock wave applicator 10 allows the operator to use only one acoustic pressure shock wave applicator 10 to cover large volume infections affecting the udder 22 at different penetrations. If the acoustic pressure shock wave applicators 10 have fixed volume enclosed in between the ellipsoidal reflector 12 and applicator/coupling membrane 14, then, for covering infections spread over a large volume inside the udder 22 (ranging from the skin to the middle of the udder 22), several acoustic pressure shock wave applicators 10 might be needed for the treatment of the entire infection.

For the embodiments presented in FIG. 8, FIG. 9 and FIG. 10, for mastitis treatment or prophylactic treatment to prevent mastitis with acoustic pressure shock waves 29 (schematically shown in FIG. 2) of the udder 22 from a cow 20 (see FIG. 2), similar discharge voltages, same energy flux density inside the focal volume 18 for each acoustic pressure shock wave 29, equivalent frequency range, similar total number of acoustic pressure shock waves 29 delivered in one session and identical session sequence function of somatic cell count (SCC) are preferably used, as described as to the embodiment of FIG. 2.

Although the embodiments presented in FIG. 8, FIG. 9 and FIG. 10 are referring to the treatment of mastitis, the same treatment principles linked with variable penetration given by the construction of the applicator/coupling membrane 14, ellipsoidal reflector 12 geometry and energy settings/capabilities of the control unit 28 (see FIG. 2) can be used for any other treatments of hard tissue, hard tissue/soft tissue interface, semi-hard tissue or soft tissue in order to eradicate infection in animals or humans, as presented in embodiments from FIG. 1A, FIG. 1B, FIG. 1C, FIG. 1D, FIG. 1E, FIG. 1F, FIG. 2, FIG. 3, FIG. 4A, FIG. 4B, FIG. 5A, FIG. 5B, FIG. 6A, FIG. 6B, FIG. 6C, FIG. 7A, FIG. 7B, and FIG. 7C.

In the embodiments from FIG. 1A, FIG. 1B, FIG. 1C, FIG. 1D, FIG. 1E, FIG. 1F, FIG. 2, FIG. 3, FIG. 4A, FIG. 4B, FIG. 5A, FIG. 5B, FIG. 6A, FIG. 6B, FIG. 6C, FIG. 7A, FIG. 7B, FIG. 7C, FIG. 8, FIG. 9, and FIG. 10 the acoustic pressure shock wave applicator 10 incorporates an ellipsoidal reflector 12 or a parabolic reflector 12A (see FIG. 1F) that creates acoustic pressure shock waves 29 (schematically shown in FIG. 2) that are focused towards the second focal point $F_2$ of the ellipsoidal reflector 12 (FIG. 1A, FIG. 1B, FIG. 1C, FIG. 1D, FIG. 1E, FIG. 2, FIG. 3, FIG. 4A, FIG. 4B, FIG. 5A, FIG. 5B, FIG. 6A, FIG. 6B, FIG. 6C, FIG. 7A, FIG. 7B, FIG. 7C, FIG. 8, FIG. 9, and FIG. 10) or towards the focus point F for parabolic reflector 12A (FIG. 1F). In this way a focused acoustic pressure shock waves 29 are created that have maximum energies inside the focal volume 18 centered in the second focal point $F_2$ (for ellipsoidal reflector 12) or the focus point F (for the parabolic reflector 12A). Using either the electrohydraulic principle or electromagnetic or piezoelectric principles, besides the acoustic pressure shock waves 29 that are focused other types of acoustic pressure shock waves can be created that are unfocused, radial, planar or pseudo-planar in nature.

Figure 11:
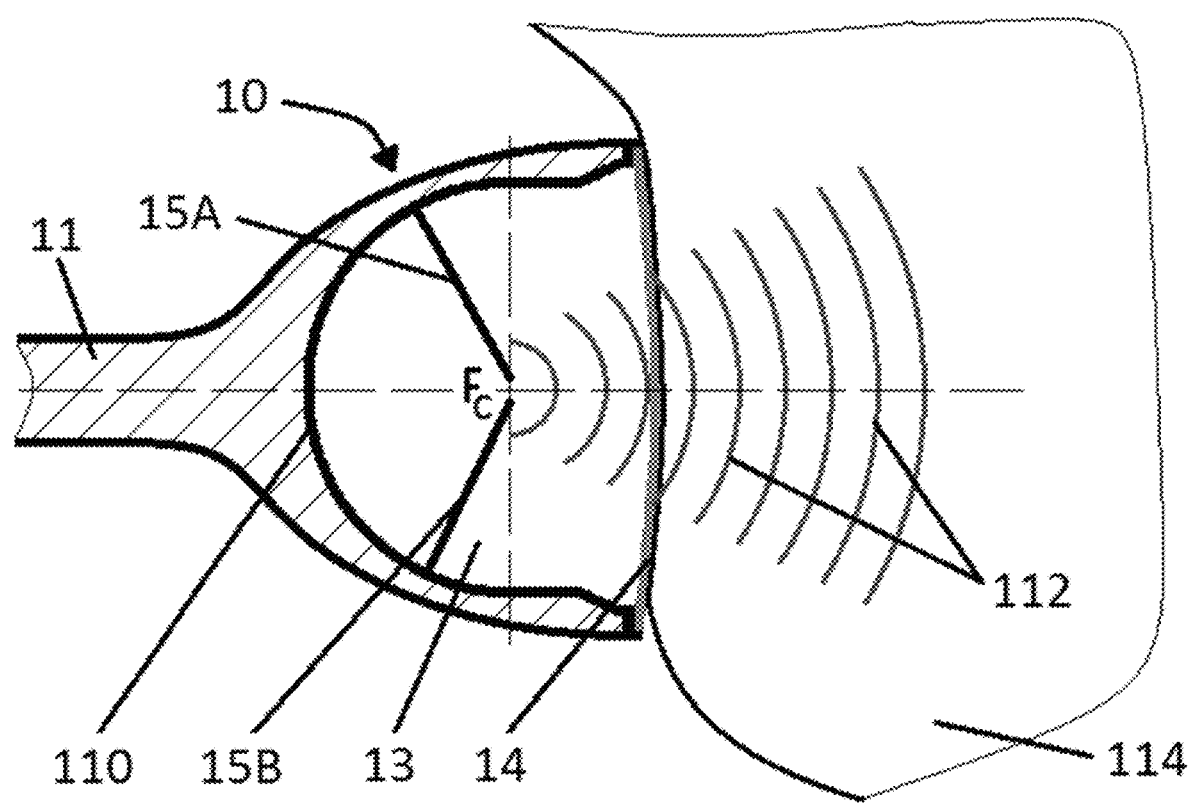
FIG. 11 is a schematic view of an applicator with a spherical reflector to deliver radial and unfocused acoustic pressure shock waves to targeted tissue affected by infection according to one embodiment of the present invention.

In another embodiment shown in FIG. 11 the acoustic pressure shock wave applicator 10 uses a spherical reflector 110 that sends radial acoustic pressure shock waves 112 inside the targeted tissue 114 (human or animal). The spherical reflector 110 has only a central point $F_C$ where the radial acoustic pressure shock waves 112 are generated (via the high voltage discharge between first electrode 15A and second electrode 15B inside a liquid medium from reflector cavity 13) and they exit via the aperture of the spherical reflector 110 through the applicator/coupling membrane 14. In order for the aperture of the spherical reflector 110 to not interfere with radial acoustic pressure shock waves 112, the spherical reflector 110 is cylindrical above the plane of the central point $F_C$. The reflected waves on the bottom surface of the spherical reflector 110 will be sent back towards point $F_C$ and not inside the targeted tissue 114. By their nature, the primary radial acoustic pressure shock waves 112 (exiting through the aperture of the spherical reflector 110) are also unfocused and thus they move inside the targeted tissue 114 away from their point of origin $F_C$ without being able to be concentrated in a certain focal region, as seen before for the acoustic pressure shock waves 29 that are focused (schematically shown in FIG. 2). Along their way inside the targeted tissue 114, the radial acoustic pressure shock waves 112 deposit their energy into the infected tissue, until all of their energy is consumed. In other words, the radial acoustic pressure shock waves 112 have their maximum energy superficially near the skin (at the entrance into the human or animal bodies) and become weaker as they travel further inside the targeted tissue 114. This means that is preferable to use this embodiment presented in FIG. 11 to treat human or animal tissues affected by infection that are under the skin and do not have deep penetration inside the human or animal bodies. The radial acoustic pressure shock waves 112 penetrations are controlled by the input energy delivered by the control unit 28 (see FIG. 2). For electrohydraulic devices the input energy from control unit 28 is the high voltage discharge in between electrodes 15A and 15B. For electromagnetic devices the input energy from control unit 28 is the current necessary to activate the flat or cylindrical electromagnetic coils and for piezoelectric devices is the high voltage that excite the piezoelectric crystals/elements or the piezoelectric fibers. Another way to create radial acoustic pressure shock waves 112 is given by ballistic devices that use pneumatics to push at high speeds a small cylindrical piece (bullet) against a plate that vibrates (due to the impact of the bullet) and thus creating/generating radial acoustic pressure shock waves 112. The ballistic devices were not specifically depicted in any of the figures of this patent, but can be used to generate radial acoustic pressure shock waves 112.

In order to broadly cover an infection over a larger area, the embodiment for the acoustic pressure shock wave applicator 10 presented in FIG. 11 is preferably moved in any direction around/along the targeted tissue 114 (human or animal). Preferably the movement of the acoustic pressure shock wave applicator 10 is done in such way "to paint" all the targeted area affected by infection from the targeted tissue 114.

For optimnal transmission of radial acoustic pressure shock waves 112 sufficient acoustic transmission couplings gel (not shown in FIG. 11) are preferably used in between the targeted tissue 114 (human or animal) that being treated and the applicator/coupling membrane 14, which will acoustically couple the targeted tissue 114 with applicator/coupling membrane 14.

For the embodiment presented in FIG. 11, the acoustic pressure shock wave applicator 10 is used for treatment with radial acoustic pressure shock waves 112 of infections of hard tissue/bone, or of the interface between hard and soft tissue, or of semi-hard tissue, or of soft tissue. Preferably similar energy flux density outside the applicator/coupling membrane 14 for each radial acoustic pressure shock wave 112, same frequency range, equivalent total number of radial acoustic pressure shock waves 112 delivered in one session and identical session sequence as was described for embodiments from FIG. 1A, FIG. 1B, FIG. 1C, FIG. 1D, FIG. 1E, FIG. 1F (hard tissue/bone, or of the interface between hard and soft tissue infections), FIG. 2, FIG. 3, FIG. 5A, FIG. 5B, FIG. 7A, FIG. 7B, FIG. 7C (for soft tissue infections), FIG. 4A, FIG. 4B, FIG. 6A, FIG. 6B and FIG. 6C (for semi-hard tissue infections) are preferably used.

Figure 12:
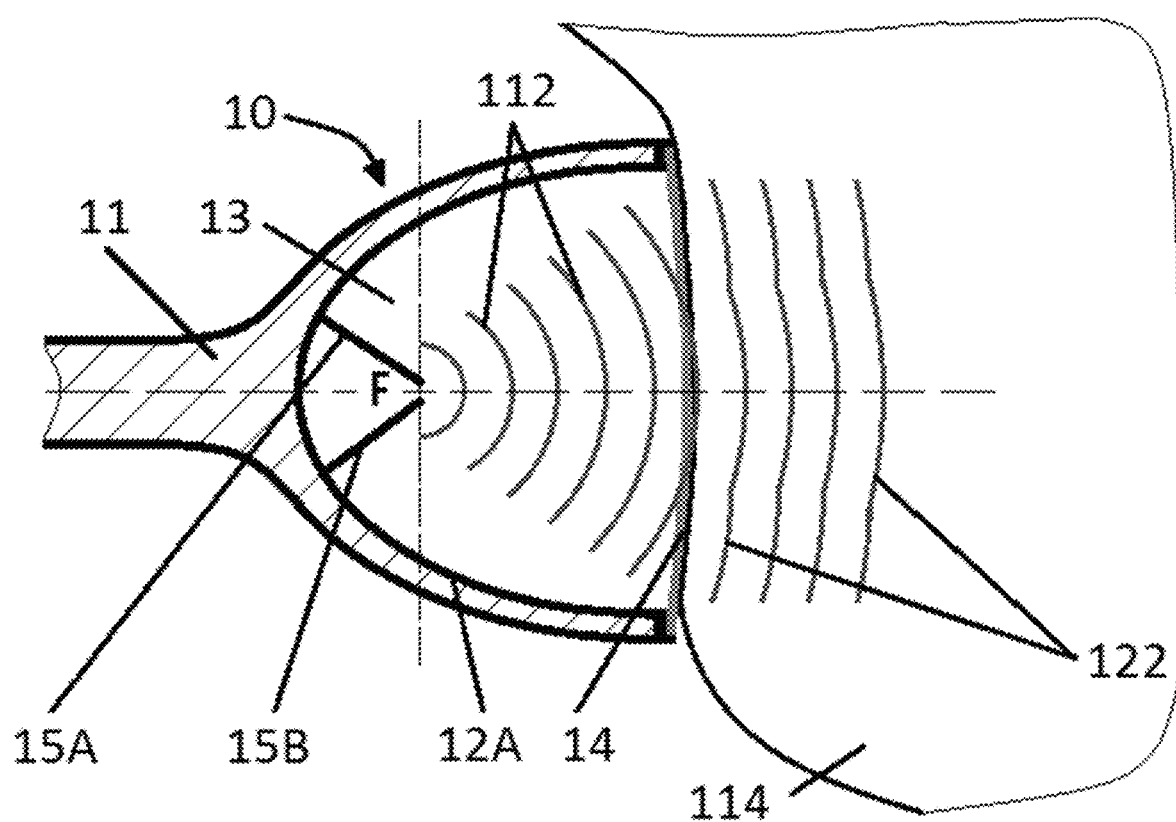
FIG. 12 is a schematic view of an applicator with a parabolic reflector to deliver pseudo-planar and unfocused acoustic pressure shock waves to targeted tissue affected by infection according to one embodiment of the present invention.

In the embodiment shown in FIG. 12 the acoustic pressure shock wave applicator 10 uses a parabolic reflector 12A that sends pseudo-planar acoustic pressure shock waves 122 outside the applicator/coupling membrane 14 and inside the targeted tissue 114 (human or animal). The parabolic reflector 12A has only a central point/focus point F where radial acoustic pressure shock waves 112 are generated (via the high voltage discharge between first electrode 15A and second electrode 15B in the liquid present inside the reflector cavity 13). The radial acoustic pressure shock waves 112 propagate and reflect on the parabolic reflector 12A at different time points, which creates secondary pressure wave fronts (not shown on FIG. 12 to keep clarity), especially at the edge/aperture of the parabolic reflector 12A. The combination of direct radial acoustic pressure shock waves 112 with the secondary pressure shock wave fronts creates pseudo-planar acoustic pressure shock waves 122 outside the applicator/coupling membrane 14. By their nature, the pseudo-planar acoustic pressure shock waves 122 (exiting through the aperture of the parabolic reflector 12A) are also unfocused and thus they move inside the targeted tissue 114 away from their point of origin F without being able to be concentrated in a certain focal region, as seen before for the acoustic pressure shock waves 29 that are focused (schematically shown in FIG. 2). Along their way inside the targeted tissue 114, the pseudo-planar acoustic pressure shock waves 122 deposit their energy into the infected tissue, until all of their energy is consumed. In other words, the pseudo-planar acoustic pressure shock waves 122 have their maximum energy superficially near the skin (at the entrance into the human or animal bodies) and become weaker as they travel further inside the targeted tissue 114. This means that is preferable to use this embodiment presented in FIG. 12 to treat human or animal tissues affected by infection that are under the skin and do not have deep penetration inside the human or animal bodies. The penetrations of the pseudo-planar acoustic pressure shock waves 122 are controlled by the input energy delivered by the control unit 28 (see FIG. 2), in the form of high voltage setting for electrohydraulic and piezoelectric devices and electrical current setting for electromagnetic devices.

To more broadly cover the infection of large infection areas, the acoustic pressure wave applicator 10 shown in FIG. 12 is preferably moved in any direction around/along the targeted tissue 114 (human or animal). It is preferable that the movement of the acoustic pressure shock wave applicator 10 to be done in such way "to paint" all the targeted area affected by infection.

For optimal transmission of pseudo-planar acoustic pressure shock waves 122 sufficient acoustic transmission couplings gel (not shown in FIG. 12) is preferably used in between the targeted tissue 114 (human or animal) bring treated and the applicator/coupling membrane 14, which will acoustically couple the targeted tissue 114 with applicator/coupling membrane 14.

For the embodiment presented in FIG. 12, the acoustic pressure shock wave applicators 10 are used for treatment with pseudo-planar acoustic pressure shock waves 122 of infections of hard tissue/bone, or of the interface between hard and soft tissue, or of semi-hard tissue, or of soft tissue. For such treatments, similar energy flux density outside the applicator/coupling membrane 14 for each pseudo-planar acoustic pressure shock waves 122, same frequency range, equivalent total number of pseudo-planar acoustic pressure shock waves 122 delivered in one session and identical session sequence, as described for the embodiments of FIG. 1A, FIG. 1B, FIG. 1C, FIG. 1D, FIG. 1E, FIG. 1F (hard tissue/bone, or of the interface between hard and soft tissue infections), FIG. 2, FIG. 3, FIG. 5A, FIG. 5B, FIG. 7A, FIG. 7B, FIG. 7C (for soft tissue infections), FIG. 4A, FIG. 4B, FIG. 6A, FIG. 6B and FIG. 6C (for semi-hard tissue infections) are preferably used.

Planar acoustic pressure shock waves can be easily generated by relatively flat piezoelectric crystals (not specifically shown in any of the figures of this patent). These piezoelectric devices can be used to generate planar acoustic pressure shock waves, and direct them inside the human or animal bodies to treat superficial infections that does not require the acoustic pressure shock waves 29 (depicted in FIG. 2) that are focused. In such embodiment, the acoustic pressure shock wave applicator 10 is preferably moved in any direction around/along the targeted tissue 114 (human or animal). It is preferably that the movement of the acoustic pressure shock wave applicator 10 be done in such way "to paint" all the targeted area affected by infection. For optimal transmission of planar acoustic pressure shock waves sufficient acoustic transmission couplings gel must be used in between the targeted tissue 114 being treated and the applicator/coupling membrane 14, which will acoustically couple the targeted tissue 114 with applicator/coupling membrane 14. The treatment parameters preferably follow the same scheme as described for the embodiments of FIG. 1A, FIG. 1B, FIG. 1C, FIG. 1D, FIG. 1E, FIG. 1F (hard tissue/bone, or of the interface between hard and soft tissue infections), FIG. 2, FIG. 3, FIG. 5A, FIG. 5B, FIG. 7A, FIG. 7B, FIG. 7C (for soft tissue infections), FIG. 4A, FIG. 4B, FIG. 6A, FIG. 6B and FIG. 6C (for semi-hard tissue infections).

Figure 13:
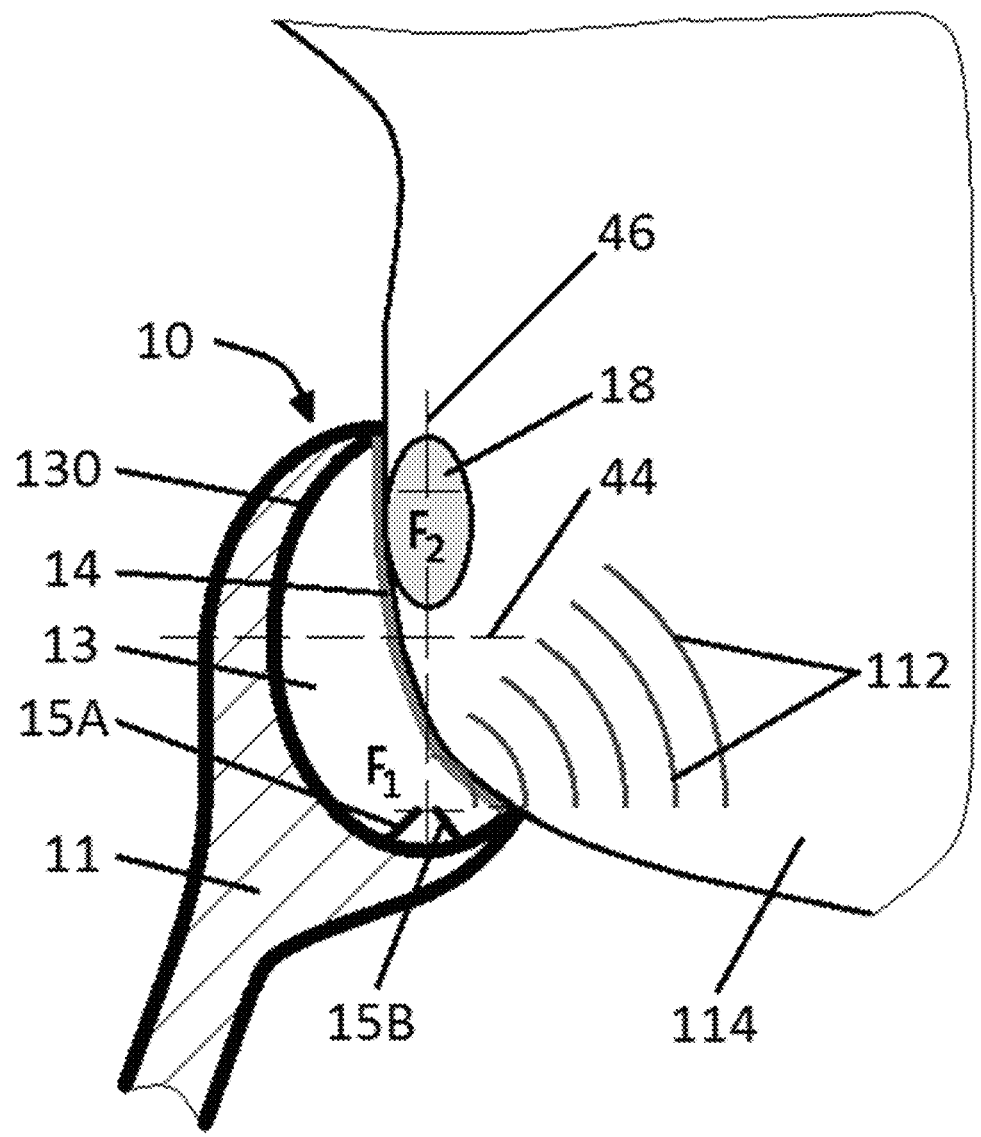
FIG. 13 is a schematic view of an applicator with a reversed reflector to deliver both radial and focused acoustic pressure shock waves to targeted tissue affected by infection according to one embodiment of the present invention.

In the embodiment shown in FIG. 13 the acoustic pressure shock wave applicator 10 uses a reversed reflector 130 that sends both radial acoustic pressure shock waves 112 and focused acoustic pressure shock waves 29 (schematically shown in FIG. 2) outside the applicator/coupling membrane 14 and inside the targeted tissue 114 (human or animal). The reversed reflector 130 has the aperture along large axis of the ellipsoid 46 and not along the small axis of the ellipsoid 44, as seen in the embodiments from FIG. 4A, FIG. 5A, FIG. 8, FIG. 9 and FIG. 10. Due to this special geometry, the high voltage discharge in between electrodes 15A and 15B in the liquid that fills the reflector cavity 13 creates acoustic pressure shock waves 29 (schematically shown in FIG. 2 but not shown in FIG. 13) that are reflected on the reversed reflector 130 and focused towards the focal volume 18 (centered around the second focal point $F_2$) and simultaneously radial acoustic pressure shock waves 112 are emanating directly from first focal point $F_1$ towards the targeted tissue 114. By focusing acoustic pressure shock waves 29 into the focal volume 18 and sending radial acoustic pressure shock waves 112 simultaneously inside the targeted tissue 114 produces an increased efficiency due the fact that in one position of the acoustic pressure shock waves applicator 10 a larger area of targeted tissue 114 is treated in the same time. It is interesting to note that for this acoustic pressure shock wave applicator 10 the focal volume 18 is oriented tangential to the skin, which allows the treatment with focused acoustic pressure shock waves 29 only for superficial infections and larger area in one position (due to tangential orientation of the focal volume 18 instead of perpendicular orientation on the targeted area/skin as presented in FIG. 1A, FIG. 1B, FIG. 1C, FIG. 1D, FIG. 1E, FIG. 1F, FIG. 2, FIG. 3, FIG. 8, FIG. 9, and FIG. 10). Such orientation combined with the fact that the radial acoustic pressure shock waves 112 are indicated also for superficial treatment, provides advantages in that the acoustic pressure shock wave applicators 10 that contain reversed reflector 130 in their constructions can be efficiently used for the treatment of superficial infections that are spread on a large area. However, in some cases in order to broadly cover an infection, the embodiment for the acoustic pressure shock wave applicator 10 presented in FIG. 13 is preferably moved in any direction around/along the targeted tissue 114. It is preferable that the movement of the acoustic pressure shock wave applicator 10 to be done in such way "to paint" all the targeted area affected by infection.

For optimal transmission of both focused acoustic pressure shock waves 29 (schematically shown in FIG. 2) and radial acoustic pressure shock waves 112, sufficient acoustic transmission couplings gel (not shown in FIG. 13) is preferably used in between the targeted tissue 114 (human or animal) being treated and the applicator/coupling membrane 14, which will acoustically couple the targeted tissue 114 with applicator/coupling membrane 14.

For the embodiment presented in FIG. 13, the acoustic pressure shock wave applicators 10 are used for simultaneous treatment with focused acoustic pressure shock waves 29 (schematically shown in FIG. 2) and radial acoustic pressure shock waves 112 of infections of hard tissue/bone, or of the interface between hard and soft tissue, or of semi-hard tissue, or of soft tissue. For such treatment, the same discharge voltages, similar energy flux density outside the applicator/coupling membrane 14, same frequency range, equivalent total number of focused acoustic pressure shock waves 29/radial acoustic pressure shock waves 112 delivered in one session and identical session sequence as described for embodiments of FIG. 1A, FIG. 1B, FIG. 1C, FIG. 1D, FIG. 1E, FIG. 1F (hard tissue/bone, or of the interface between hard and soft tissue infections), FIG. 2, FIG. 3, FIG. 5A, FIG. 5B, FIG. 7A, FIG. 7B, FIG. 7C (for soft tissue infections), FIG. 4A, FIG. 4B, FIG. 6A, FIG. 6B and FIG. 6C (for semi-hard tissue infections) are preferably used.

Figure 14A:
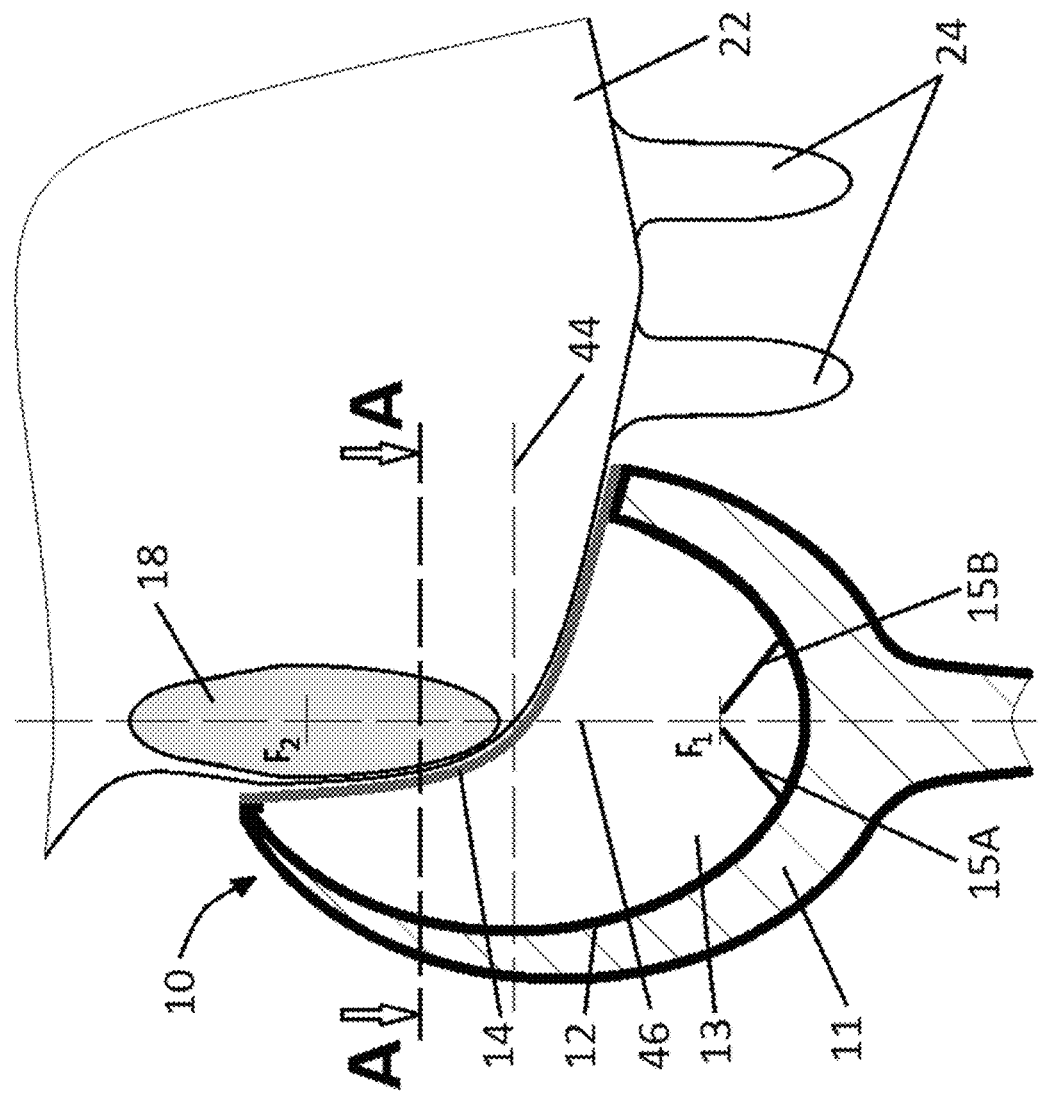
FIG. 14A is a cross-sectional schematic view of an applicator designed to receiving the side an udder affected by mastitis for treatment with acoustic pressure shock waves according to one embodiment of the present invention.
Figure 14B:
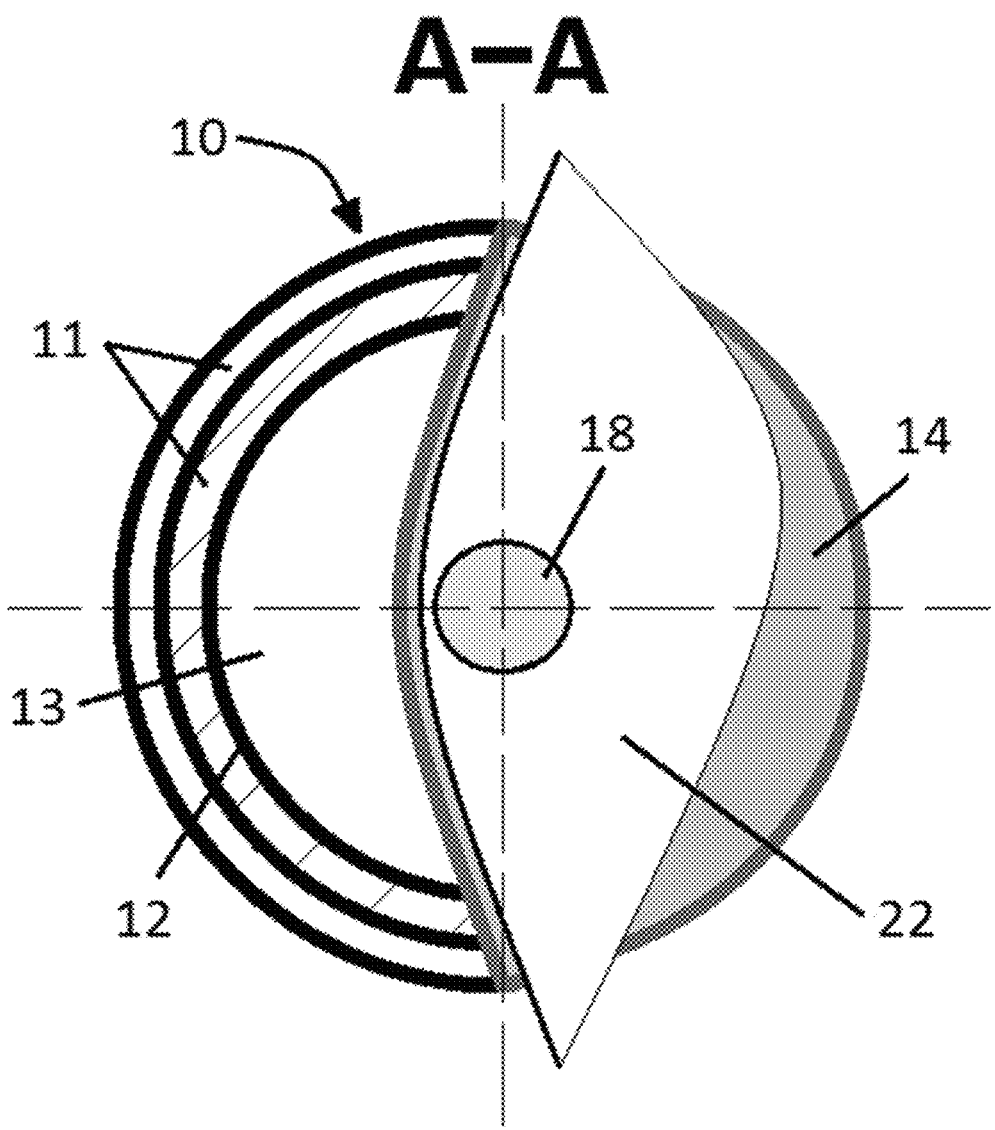
FIG. 14B is a top cross-sectional schematic view along the section plane A-A of the applicator shown in FIG. 14A according to one embodiment of the present invention.
Figure 14C:
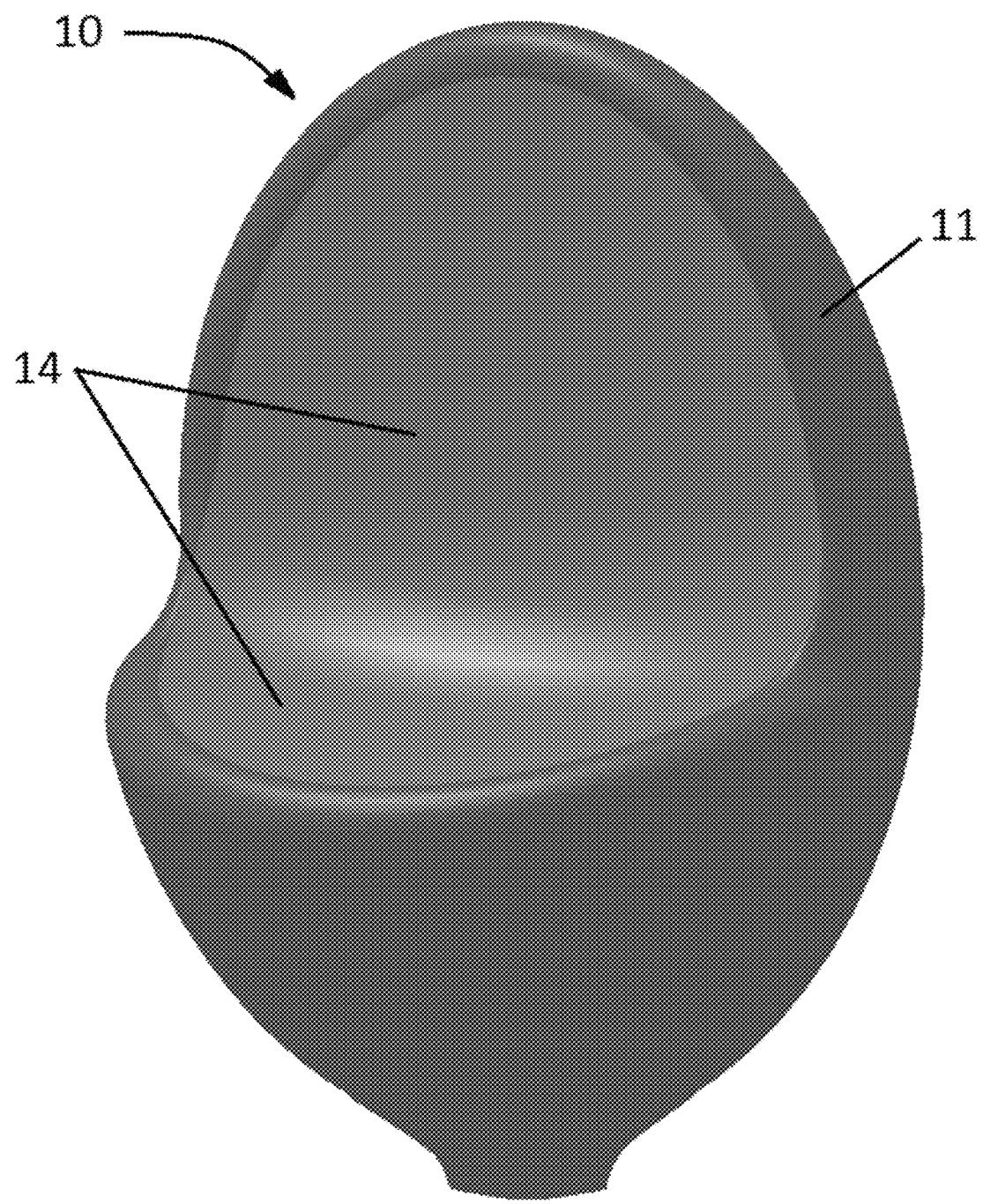
FIG. 14C is a perspective view of the applicator shown in FIGS. 14A and 14B according to one embodiment of the present invention.

The embodiment shown in FIG. 14A, FIG. 14B and FIG. 14C includes ellipsoidal reflector 12 and applicator/coupling membrane 14 incorporated in the construction of the acoustic pressure shock wave applicator 10, used to treat mastitis infections or prophylactic treatment to prevent mastitis of the udder 22 from a cow 20 (see FIG. 2). In this case the acoustic pressure shock wave treatment is applied to soft tissue and possible scar tissue that are part of the infected udder 22. In this embodiment, in order to maximize the output energy in the treated area, the ellipsoidal reflector 12 has a larger reflective area when compared with the embodiments from FIG. 8, FIG. 9 or FIG. 10 where the ellipsoidal reflector 12 is half of an ellipsoid. As will be appreciated from FIG. 14A, the ellipsoidal reflector 12 extends beyond the small axis of the ellipsoid 44 almost entirely to the large axis of the ellipsoid 46 on left side of the ellipsoidal reflector 12. In this way, if a full ellipsoid is considered to be similar to an egg composed of four volumetric parts (lower left side, lower right side, upper left side and upper right side), this embodiment provides an ellipsoidal reflector 12 as composed of three of those parts, respectively, a lower left side, lower right side, and upper left side (see FIG. 14C). This construction of the ellipsoidal reflector 12 allows a larger reflective area, which ultimately results in a larger focal volume 18 for the focused acoustic pressure shock waves 29 (schematically shown in FIG. 2) and increased energy deposited inside the infected udder 22. Furthermore, the ellipsoidal reflector 12 from FIG. 14A, FIG. 14B and FIG. 14C is dimensionally larger (larger reflective area due to its larger dimensions) when compared with the ellipsoidal reflector 12 presented in FIG. 8, FIG. 9 or FIG. 10, which further increases the energy deposited inside the infected udder 22. The dimensions of the aperture of the ellipsoidal reflector 12 are chosen so as to be able to receive an infected cow udder 22 and the applicator/coupling membrane 14 is also specially formed in a concave "L" shape (see FIG. 14C) to allow its attachment to the ellipsoidal reflector 12. For optimal transmission of acoustic pressure shock waves 29 sufficient acoustic transmission couplings gel (not shown in FIG. 14A, FIG. 14B and FIG. 14C) is preferably used in between the udder 22 being treated and the applicator/coupling membrane 14, which will acoustically couple the udder 22 with applicator/coupling membrane 14.

In the embodiment of FIGS. 14A-14C, ellipsoidal reflector 12 and applicator/coupling membrane 14 of the acoustic pressure shock wave applicator 10 provide a high energy efficiency solution to treat mastitis infections of the udder 22 localized superficially, i.e. behind the skin, of the udder 22. In this embodiment, if the focal volume 18 (created by the focused acoustic pressure shock waves 29 (schematically shown in FIG. 2)) has an overall dimension that corresponds to the dimensions of the infected area, the treatment can be performed with the acoustic pressure applicator 10 in only one position. Also, the focal volume 18 is preferably placed tangential to the skin of the udder 22, which allows a larger area to be treated in one position of the acoustic pressure shock wave applicator 10, when compared with the embodiment from FIG. 8 where the focal volume 18 is oriented perpendicular to the skin of the udder 22 (the focal volume 18 is transversally intersected by the targeted area instead of longitudinally as seen in FIG. 14A). If the area of infection of the udder 22 is larger than the overall dimensions of the focal volume 18, then the acoustic pressure shock wave applicator 10 of FIG. 14A, FIG. 14B and FIG. 14C is preferably moved in any direction around/along the udder 22. It is preferable that the movement of the acoustic pressure shock wave applicator 10 to be done in such way "to paint" all the targeted area affected by infection.

For the embodiment presented in FIG. 14A, FIG. 14B and FIG. 14C, for mastitis treatment or prophylactic treatment to prevent mastitis with acoustic pressure shock waves 29 (schematically shown in FIG. 2) of an udder 22 from cow 20 (see FIG. 2), similar discharge voltages, same energy flux density inside the focal volume 18 for each acoustic pressure shock wave 29, equivalent frequency range, similar total number of acoustic pressure shock waves 29 delivered in one session and identical session sequence function of somatic cell count (SCC) as presented for embodiment from FIG. 2 are preferably used.

Figure 15:
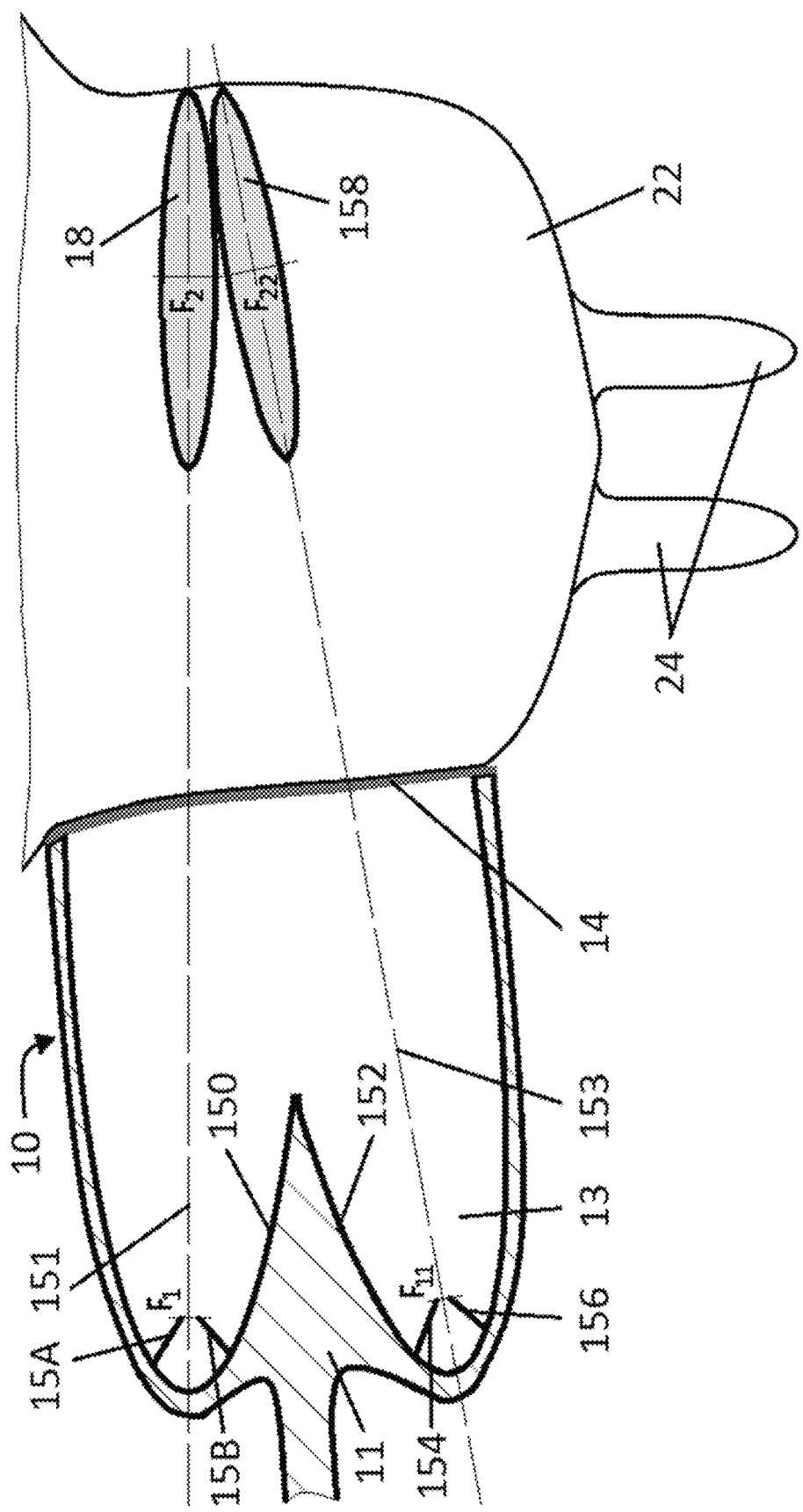
FIG. 15 is a schematic view of an applicator that uses two fused reflectors to deliver acoustic pressure shock waves to an udder affected by mastitis according to one embodiment of the present invention.

The embodiment shown in FIG. 15 includes an acoustic pressure shock wave applicator 10 that incorporates two reflectors in its construction for more efficient treatment of mastitis infections or prophylactic treatment to prevent mastitis of the udder 22 from a cow 20 (see FIG. 2). The combination of first ellipsoidal reflector 150 with the second ellipsoidal reflector 152 can be used to increase efficiency through addition of focal volume 18 from first ellipsoidal reflector 150 with the adjacent/non-overlapping second focal volume 158 from the second ellipsoidal reflector 152. In this way the spatial distribution of the overall focal volume (combination of the focal volume 18 together with the second focal volume 158) allows the treatment of a larger area of an udder 22 from one position of the acoustic pressure shock wave applicator 10. If an overlap of the focal volumes 18 and 158 (not shown in FIG. 15) is desired then such arrangement can be realized, and allows an increased output energy (double the amount for two reflectors, triple the amount for three reflectors, etc) that is deposited in the targeted tissue, which in this case is the infected tissue from the udder 22. The overlap or non-overlap of the two focal volumes 18 and 158 is dictated by the orientation/angle in between the first focal line 151 and second focal line 153. For the acoustic pressure shock wave applicator 10 that incorporates two reflectors 150 and 152, the first focal line 151 and second focal line 153 preferably intersect to allow the overlap of the two focal volumes 18 and 158 in the targeted area. Based on the geometry of the two reflectors and the construction of the applicator/coupling membrane 14, the penetration can be superficial, medium or deep and can be fixed or variable (via inflating or deflating of the applicator/coupling membrane 14), as described with respect to the embodiments from FIG. 8, FIG. 9, and FIG. 10.

With continuing reference to FIG. 15, the high voltage discharge in $F_1$ (in between first electrode 15A and second electrode 15B in the fluid present in reflector cavity 13) of the first ellipsoidal reflector 150 and $F_{11}$ (in between third electrode 154 and fourth electrode 156 in the fluid present in reflector cavity 13) of the second ellipsoidal reflector 152 can be done simultaneously or sequentially, which can be a setting in the software of the control unit 28 (see FIG. 2). The two (2) reflectors share a common applicator/coupling membrane 14 that is placed in contact with a body appendage or body in general (human or animal), and in this particular example of FIG. 15, with udder 22. The applicator/coupling membrane 14 can be also used to adjust infected tissue penetration in the order of millimeters by inflating and deflating it, when the control unit 28 has the capability to introduce and retrieve fluid from inside the reflector cavity 13.

Although the embodiment of FIG. 15 shows an acoustic pressure shock wave applicator 10 that incorporates two reflectors 150 and 152, based on the needs for each particular treatment situation the acoustic pressure shock wave applicator 10 can incorporate more than two reflectors that share a common applicator/coupling membrane 14.

In the embodiment shown in FIG. 15 the acoustic pressure shock wave treatment is applied to soft tissue and possible scar tissue that are part of the infected udder 22. For optimal transmission of acoustic pressure shock waves 29 (schematically shown in FIG. 2) sufficient acoustic transmission couplings gel (not shown in FIG. 15) is preferably used in between the udder 22 being treated and the applicator/coupling membrane 14, which will acoustically couple the udder 22 with applicator/coupling membrane 14.

If the area of infection of the udder 22 is larger than the overall dimensions of the focal volumes 18 and 158, then the acoustic pressure shock wave applicator 10 presented in FIG. 15 is preferably moved in any direction around/along the udder 22. It is preferable that the movement of the acoustic pressure shock wave applicator 10 be done in such way "to paint" all the targeted area affected by infection and the focal volumes 18 and 158 to completely cover volumetrically the volume of the udder 22 affected by infection.

For the embodiment presented in FIG. 15, for mastitis treatment or prophylactic treatment to prevent mastitis with acoustic pressure shock waves 29 (schematically shown in FIG. 2) of an udder 22 from cow 20 (see FIG. 2), similar discharge voltages, same energy flux density inside the focal volumes 18 and 158 for each acoustic pressure shock wave 29, equivalent frequency range, similar total number of acoustic pressure shock waves 29 delivered in one session and identical session sequence function of somatic cell count (SCC) are preferably used, as presented for the embodiment from FIG. 2.

The embodiment of FIG. 15 is not restricted only for the treatment of mastitis of udder 22 of a cow 20 (see FIG. 2), and it can be used for other treatments of infected tissue for both human and animals, as presented for the embodiments described throughout this patent. The multiple reflectors construction of the acoustic pressure shock wave applicator 10 is advantageous for providing more efficient treatment. For example, in the treatment of an infected hip implant/prosthesis 16 (as presented in FIG. 1A, FIG. 1B, FIG. 1C, FIG. 1D, FIG. 1E, and FIG. 1F) using an acoustic pressure shock wave applicator 10 that includes multiple reflectors can be used to enhance the energy deposited in the targeted area by configuring the reflectors 150 and 152 to have their focal volumes (first focal volume 18 and the second focal volume 158) overlapped and thus increasing two fold the amount of energy deposited in the targeted tissue for more efficient killing of the pathogens. If the focal volumes 18 and 158 are not overlapped and rather adjacent to each other there can alternatively be an increased coverage of the targeted area in one position of the acoustic pressure shock wave applicator 10. This translates in more efficient coverage of the targeted area, with less movements of the acoustic pressure shockwave applicator 10 necessary to cover the entire infected area. The same rationale of increased efficiency (for output energy or treatment area coverage) can be applied for the treatment of any type of tissue (hard, semi-hard, and soft), type of infection (bone infection, skin infection, subcutaneous or deep infections, mastitis, toe fungus, organs, etc.) for both humans and animals.

For the example presented in embodiment from FIG. 15 the electrohydraulic principle using spark gap high voltage discharges was described. However, piezoelectric constructions or electromagnetic constructions can be used, which can be similar to the embodiments presented in FIG. 1C, FIG. 1D, FIG. 1E, and FIG. 1F.

For the embodiments that use acoustic pressure shock waves treatment for cow mastitis (for udder 22 or teat 24 or both), shock waves can be the sole treatment or can be done in conjunction with other therapies (drugs, caps, etc.) for additive results.

Any of the embodiments presented in FIG. 1A, FIG. 1B, FIG. 1C, FIG. 1D, FIG. 1E, FIG. 1F, FIG. 2, FIG. 3, FIG. 8, FIG. 9, FIG. 10, FIG. 11, FIG. 12, FIG. 13, FIG. 14A, FIG. 14B, FIG. 14C and FIG. 15 may be provided in embodiments wherein the acoustic pressure shock wave applicators 10 have a fixed volume enclosed in between the ellipsoidal reflector 12/parabolic reflector 12A and applicator/coupling membrane 14. In other embodiments the control unit 28 (see FIG. 2) has the capability to introduce and retrieve fluid inside the reflector cavity 13, which coupled with a very flexible applicator/coupling membrane 14 allows the acoustic pressure shock wave applicators 10 to be able to adjust the height applicator/coupling membrane 14 and ultimately let the user to adjust penetration of the acoustic pressure shock waves 29 (schematically shown in FIG. 2) inside the body, to precisely hit the desired targeted tissue (human or animal). The variable penetration for an acoustic pressure shock wave applicator 10 allows the operator to use only one acoustic pressure shock wave applicator 10 to cover large volume infections affecting humans or animals at different penetrations under the skin. If acoustic pressure shock wave applicators 10 have fixed volume enclosed in between the ellipsoidal reflector 12/parabolic reflector 12A and applicator/coupling membrane 14, then the user might need several acoustic pressure shock wave applicators 10 for the treatment of the entire infection covering infections spread over a large volume inside the human or animal body (ranging from the skin to deep inside the body).

For FIG. 4A, FIG. 4B, FIG. 5A, FIG. 5B, FIG. 6A, FIG. 6B, FIG. 6C, FIG. 7A, FIG. 7B, and FIG. 7C the control unit 28 (see FIG. 2) has the capability to introduce and retrieve fluid inside the reflector cavity 13, which coupled with a very flexible applicator/coupling membrane 14 allows the acoustic pressure shock wave applicators 10 to be able to adjust the contact of the applicator/coupling membrane 14 with the targeted area, which can accommodate a larger variation in the size of the targeted area/anatomic feature or appendage treated (for example the teat 24, udder 22, toe 40, finger, tail, etc.)

For all embodiments presented herein, the applicator/coupling membrane 14 is preferably flexible and can adapt to anatomical dimensional variations. In some cases the applicator/coupling membrane 14 can be made of a hard material, which does not impede with the acoustic pressure shock waves propagation. Using a hard material for the applicator/coupling membrane 14 introduces the disadvantage of not allowing for variable penetration for one acoustic pressure shock wave applicator 10 and multiple such acoustic pressure shock wave applicators 10 may be needed to achieve different tissue penetrations.

As an example, in the majority of embodiments described herein, the acoustic pressure shock wave applicators 10 employ the electrohydraulic principle with high voltage discharge in between electrodes 15A and 15B in a fluid that fills reflector cavity 13 to produce acoustic pressure shock waves 29 (schematically shown in FIG. 2). In alternative embodiments using the electrohydraulic principle one or more incased lasers 15C, 15D from FIG. 1B can replace the electrodes 15A and 15B, in order to generate acoustic pressure shock waves 29. When the piezoelectric principle is used to generate acoustic pressure shock waves 29, the piezo crystals/piezo ceramics 15E (see FIG. 1C) or piezo fibers reflector 15F (see FIG. 1D) can be used to generate acoustic pressure shock waves 29 inside the fluid-filled reflector cavity 13. The piezo reflector (use crystals or fibers) can be, from a geometrical point of view, an ellipsoidal reflector 12, a spherical reflector 110, a parabolic reflector 12A or a reversed reflector 130. Furthermore, if the electromagnetic principle is used an electromagnetic flat coil and plate assembly 15G (see FIG. 1E) or an electromagnetic cylindrical coil and tube plate assembly 15H (see FIG. 1F) can be used instead of the electrodes 15A and 15B to produce acoustic pressure shock waves 29 inside the fluid-filled reflector cavity 13.

The embodiment presented in FIG. 3 shows the specific treatment of a teat 24 from a cow 20 (see FIG. 2) infected with mastitis. In this case the acoustic pressure shock wave applicator 10 is dimensionally designed to allow the proper treatment of the teat 24. To accomplish such result, the applicator/coupling membrane 14 preferably has sufficient height to allow the reach of the teat 24, without being impeded by the presence of the udder 22. The embodiments from FIG. 11 and FIG. 12 show acoustic pressure applicators 10 that use radial acoustic pressure shock waves 112 and pseudo-planar acoustic pressure shock waves 122, respectively, in order to treat targeted tissue 114 (human or animal) in general, which might as well be a teat 24.

The teat 24 during its treatment has the tendency to flex when the acoustic pressure shock wave applicator 10 is pressed against it (see FIG. 3, FIG. 11 or FIG. 12) to ensure a proper acoustic coupling of the teat 24 with applicator/coupling membrane 14 via acoustic transmission coupling gel (not shown in FIG. 3, FIG. 11 or FIG. 12). To have a steady teat 24 during treatment with acoustic pressure shock waves 29 (schematically shown in FIG. 2), the teat treatment fixture 160 from FIG. 16 is preferably used.

Figure 16:
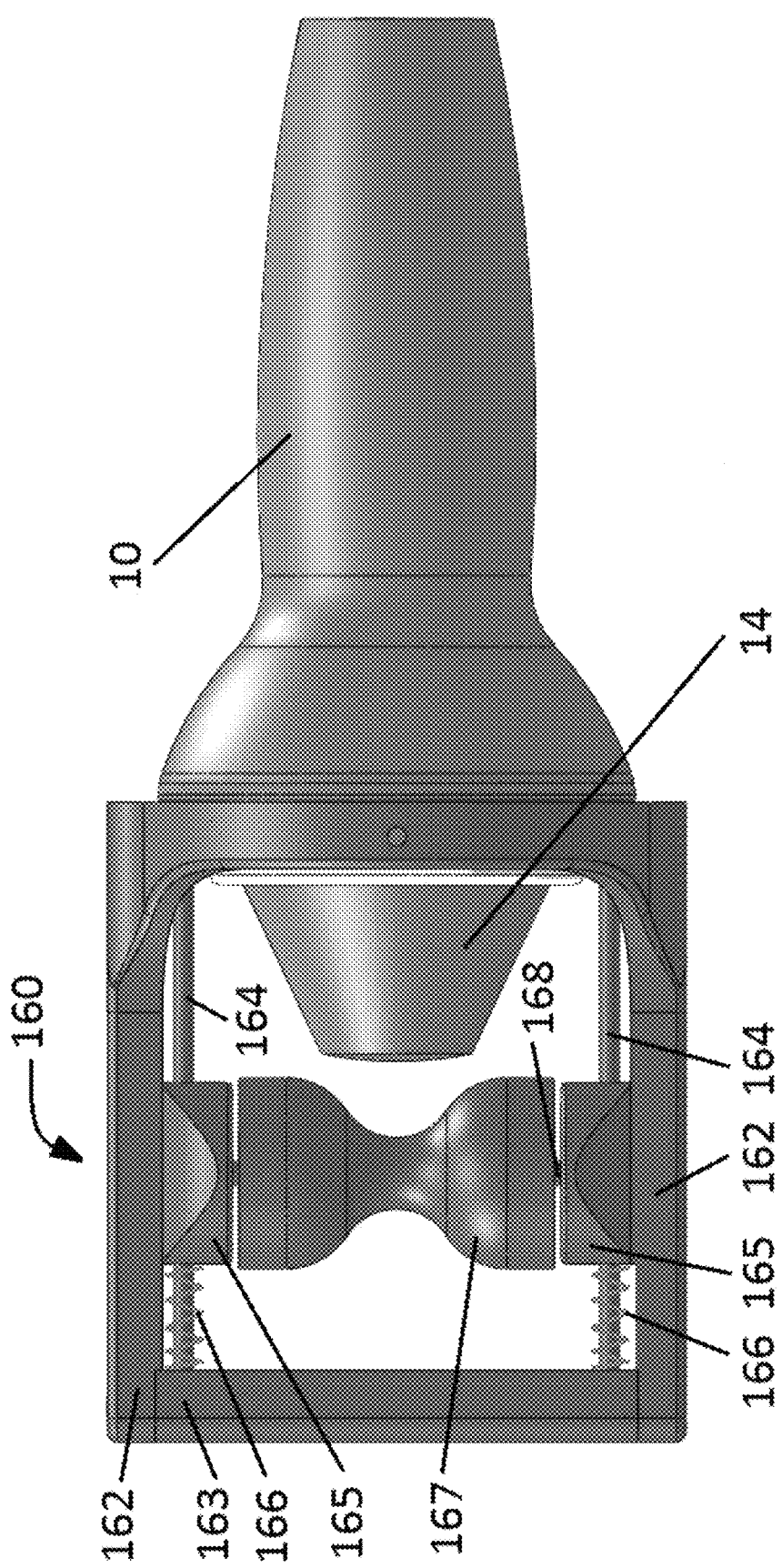
FIG. 16 is a schematic view of a teat treatment device for treating the teats for cow mastitis using applicator embodiments as presented in FIGS. 3, 11, and 12, according to one embodiment of the present invention.

According to FIG. 16, the acoustic pressure shock wave applicator 10 can be installed into the teat treatment fixture 160 using a dedicated slot into the lateral frame 162. To ensure the rigidity of the teat treatment fixture 160, the lateral frame 162 (that has a "U"-shape) is assembled on the open end with the top frame 163. Two guiding rods 164 are mounted inside the overall frame, to allow a controlled movement of the slides 165 away and towards the acoustic pressure shock wave applicator 10. The slides 165 are restricted in their motion along the guiding rods 164 by the loading springs 166. In between the two slides 165 a teat positioner/roller 167 is rotating around the teat positioner/roller shaft 168. Practically, during application of acoustic pressure shock waves 29 (schematically shown in FIG. 2), the teat 24 is retained in between the applicator/coupling membrane 14 and teat positioner/roller 167, which will prevent the bending of the teat 14 during treatment. Due to the presence of the loading springs 166, the teat 24 (not shown in FIG. 16) is automatically pushed against the teat positioner/roller 167, which allow a good contact of the teat 24 with the applicator/coupling membrane 14 of the acoustic pressure shock wave applicator 10.

Figure 17A:
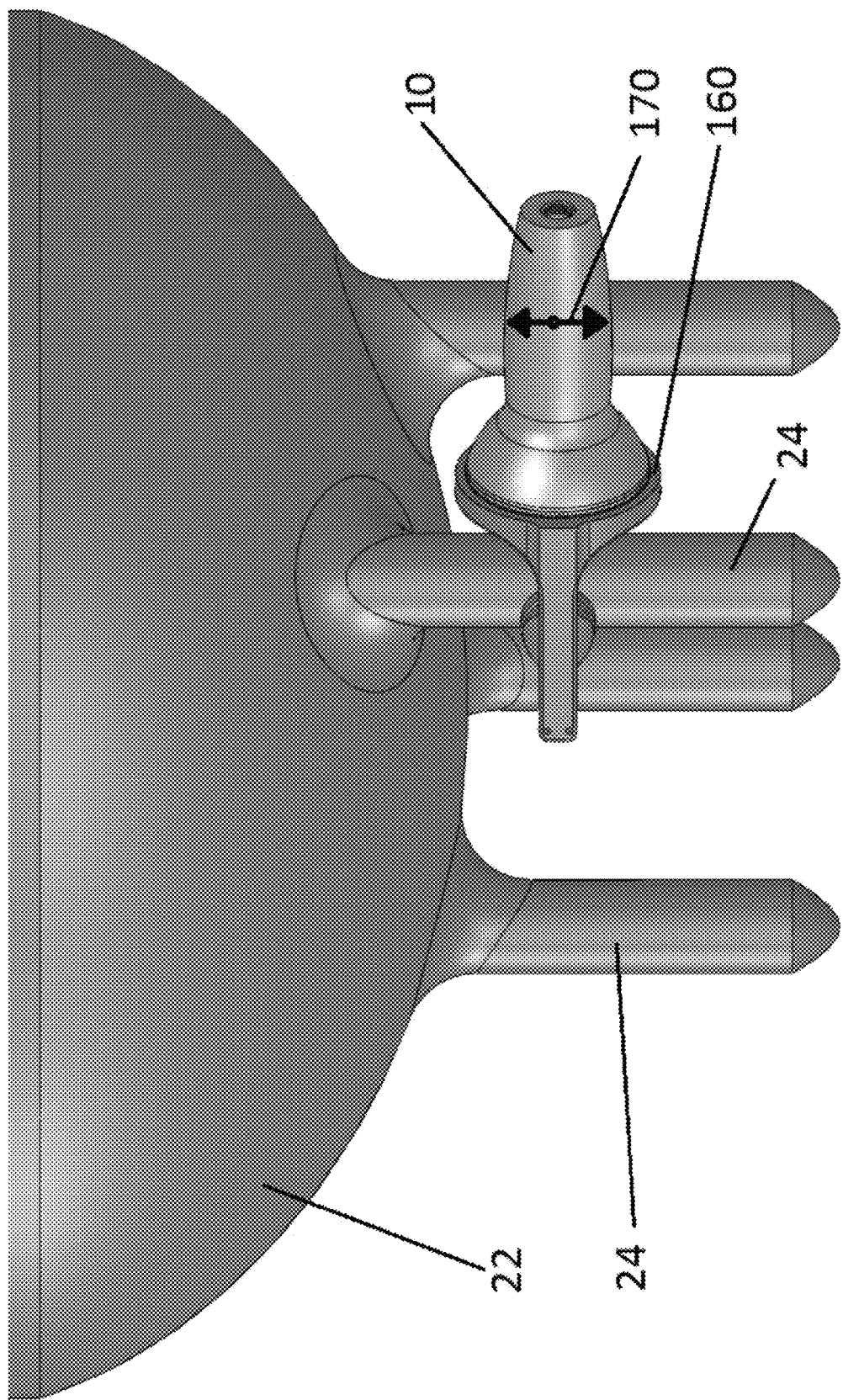
FIG. 17A is a perspective view from the side of an udder showing use of the teat treatment device shown in FIG. 16, according to one embodiment of the present invention.
Figure 17B:
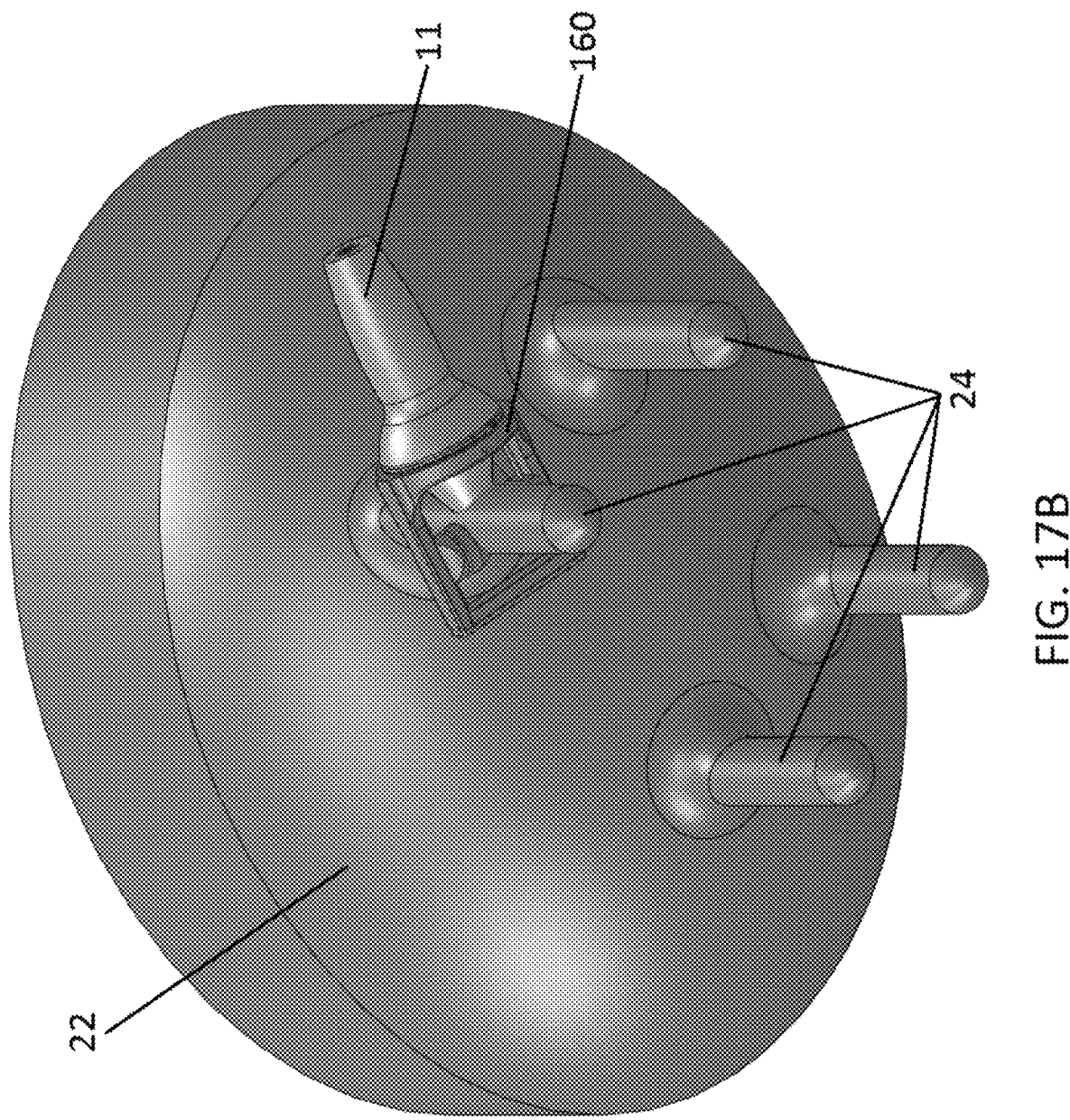
FIG. 17B is a perspective view from under an udder showing use of the teat treatment device shown in FIG. 16, according to one embodiment of the present invention.

The teat treatment fixture 160 presented in FIG. 16 can be moved up/down the teat 24, similar to a milking motion 170 (see FIG. 17A), to cover completely the whole height of the teat 24 affected by infection. Due to rotational movement of the teat positioner/roller 167 around the teat positioner/roller shaft 168 (see FIG. 16), a high comfort level is provided for the teat 24 during treatment using the teat treatment fixture 160. FIG. 17A and FIG. 17B show in a three dimensional fashion the actual use of the teat treatment fixture 160 on the teat 24 and the actual milking motion 170 that prevents the lateral bending of the teat 24 during treatment with the acoustic pressure shock wave applicator 10.

EXAMPLE

An actual safety study was performed using acoustic pressure shock waves 29 (schematically shown in FIG. 2) in lactating dairy cattle with clinical mastitis. The objective of the study was to evaluate the effects of acoustic pressure shock waves 29 on the systemic health and the health of the mammary gland in lactating dairy cattle with clinical mastitis. Additional information was collected on the daily somatic cell counts (SCC).

One group (Group 1) included 6 cows that were treated at the lowest energy setting for acoustic pressure shock waves (E1 setting that produces a flux density of 0.2 mJ/mm$^2$ in the targeted area) once daily for 5 days. The second group (Group 2) was treated at the highest energy setting for acoustic pressure shock waves (E6 setting that produces a flux density of 0.4 mJ/mm$^2$ in the targeted area) once daily for 5 days. Both Group 1 and Group 2 used 1,500 acoustic pressure shock waves per session at 4 Hz frequency. The third group (Group 3) was treated with intra-mammary antimicrobials (ceftiofur hydrochloride, Spectramast LC) once daily for 5 days. All the cows had only one quarter affected by mastitis that was treated during this study.

The safety study showed no difference between outcomes of the three groups and no adverse effects produced by acoustic pressure shock waves on the systemic health and the health of the mammary gland in lactating dairy cattle with clinical mastitis. Furthermore, the cows tolerated the acoustic pressure shock waves treatment well and in general by day 3 the milk was grossly normal.

There were no differences in somatic cell count between groups or days during the study, as determined by Two Way Repeated Measures ANOVA (One Factor Repetition) analysis. Due to the small number of cows studied (6 cows for each group that gives a total 18 cows) significant variation in the somatic cell count (SCC) between animals and between days within the same animal was observed, but in general no increase or a decreasing trend of the daily SCC was observed.

Figure 18:
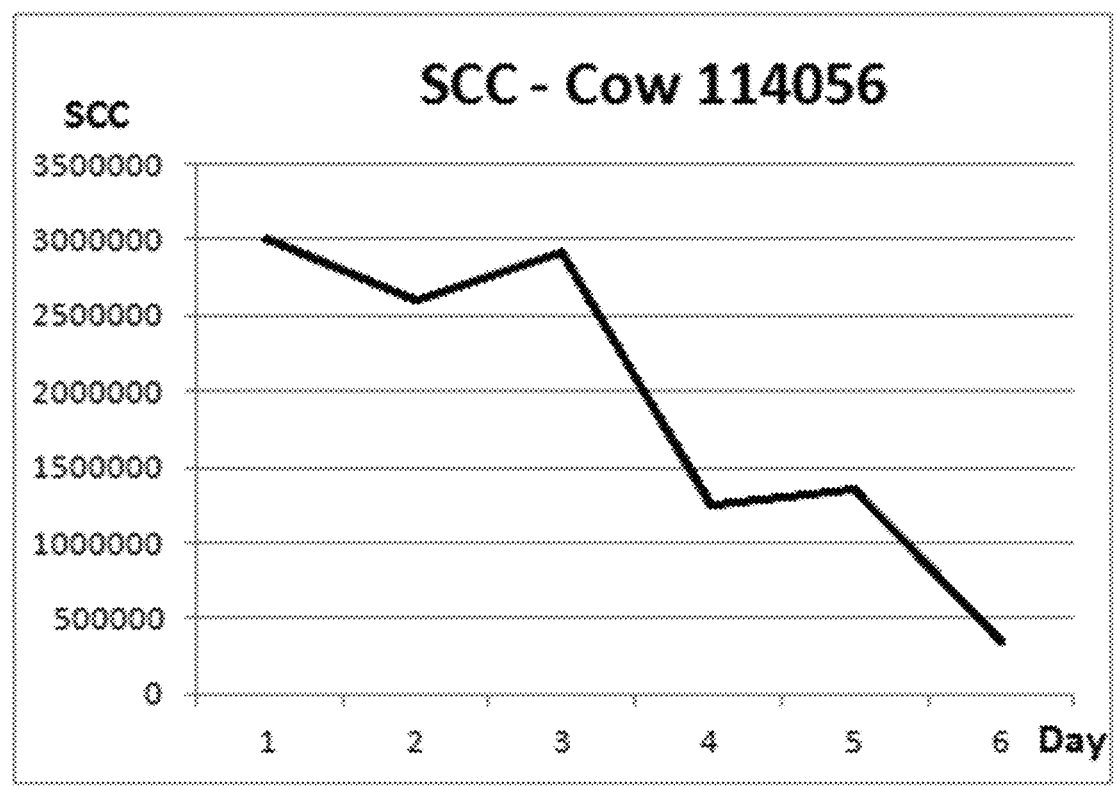
FIG. 18 is a graph showing somatic cell count (SCC) results for a cow treated one time per day for a total of six consecutive acoustic pressure shock wave treatments at low energy setting, according to one embodiment of the present invention.

Somatic cell count (SCC) results for the cows treated with acoustic pressure shock waves, is shown in FIG. 18. SCC daily count for cow 114056 treated at E1 setting that produces a flux density of 0.2 mJ/mm$^2$ in the targeted area. This cow had significant mastitis infection mastitis with the SCC of 3,008,000 for the milk collected in Day 1. The SCC show a downward trend with the lowest value for SCC of 349,000 at Day 6, which represents an 88% drop when compared to Day 1.

Figure 19:
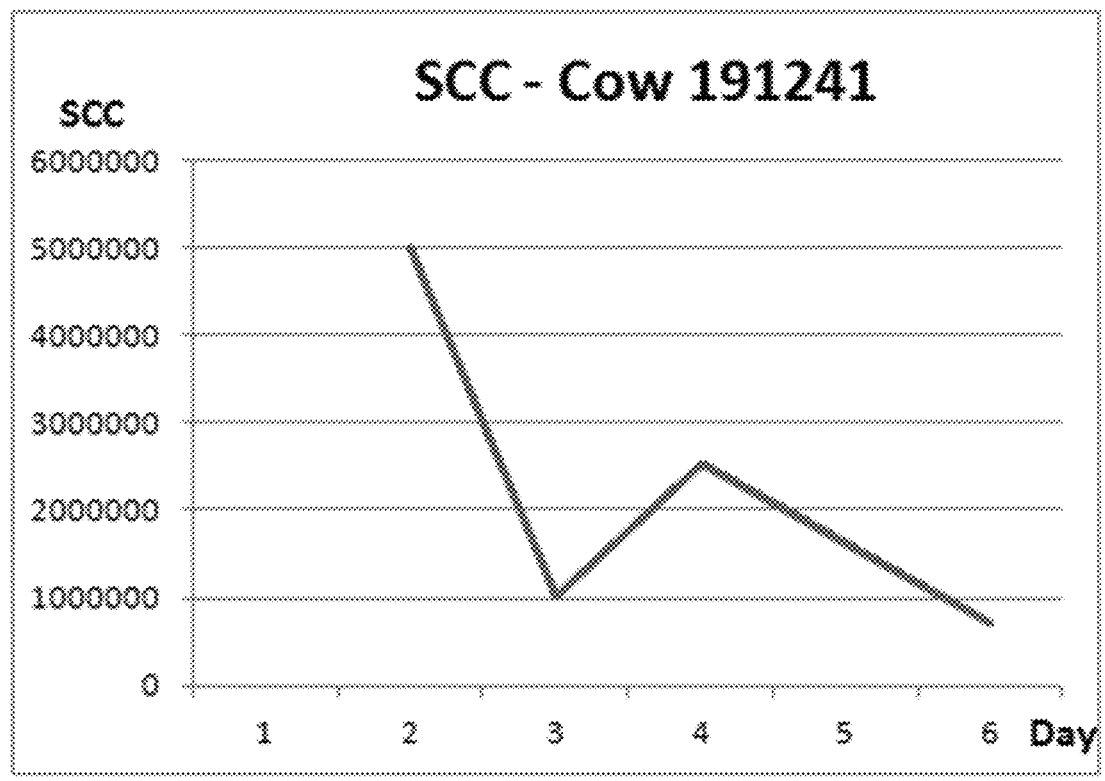
FIG. 19 is a graph showing somatic cell count (SCC) results for a cow treated one time per day for a total of six consecutive acoustic pressure shock wave treatments at high energy setting, according to one embodiment of the present invention.

FIG. 19 shows the SCC daily count for cow 191241 treated at E6 setting that produces a flux density of 0.4 mJ/mm$^2$ in the targeted area. This cow had serious mastitis infection mastitis with the SCC of 5,000,000 for the milk collected in Day 2 (data for Day 1 was not collected). The SCC show a downward trend with the lowest value for SCC of 717,000 at Day 6, which represents an 86% drop when compared to Day 1.

The acoustic pressure shock wave technology can be coupled with technologies designed to precisely locate the position of the focal infection inside the tissue, to allow a more efficacious treatment. These technologies that use infrared detection, light analysis, laser detection, and the like, can in other embodiments increase the efficiency of the acoustic pressure shock wave treatment for disinfection by focusing the treatment where it is needed.

Acoustic pressure shock waves used in embodiments of the invention can be transmitted in any angle possible relative to the target without any heat loss along the pathway (regardless of the distance traveled to the targeted area), can be focused or un-focused, can penetrate any type of tissue (hard, semi-hard, soft) at any distance and can treat superficial or profound seated infections, using an extracorporeal/non-invasive approach.

Non-limiting examples of application of acoustic pressure shock wave treatment for different types of infections that are covered by this patent for humans and animals include the following (not restrictive or all-inclusive):
Skin infections
Chronic wound infections
Surgery incision infections
Subcutaneous infections
Deep infections (soft tissue, bone, ligaments, tendons, etc.)
Organs infections
Joint infections
Prosthesis/implant infections
Toe infections
Teats infections
Udder infections
Paws infections
Tail infections While the invention has been described with reference to exemplary structures and methods in embodiments, the invention is not intended to be limited thereto, but to extend to modifications and improvements within the scope of equivalence of such claims to the invention.

Although the examples from this patent refer specifically to human living tissue infections and mastitis treatment for milking mammals/animals, embodiments can also be used for other medical applications (besides living tissue infection) for humans or animals, where the specific construction of the applicators conforms very well to particular anatomic features of the body as toes, torso, legs, etc., for an optimal delivery of acoustic pressure shock waves to the targeted treatment area, as required by a specific medical condition that needs to be addressed.

What is claimed is:

1. An acoustic pressure shock wave applicator for treatment of a protruding appendage of a human or animal body comprising:
   a shock wave generator at a first focal point (F1) of the shock wave applicator and supported within an interior space defined by walls of a reflector, wherein the reflector opens to an aperture for passage of acoustic pressure shock waves generated at the shock wave generator, and wherein the reflector comprises an ellipsoidal shape having a major axis and minor axis, and wherein edges of the reflector walls extend beyond the minor axis and terminate at the aperture with a reflector diameter being shorter across the aperture than a reflector diameter at the minor axis;
   a membrane covering the aperture and enclosing fluid in the interior space of the reflector, wherein the membrane includes a pre-formed pit portion having a pre-determined size and shape and extending inward from the edges of the reflector walls at the aperture toward the interior space of the reflector and configured to fit a protruding appendage in a longitudinal approach along the appendage's longitudinal axis in the pit portion and wherein a second focal point (F2) of the shock wave applicator is located within the pit portion to provide a shock wave focal volume overlapping the pit portion.

2. The acoustic pressure shock wave applicator of claim 1, wherein the pit portion is shaped to receive the appendage that is at least one of a bovine, ovine and caprine teat.

3. The acoustic pressure shock wave applicator of claim 2, further comprising a control unit coupled to shock wave generator and configured to provide energy flux density in the range of about 0.10 to about 0.40 mJ/mm$^2$, configured to provide between about 1,000 to about 3,000 acoustic pressure waves per teat treatment session and configured to provide a frequency of acoustic pressure shock waves from about 1 to about 8 Hz.

4. The acoustic pressure shock wave applicator of claim 2, further comprising a control unit coupled to the shock wave generator and configured to provide energy flux density in the range of about 0.10 to about 0.50 mJ/mm$^2$, configured to provide between about 1,000 to about 3,000 acoustic pressure waves per teat treatment session and configured to provide a frequency of acoustic pressure shock waves from about 1 to about 8 Hz.

5. The acoustic pressure shock wave applicator of claim 2, further comprising a control unit coupled to shock wave generator and configured to provide energy flux density in the range of about 0.20 to about 0.60 mJ/mm$^2$, configured to provide between about 1,000 to about 3,000 acoustic pressure waves per teat treatment session and configured to provide a frequency of acoustic pressure shock waves from about 1 to about 8 Hz.

6. The acoustic pressure shock wave applicator of claim 1, wherein the pit portion is shaped to receive the appendage that is at least one of a toe, finger, nose and tail.

7. The acoustic pressure shock wave applicator of claim 1, wherein said shock wave generator is selected from the group consisting of an electromagnetic shock wave generator, an electrohydraulic shock wave generator, a piezo fiber shock wave generator, a piezo crystal shock wave generator, a piezo ceramic shock wave generator and a laser shock wave generator.

8. The acoustic pressure shock wave applicator of claim 1, wherein the shock wave generator, the first and second focal points (F1) and (F2), and the reflector are aligned so that the focal volume will cover the entirety of the protruding appendage that the pre-formed pit portion is configured to fit.

9. The acoustic pressure shock wave applicator of claim 1, further comprising a control unit coupled to the shock wave generator and configured to treat at least one of an infection and wound of soft and semi-hard tissue of the appendage with energy flux density in the range of from about 0.10 to about 0.80 mJ/mm$^2$, configured to provide between about 2,000 to about 8,000 acoustic pressure waves per appendage treatment session and configured to provide a frequency of acoustic pressure waves from about 1 to about 8 Hz.

10. An acoustic pressure shock wave applicator for treatment of a protruding appendage of a human or animal body comprising:
a shock wave generator at a first focal point (F1) of the shock wave applicator and supported within an interior space defined by walls of a reflector, wherein the reflector opens to an aperture for passage of acoustic pressure shock waves generated at the shock wave generator, and wherein the reflector comprises an ellipsoidal shape having a major axis and minor axis and an edge of the reflector walls terminating at the aperture extends beyond the minor axis;
and a concave, inward L-shaped or U-shaped membrane covering the aperture, wherein the membrane encloses fluid within the reflector, and wherein the membrane is configured to provide an opening that receives and fits a protruding appendage in a lateral approach perpendicular to the longitudinal axis of the appendage in the opening through a side of the applicator, and wherein a second focal point (F2) of the shock wave applicator is located within the opening to provide a shock wave focal volume overlapping the opening.

11. The acoustic pressure shock wave applicator of claim 10, wherein the opening is shaped to receive the appendage that is at least one of a bovine, ovine and caprine teat.

12. The acoustic pressure shock wave applicator of claim 11, further comprising a control unit coupled to the shock wave generator and configured to provide energy flux density in the range of from about 0.10 to about 0.40 mJ/mm$^2$, configured to provide between about 1,000 to about 3,000 acoustic pressure waves per teat treatment session and configured to provide a frequency of acoustic pressure shock waves from about 1 to about 8 Hz.

13. The acoustic pressure shock wave applicator of claim 11, further comprising a control unit coupled to shock wave generator and configured to provide energy flux density in the range of about 0.10 to about 0.50 mJ/mm$^2$, configured to provide between about 1,000 to about 3,000 acoustic pressure waves per teat treatment session and configured to provide a frequency of acoustic pressure shock waves from about 1 to about 8 Hz.

14. The acoustic pressure shock wave applicator of claim 11, further comprising a control unit coupled to shock wave generator and configured to provide energy flux density in the range of about 0.20 to about 0.60 mJ/mm$^2$, configured to provide between about 1,000 to about 3,000 acoustic pressure waves per teat treatment session and configured to provide a frequency of acoustic pressure shock waves from about 1 to about 8 Hz.

15. The acoustic pressure shock wave applicator of claim 10, wherein the opening is shaped to receive the appendage that is at least one of a toe, a finger, a tail and a nose.

16. The acoustic pressure shock wave applicator of claim 10, wherein said at least one shock wave generator is selected from the group consisting of an electromagnetic shock wave generator, an electrohydraulic shock wave generator, a piezo fiber shock wave generator, a piezo crystal shock wave generator, a piezo ceramic shock wave generator and a laser shock wave generator.

17. The acoustic pressure shock wave applicator of claim 10, wherein the shock wave generator, the first and second focal points (F1) and (F2), and the reflector are aligned so that the focal volume will cover the entirety of the protruding appendage that the opening is configured to fit.

18. The acoustic pressure shock wave applicator of claim 10, further comprising a control unit coupled to the shock wave generator and configured to treat at least one of an infection and wound of soft and semi-hard tissue of the appendage with energy flux density in the range of from about 0.10 to about 0.80 mJ/mm$^2$, configured to provide between about 2,000 to about 8,000 acoustic pressure waves per appendage treatment session and configured to provide a frequency of acoustic pressure waves from about 1 to about 8 Hz.

19. The acoustic pressure shock wave applicator of claim 10, wherein the opening is shaped to receive the appendage that is an udder.

* * * * *